US008367067B2

(12) United States Patent
Jackson et al.

(10) Patent No.: US 8,367,067 B2
(45) Date of Patent: Feb. 5, 2013

(54) IMMUNOGENIC LIPOPEPTIDES COMPRISING T-HELPER AND B-CELL EPITOPES

(75) Inventors: David Jackson, North Balwyn (AU); Weiguang Zeng, Kensington (AU)

(73) Assignee: The Council of the Queensland Institute of Medical Research, Herston (AU)

( * ) Notice: Subject to any disclaimer, the term of this patent is extended or adjusted under 35 U.S.C. 154(b) by 332 days.

(21) Appl. No.: 12/488,485

(22) Filed: Jun. 19, 2009

(65) Prior Publication Data

US 2010/0092500 A1    Apr. 15, 2010

Related U.S. Application Data

(62) Division of application No. 10/525,301, filed as application No. PCT/AU03/01018 on Aug. 12, 2003, now Pat. No. 7,569,225.

(60) Provisional application No. 60/402,838, filed on Aug. 12, 2002.

(51) Int. Cl.
*A61K 39/00* (2006.01)
(52) U.S. Cl. ............... 424/184.1; 530/333; 530/359; 530/327; 530/326; 424/185.1; 424/193.1
(58) Field of Classification Search ............... 424/184.1, 424/185.1, 193.1; 530/359, 327, 326, 333
See application file for complete search history.

(56) References Cited

U.S. PATENT DOCUMENTS

| 5,580,563 A | 12/1996 | Tam |
| 5,700,910 A | 12/1997 | Metzger et al. |
| 6,024,964 A | 2/2000 | Jung et al. |

FOREIGN PATENT DOCUMENTS

| WO | WO-93/15205 | 8/1993 |
| WO | WO-93/22343 | 11/1993 |

OTHER PUBLICATIONS

Barany, Int. J. Pept. Prot. Res 30, 705-739 (1987).*
Benmohamed, L., et al., "Lipopeptide immunization without adjuvant induces potent and long-lasting B, T helper, and cytotoxic T lymphocyte responses against a malaria liver stage antigen in mice and chimpanzees," Eur. J. Immunol, 1997, pp. 1242-1253, vol. 27.
Benmohamed, L., et al., "High immunogenicity in chimpanzees of peptides and lipopeptides derived from four new *Plasmodium falciparum* pre-erythrocytic molecules," Vaccine 18, 2000, pp. 2843-2855.
Boeckler, C., et al., "Design of highly immunogenic liposomal constructs combining structurally independent B cell and T helper cell peptide epitopes," Eur. J. Immunol, 1999, pp. 2297-2308, vol. 29.
Deliyannis Georgia, et al., "Induction of long-term memory CD8+ T cells for recall of viral clearing responses against influenza virus," Journal of Virology, May 2002, pp. 4212-4221, vol. 76, No. 9.
Deprez, B., et al., "Pimelautide or Trimexautide as Built-in Adjuvants Associated with an HIV-1-Derived Peptide: Synthesis and in Vivo Induction of Antibody and Virus-Specific Cytotoxic T-Lymphocyte-Mediated Response," J. Med. Chem., 1995, pp. 459-465, vol. 38.
Deprez, B., et al., "Comparative efficiency of simple lipopeptide constructs for in vivo induction of virus-specific CTL," Vaccine, 1996, pp. 375-382, vol. 14, No. 5.
Deres, K., et al., "In vivo priming of virus-specific cytotoxic T lymphocytes with synthetic lipopeptide vaccine," Nature, Nov. 30, 1989, pp. 561-564, vol. 342.
Ghosh, S., et al., "Antigenic and immunogenic properties of totally synthetic peptide-based anti-fertility vaccines," International Immunology, 1999, pp. 1103-1110, vol. 11.
Jackson, D.C., et al., "The Central Role Played by Peptides in the Immune Response and the Design of Peptide-Based Vaccines against Infectious Diseases and Cancer," Current Drug Targets, 2002, pp. 175-196, vol. 2, No. 2.
Jung, G., et al., "Increased Production of Specific Antibodies by Presentation of the Antigen Determinants with Covalently Coupled Lipopeptide Mitogens," Angew Chem, Int. Ed. Engl., 1985, pp. 872-273, No. 10.
Kaumaya, P., et al., "Peptide Vaccines Incorporating a 'Promiscuous' T-cell Epitope Bypass Certain Haplotype Restricted Immune Responses and Provide Broad Spectrum Immunogenicity," Journal of Molecular Recognition, 1993, pp. 81-94, vol. 6.
Martinon, F., et al., "Immunization of Mice With Lipopeptides Bypasses the Prerequisite for Adjuvant, Immune Response to Lipopeptides," The Journal of Immunology, 1992, pp. 3416-3422, vol. 149, No. 10.
Metzger, J., et al., "Synthetic S-(2, 3-Dihydroxypropyl)-cysteinyl Peptides Derived from the N-terminus of the Cytochrome Submit of the Photoreaction Centre of *Rhodopseudomonas viridis* Enhance Murine Splenocyte Proliferation, Novel Synthetic Lipopeptides Activate Splenocytes," Journal of Peptide Science, 1995, pp. 184-190, vol. 3.
Mühlradt, P., et al., "Isolation, Structure Elucidation, and Synthesis of a Macrophage Stimulatory Lipopeptide from Mycoplasma fermentans Acting at Picomolar Concentration," J. Exp. Med., Jun. 2, 1997, pp. 1951-1958, vol. 185, No. 11.
Mühlradt, P., et al., "Structure and Specific Activity of Macrophage-Stimulating Lipopeptides from Mycoplasma hyorhinis," Infection and Immunity, Oct. 1998, pp. 4804-4810, vol. 66, No. 10.

(Continued)

*Primary Examiner* — David Lukton
(74) *Attorney, Agent, or Firm* — Fenwick & West LLP

(57) ABSTRACT

The present invention provides synthetic immunogenic lipopeptide molecules comprising co-linear T-helper and B cell epitopes, and methods for their production and use in the generation of primary and secondary immune responses, and for the vaccination of animal subjects against particular antigens. More particularly, the present invention provides highly soluble lipopeptides wherein the lipid moiety is attached to the terminal side-chain group of an internal lysine or lysine analog, preferably to the terminal side-chain group of an internal diamino acid residue. Preferably the internal lysine or lysine analog is positioned between the T-helper epitope and the B cell epitope or within the T-helper epitope.

13 Claims, 24 Drawing Sheets

OTHER PUBLICATIONS

Nardin, E. H., et al., "A Totally Synthetic Polyoxime Malaria Vaccine Containing *Plasmodium falciparum* B Cell and Universal T Cell Epitopes Elicits Immune Responses in Volunteers of Diverse HLA Types," The Journal of Immunology, 2001, pp. 481-489, vol. 166.

Nardin, E. H., et al., "*Plasmodium falciparum* polyoximes: highly immunogenic synthetic vaccines constructed by chemoselective ligation of repeat B-cell epitopes and a universal T-Cell epitope of CS protein," Vaccine, 1998, pp. 590-600, vol. 16, No. 6.

Obert, M., et al., "Protection of mice against SV40 tumours by $Pam_3Cys$ conjugated with SV40 T antigen-derived peptide, K(698)-T(708)," Vaccine, 1998, pp. 161-169, vol. 16, No. 2/3.

Sauzet, J.-P., et al., "Long-lasting anti-viral cytotixic T lymphocytes induced in vivo with chimeric-multirestricted lipopeptides," Vaccine, 1995, pp. 1339-1345, vol. 13, No. 14.

Toyokuni, T., et al., "Synthetic Vaccines: Synthesis of a Dimeric Tn Antigen-Lipopeptide Conjugate that Elicits Immune Responses against Tn-Expressing Glycoproteins," J. Am. Chem. Soc., 1994, pp. 395-396, vol. 116.

Wiesmüller, K.-H., et al., "Synthesis of the Mitogenic S-[2, 3-Bis(palmitoyloxy) propyl]-N-palmitoylpentapeptide from *Escherichia coli* Lipoprotein," Hoppe-Seyler's Z. Physiol. Chem., 1983, pp. 593-606, Bd. 364.

Wiesmüller, K.-H., et al., "Novel low-molecular-weight synthetic vaccine against foot-and-mouth disease containing a potent B-cell and macrophage activator," Vaccine, Feb. 1989, pp. 29-33, vol. 7.

Zeng, W., et al., "Highly Immunogenic and Totally Synthetic Lipopeptides as Self-Adjuvanting Immunocontraceptive Vaccines," Journal of Immunology, Nov. 1, 2002, pp. 4905-4912, vol. 169, No. 9.

Supplementary Partial European Search Report, EP 03783851, Aug. 22, 2007, 3 Pages.

Supplementary European Search Report, European Patent Application No. 03783852.1, Sep. 7, 2007, 9 Pages.

\* cited by examiner

|  | Solubility |
|---|---|
| Th | ++++ |
| B | ++++ |
| [Th]-[B] | +++ |
| [Th]-Lys-[B] | +++ |
| Pam₃Cys-[Th]-[B] | +/- |
| Pam₃Cys-Ser-Ser-[Th]-[B] | +/- |
| Pam₂Cys-[Th]-[B] | + |
| Pam₂Cys-Ser-Ser-[Th]-[B] | + |
| [Th]-*Lys*(Pam₃Cys)-[B] | ++++ |
| [Th]-*Lys*(Pam₂Cys)-[B] | ++++ |
| [Th]-*Lys*(Pam₂Cys-Ser-Ser)-[B] | ++++ |

Pam$_X$Cys $$R1-\underset{H}{N}-CH-COOH$$
$$\phantom{R1-N-}CH_2$$
$$\phantom{R1-N-}S$$
$$\phantom{R1-N-}CH_2$$
$$R2-O-CH$$
$$R3-O-CH_2$$

For Pam₃Cys, R1, R2 & R3 = H₃C(H₂C)₁₄CO

For Pam₂Cys, R1 = H, R2 & R3 = H₃C(H₂C)₁₄CO

FIGURE 1

HPLC Chromatogram

Lipopeptide

**P25-*Lys*-LHRH**

Mass Spectrum

Theoretical Mass: 3039.4    Determined Mass: 3038.9

HPLC Chromatogram

Lipopeptide

Pam$_2$Cys-Ser-Ser-P25-*Lys*-LHRH

Mass Spectrum

Theoretical Mass: 3867.54   Determined Mass: 3866.9

Lipopeptide

P25-*Lys*(Ste₂Cys-Ser-Ser)-LHRH

IMMUNOGENIC LIPOPEPTIDES COMPRISING T-HELPER AND B-CELL EPITOPES

CROSS REFERENCE TO RELATED APPLICATIONS

This application is a divisional application of U.S. application Ser. No. 10/525,301, filed Aug. 29, 2005 (under 35 U.S.C. §371), which is a National Stage of International Application No. PCT/AU2003/001018, filed 12 Aug. 2003 which claims the benefit of and priority to U.S. Provisional Application No. 60/402,838, filed 12 Aug. 2002, all of which are hereby incorporated in their entirety by reference.

FIELD OF THE INVENTION

The present invention relates generally to the field of immunology, and more particularly to reagents for generating antibody and/or cellular responses to a peptide immunogen, and methods for using said reagents for enhancing the immune response of a subject, or for the vaccination of a subject. Even more specifically, the present invention relates to novel lipopeptides having enhanced immunogenic activity, formulations and vaccine compositions comprising said lipopeptides, such as, for example, in combination with a pharmaceutically acceptable carrier or excipient, and to methods for making and using the formulations and vaccine compositions of the invention.

BACKGROUND TO THE INVENTION

1. General

This specification contains amino acid sequence information prepared using PatentIn Version 3.1, presented herein after the Abstract. Each sequence is identified in the sequence listing by the numeric indicator <210> followed by the sequence identifier (e.g. <210>1, <210>2, etc). The length of each sequence and source organism are indicated by information provided in the numeric indicator fields <211> and <213>, respectively. Sequences referred to in the specification are defined by the term "SEQ ID NO:", followed by the sequence identifier (e.g. SEQ ID NO: 1 refers to the sequence designated as <400>1). As used herein the term "derived from" shall be taken to indicate that a specified integer may be obtained from a particular source albeit not necessarily directly from that source.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific examples described herein. Functionally-equivalent products, compositions and methods are clearly within the scope of the invention, as described herein.

All the references cited in this application are specifically incorporated by reference herein.

The present invention is performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in the following texts that are incorporated by reference:

1. Sambrook, Fritsch & Maniatis, Molecular Cloning: A Laboratory Manual, Cold Spring Harbor Laboratories, New York, Second Edition (1989), whole of Vols I, II, and III;
2. DNA Cloning: A Practical Approach, Vols. I and II (D. N. Glover, ed., 1985), IRL Press, Oxford, whole of text;
3. Oligonucleotide Synthesis: A Practical Approach (M. J. Gait, ed., 1984) IRL Press, Oxford, whole of text, and particularly the papers therein by Gait, pp 1-22; Atkinson et al., pp 35-81; Sproat et al., pp 83-115; and Wu et al., pp 135-151;
4. Nucleic Acid Hybridization: A Practical Approach (B. D. Hames & S. J. Higgins, eds., 1985) IRL Press, Oxford, whole of text;
5. Animal Cell Culture: Practical Approach, Third Edition (John R. W. Masters, ed., 2000), ISBN 0199637970, whole of text;
6. Immobilized Cells and Enzymes: A Practical Approach (1986) IRL Press, Oxford, whole of text;
7. Perbal, B., A Practical Guide to Molecular Cloning (1984);
8. Methods In Enzymology (S. Colowick and N. Kaplan, eds., Academic Press, Inc.), whole of series;
9. J. F. Ramalho Ortigão, "The Chemistry of Peptide Synthesis" In: Knowledge database of Access to Virtual Laboratory website (Interactive, Germany);
10. Sakakibara, D., Teichman, J., Lien, E. Land Fenichel, R. L. (1976). *Biochem. Biophys. Res. Commun.* 73 336-342
11. Merrifield, R. B. (1963). *J. Am. Chem. Soc.* 85, 2149-2154.
12. Barany, G. and Merrifield, R. B. (1979) in *The Peptides* (Gross, E. and Meienhofer, J. eds.), vol. 2, pp. 1-284, Academic Press, New York.
13. Wünsch, E., ed. (1974) *Synthese von Peptiden in Houben-Weyls Methoden der Organischen Chemie* (Müler, E., ed.), vol. 15, 4th edn., Parts 1 and 2, Thieme, Stuttgart.
14. Bodanszky, M. (1984) *Principles of Peptide Synthesis*, Springer-Verlag, Heidelberg.
15. Bodanszky, M. & Bodanszky, A. (1984) *The Practice of Peptide Synthesis, Springer-Verlag*, Heidelberg.
16. Bodanszky, M. (1985) *Int. J. Peptide Protein Res.* 25, 449-474.
17. Handbook of Experimental Immunology, Vols. I-IV (D. M. Weir and C. C. Blackwell, eds., 1986, Blackwell Scientific Publications).

DESCRIPTION OF THE RELATED ART

Immunotherapy or vaccination are attractive for the prophylaxis or therapy of a wide range of disorders, such as, for example, certain infectious diseases, or cancers. However, the application and success of such treatments are limited in part by the poor immunogenicity of the target antigen. Many peptides, glycopeptides, lipids, lipopeptides, carbohydrates etc., are poorly immunogenic. Several techniques are used to enhance the immune response of a subject to a peptide immunogen.

It is known to utilize an adjuvant formulation that is extrinsic to the peptide immunogen (i.e. it is mixed with the immunogen prior to use), such as, for example, complete Freund's adjuvant (CFA), to enhance the immune response of a subject to a peptide immunogen. However, many of the adjuvants currently available are too toxic for use in humans, or simply ineffective. Moreover, adjuvants of this type require prior formulation with the peptide immunogen immediately before administration, such formulations often having a low solubility or being insoluble.

Lipopeptides, wherein a lipid moiety that is known to act as an adjuvant is covalently coupled to a peptide immunogen, may be capable of enhancing the immunogenicity of an otherwise weakly immunogenic peptide in the absence of an extrinsic adjuvant [Jung et al., Angew Chem, Int Ed Engl 10, 872, (1985); Martinon et al., J Immunol 149, 3416, (1992); Toyokuni et al., J Am Chem Soc 116, 395, (1994); Deprez, et al., J Med Chem 38, 459, (1995); and Sauzet et al., Vaccine 13, 1339, (1995); Benmohamed et al., Eur. J. Immunol. 27, 1242, (1997); Wiesmuller et al., Vaccine 7, 29, (1989); Nardin et al., Vaccine 16, 590, (1998); Benmohamed, et al. Vaccine 18, 2843, (2000); and Obert, et al., Vaccine 16, 161, (1998)]. Suitable lipopeptides show none of the harmful side effects associated with adjuvant formulations, and both antibody and cellular responses have been observed against lipopeptides.

Several different fatty acids are known for use in lipid moieties. Exemplary fatty acids include, but are not limited to, palmitoyl, myristoyl, stearoyl and decanoyl groups or, more generally, any $C_2$ to $C_{30}$ saturated, monounsaturated, or polyunsaturated fatty acyl group is thought to be useful.

The lipoamino acid N-palmitoyl-S-[2,3-bis(palmitoyloxy)propyl]cysteine, also known as $Pam_3Cys$ or $Pam_3Cys$-OH (Wiesmuller et al., Z. Physiol. Chem. 364 (1983), p593), is a synthetic version of the N-terminal moiety of Braun's lipoprotein that spans the inner and outer membranes of Gram negative bacteria. $Pam_3Cys$ has the structure of Formula (I):

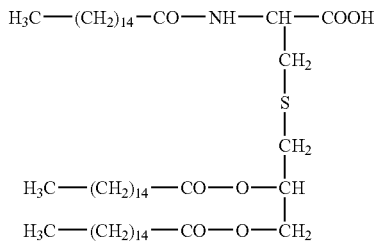

U.S. Pat. No. 5,700,910 to Metzger et al (Dec. 23, 1997) describes several N-acyl-S-(2-hydroxyalkyl)cysteines for use as intermediates in the preparation of lipopeptides that are used as synthetic adjuvants, B lymphocyte stimulants, macrophage stimulants, or synthetic vaccines. Metzger et al. also teach the use of such compounds as intermediates in the synthesis of $Pam_3Cys$-OH (Wiesmuller et al., Z. Physiol. Chem. 364, p593, 1983), and of lipopeptides that comprise this lipoamino acid or an analog thereof at the N-terminus.

$Pam_3Cys$ has been shown to be capable of stimulating virus-specific cytotoxic T lymphocyte (CTL) responses against influenza virus-infected cells (Deres et al., Nature 342, 561, 1989) and to elicit protective antibodies against foot-and-mouth disease (Wiesmuller et al., Vaccine 7, 29, 1989; U.S. Pat. No. 6,024,964 to Jung et al., Feb. 15, 2000) when coupled to the appropriate epitopes.

Recently, $Pam_2Cys$ (also known as dipalmitoyl-S-glyceryl-cysteine or S-[2,3-bis(palmitoyloxy)propyl]cysteine, an analogue of $Pam_3Cys$, has been synthesised (Metzger, J. W., A. G. Beck-Sickinger, M. Loleit, M. Eckert, W. G. Bessler, and G. Jung. 1995. J Pept Sci 1:184.) and been shown to correspond to the lipid moiety of MALP-2, a macrophage-activating lipopeptide isolated from mycoplasma (Sacht, G., A. Marten, U. Deiters, R. Sussmuth, G. Jung, E. Wingender, and P. F. Muhlradt. 1998. Eur J Immunol 28:4207: Muhlradt, P. F., M. Kiess, H. Meyer, R. Sussmuth, and G. Jung. 1998. Infect Immun 66:4804: Muhlradt, P. F., M. Kiess, H. Meyer, R. Sussmuth, and G. Jung. 1997. J Exp Med 185:1951). $Pam_2Cys$ has the structure of Formula (II):

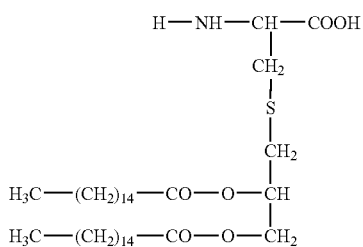

$Pam_2Cys$ is reported to be a more potent stimulator of splenocytes and macrophages than $Pam_3Cys$ (Metzger et al., J Pept. Sci 1, 184, 1995; Muhlradt et al., J Exp Med 185, 1951, 1997; and Muhlradt et al., Infect Immun 66, 4804, 1998).

Generation of an antibody response against a given antigen requires the generation of a strong T helper cell response. Accordingly, it is desirable to administer an antigen in conjunction with at least one T-helper cell epitope (Vitiello et al., J. Clin. Invest. 95, 341-349, 1995; Livingston et al., J. Immunol. 159, 1383-1392, 1997). However, because T helper cell responses are provided by $CD4^+$ T-cells that recognize fragments of peptide antigens in context of MHC class II molecules on the surface of antigen presenting cells (APCs), most of the processed forms of peptide antigens are only presented by one or a few alleles of MHC haplotypes. This causes the T helper response to a given antigenic peptide to be strictly under genetic control of an individual.

To avoid large genetic variation in the immune responses of a given population of individuals to an antigen, an antigen is administered in conjunction with a large protein having a range of T helper epitopes.

Alternatively, promiscuous or permissive T-helper epitope-containing peptides are administered in conjunction with the antigen. Promiscuous or permissive T-helper epitope-containing peptides are presented in the context of a vast majority of MHC class II haplotypes, such that they induce strong $CD4^+$ T helper responses in the majority of an outbred human population. Examples of promiscuous or permissive T-helper epitopes are tetanus toxoid peptide, Plasmodium falciparum pfg27, lactate dehydrogenase, and HIVgp120 (Contreas et al., Infect. Immun, 66, 3579-3590, 1998; Gaudebout et al., J. A.I.D.S. Human Retrovirol 14, 91-101, 1997; Kaumaya et al., J. Mol. Recog. 6, 81-94, 1993; and Fern and Good J. Immunol. 148, 907-913, 1992). Ghosh et al., Immunol 104, 58-66, 2001 and International Patent Application No. PCT/AU00/00070 (WO 00/46390) also describe T-helper epitopes from the fusion protein of Canine Distemper Virus (CDV-F). Certain promiscuous T-helper epitopes induce strong B cell responses to a given antigen, and can bypass certain haplotype restricted immune responses (Kaumaya et al., J. Mol. Recog. 6, 81-94, 1993).

Routinely, a vaccine preparation will comprise a mixture of polypeptides comprising the T-helper cell epitope and antigenic epitope, however it is also known to administer a single polypeptide comprising both the T-helper epitope and the antigenic epitope (e.g. Ghosh and Jackson, *Int. Immunol.* 11, 1103, 1999).

SUMMARY OF THE INVENTION

In work leading up to the present invention, the inventors sought to produce highly immunogenic lipopeptides having a lipid moiety and a polypeptide moiety comprising both a T helper epitope and an antigenic B cell epitope against which an immune response is desired. The lipopeptides of the invention have the lipid moiety attached via the terminal side chain amino group of an internal lysine, or an internal lysine analog such as, for example, ornithine, diaminopropionic acid, or diaminobutyric acid, in the polypeptide moiety. This is distinct from the N-terminal attachments, or C-terminal attachments (Grass-Masse et al. Vaccine, 14, 375, 1996), described previously.

Accordingly, by positioning said one or more lysine residue(s) or lysine analog residue(s) at predetermined locations within the polypeptide during peptide synthesis, the attachment site of the lipid is readily specified. Thus, the positioning of the lipid moiety in the lipopeptide is targeted to enhance the utility of the end-product for vaccine or adjuvant formulations.

Surprisingly, the inventors have found that attachment of the lipid moiety via the side-chain epsilon-amino group of an internal lysine residue or the terminal side-chain group of an internal lysine analog residue positioned between the amino acid sequences of the T helper epitope and the antigen, enhances the solubility of the lipopeptide product in many cases.

One advantage provided by the lipopeptides of the present invention is that they are sufficiently immunogenic such that it is generally not necessary to include an extrinsic adjuvant in vaccine formulations comprising these lipopeptides.

The present invention clearly encompasses the attachment of a lipid moiety via the epsilon-amino group of an internal lysine residue or the terminal side-chain group of an internal lysine analog residue present in the amino acid sequence of the T helper epitope or the antigen, the only requirement being that the lipid moiety is not attached to the N-terminus or the C-terminus of the peptide. As exemplified herein, the inventors have clearly shown that, for example, the lipid may be attached to the epsilon amino group of an internal lysine residue within the T-helper epitope without loss of the ability of the subject lipopeptides in generating an immune response, compared to a lipopeptide wherein the lipid is added to the epsilon amino group of a lysine positioned between the T-helper epitope and the B-cell epitope.

By "internal" means at a location other than the N-terminus or the C-terminus of a polypeptide comprising a T helper epitope and antigenic B cell epitope.

Preferably, the lipid moiety is attached to the peptide moiety via the epsilon amino group of a lysine residue or the terminal side-chain group of an internal lysine analog residue positioned between the amino acid sequences of the T helper epitope and the antigenic B cell epitope As will be known to the skilled person, solubility of an antigen is highly desirable for producing vaccine formulations on a commercial basis. In this respect, the inventors have found that the most effective lipopeptides of the invention are highly soluble. The relative ability of the lipopeptides of the invention to induce an antibody response in the absence of external adjuvant was reflected by their ability to upregulate the surface expression of MHC class II molecules on immature dendritic cells (DC).

As exemplified herein, the structure of the lipid moiety is not essential to activity of the resulting lipopeptide, as lipid moieties comprising palmitic acid, lauric acid, stearic acid or octanoic acid can be used without loss of immunogenicity. Accordingly, the present invention is not to be limited by the structure of the lipid moiety, unless specified otherwise, or the context requires otherwise.

Similarly, the addition of multiple lipid moieties to the peptide moiety, although generally not required, is also encompassed by the invention, unless specified otherwise or the context requires otherwise. As exemplified herein, the addition of multiple lipid moieties to the peptide moiety, such as, for example, to a position within the T-helper epitope, and to a position between the T-helper epitope and the B-cell epitope, does not adversely affect the ability of the lipopeptide to stimulate IgG production compared to a peptide having only a single lipid moiety attached.

It will be apparent from the preceding that the polypeptide is synthesized conveniently as a single amino acid chain, thereby requiring no post-synthesis modification to incorporate both epitopes.

Optionally, an amino acid spacer is added at either side of the internal lysine or lysine analog to which the lipid moiety is to be attached, such as, for example, between the T-helper and B-cell epitopes.

As exemplified herein, the present inventors produced the lipopeptide of the invention by coupling the lipid moiety to an exposed epsilon-amino group of an internal lysine residue positioned between the T-helper and B-cell epitopes in the synthetic peptide moiety, with or without a spacer. Particularly preferred spacers in this context consist of serine dimers, trimers, teramers, etc.

A spacer of any conventional type can also be added between the lipid moiety and the polypeptide moiety. Particularly preferred spacers in this context consist of arginine or serine dimers, trimers, teramers, etc. Alternatively, a 6-aminohexanoic acid spacer can be used.

Alternative spacers are also contemplated. For example, a spacer may be added to the exposed epsilon amino group of an internal lysine or to the terminal side-chain group of an internal lysine analog before addition of the lipid moiety.

Alternatively, a lipoamino acid of Formula (III) or (IV) may be added directly to the epsilon amino group of the internal lysine residue or to the terminal side-chain group of the internal lysine analog.

Also exemplified herein, the lipopeptide of the present invention induces the production of a high titer antibody against the B cell epitope moiety when administered to an animal subject, without any requirement for an adjuvant to achieve a similar antibody titer. This utility is supported by the enhanced maturation of dendritic cells following administration of the subject lipopeptides (i.e. enhanced antigen presentation compared to lipopeptides having N-terminally coupled lipid).

Also exemplified herein, a lipopeptide of the present invention comprising an antigenic B cell epitope of LHRH is capable of inducing infertility in a mouse model representative of other mammals in which infertility is to be induced. The sustained production of antibodies against LHRH achieved by the lipopeptides of the invention demonstrates the general utility of the subject lipopeptides in inducing humoral immunity and as an active agent in a vaccine preparation.

Also exemplified herein, a lipopeptide of the present invention comprising an antigenic B cell epitope of the M protein of Group A *Streptococcus* (herein "GAS") is capable of inducing protection in a mouse model representative of humans and other mammals in which vaccination against GAS is indicated. The data provided herein indicate that the lipopeptides of the present invention are capable of inducing a sustained production of antibodies against GAS (both serum IgG, and salivary and fecal IgA), and the opsonization of GAS, and the survival of animals against a subsequent GAS challenge. These data demonstrate the general utility of the subject lipopeptides in inducing humoral immunity and as an active agent in a vaccine preparation against GAS.

Also exemplified herein, a lipopeptide of the present invention comprising an antigenic B cell epitope of gastrin ("pentagastrin") is capable of inducing the sustained production of antibodies against gastrin and/or cholecystekinin in a mouse model of other mammals in which inhibition of gastric acid secretion is indicated. The data provided herein demonstrate the general utility of the subject lipopeptides in inducing humoral immunity against gastrin and immunoneutralization of gastrin, to thereby block secretion of gastric acid, in an animal suffering from hypergastrinemia, Zollinger-Ellison syndrome, gastric ulceration or duodenal ulceration due to excessive and unregulated secretion of gastric acid, or to reduce or prevent the formation of gastrin-dependent tumours in the pancreas or duodenum (i.e. the prophylaxis and/or therapy of gastrinoma).

As will be clear to those skilled in the art, the nature of the T-helper and B cell epitopes is not critical in the context of the present invention. The novel approach of attaching the lipid moiety to the epsilon amino group of one or more internal lysine residues or lysine analogue residues within the polypeptide portion of the construct has broad application. Accordingly, based on the results presented herein, it will be understood that a wide range of T-helper and B cell epitopes can be used in the lipopeptide constructs.

In fact, the broad range of applications exemplified herein indicate the generality of the lipopeptides of the present invention in the prophylaxis and therapy of a number of different conditions in humans and other mammals in which the generation of an immune response against an antigenic B cell epitope is indicated. Accordingly, the present invention is not to be limited to the treatment of any specific condition, ailment or disease state.

BRIEF DESCRIPTION OF THE DRAWINGS

FIG. 1 is a representation of the structures of synthetic peptides and lipopeptides (left) and the relative solubilities of a sample of those peptides and lipopeptides in saline solution (right). Peptides were designated as follows:
(i) [Th] consisting of a CD4+ T-helper epitope from the light chain of influenza virus hemagglutinin (SEQ ID NO: 1) or peptide P25 from CDV-F (SEQ ID NO: 24);
(ii) [B] consisting of a B cell epitope consisting of residues 1-10 of LHRH (SEQ ID NO: 2) or residues 2-10 of LHRH (SEQ ID NO: 3) or residues 6-10 of LHRH (SEQ ID NO: 4), a B cell epitope of the M protein of Group A *Streptococcus* ("peptide J14"; SEQ ID NO: 101); or a B cell epitope of gastrin contained within the C-terminal 5 residues of gastrin (i.e., "pentagastrin"; SEQ ID NO: 102);
(iii) [Th]-[B] consisting of a polypeptide having (i) and (ii) (e.g., SEQ ID NOs: 5, 103, 104, 105, 107, 109 or 111); and
(iv) [Th]-Lys-[B] consisting of a polypeptide having (i) and (ii) separated by a lysine residue (e.g., SEQ ID NOs: 7, 9, 13, 106, 108, 110, or 112).

Lipopeptides were designated as follows:
(i) Pam$_3$Cys-[Th]-[B] consisting of a lipid of the Formula (I) conjugated to the N-terminus of peptide [Th]-[B] supra (i.e. to the N-terminus of, for example, any one of SEQ ID NOs: 5, 103, 104, 105, 107, 109 or 111);
(ii) Pam$_3$Cys-Ser-Ser-[Th]-[B] consisting of a lipoamino acid of the Formula (III) conjugated to the N-terminus of peptide [Th]-[B] supra (i.e. to the N-terminus of, for example, any one of SEQ ID NOs: 5, 103, 104, 105, 107, 109 or 111);
(iii) Pam$_2$Cys-[Th]-[B] consisting of a lipid of the Formula (II) conjugated to the N-terminus of peptide [Th]-[B] supra (i.e. to the N-terminus of, for example, any one of SEQ ID NOs: 5, 103, 104, 105, 107, 109 or 111);
(iv) Pam$_2$Cys-Ser-Ser-[Th]-[B] consisting of a lipid of the Formula (IV) conjugated to the N-terminus of peptide [Th]-[B] supra (i.e. to the N-terminus of, for example, any one of SEQ ID NOs: 5, 103, 104, 105, 107, 109 or 111);
(v) [Th]-Lys(Pam$_3$Cys)-[B] consisting of peptide [Th]-Lys-[B] (e.g., any one of SEQ ID NOs: 7, 9, 13, 106, 108, 110, or 112) and a lipid of the Formula (I) conjugated to the epsilon-amino group of the internal lysine (Lys) of said peptide;
(vi) [Th]-Lys(Pam$_2$Cys)-[B] consisting of peptide [Th]-Lys-[B] (e.g., any one of SEQ ID NOs: 7, 9, 13, 106, 108, 110, or 112) and a lipid of the Formula (II) conjugated to the epsilon-amino group of the internal lysine (Lys) of said peptide; and
(vii) [Th]-Lys(Pam$_2$Cys-Ser-Ser)-[B] consisting of peptide [Th]-Lys-[B] (e.g., any one of SEQ ID NOs: 7, 9, 13, 106, 108, 110, or 112) conjugated serially via the epsilon amino group of the internal lysine (Lys) to a serine homodimer (i.e. Ser-Ser) and then a lipid of the Formula (II). Thus, to produce this branched lipopeptide, the two serine residues were added to the epsilon-amino group of the lysine residue before the lipid moiety was attached.

Relative solubility of the peptides and lipopeptides based upon the influenza virus hemagglutinin T-helper epitope (SEQ ID NO: 1) and the LHRH 1-10 B-cell epitope (SEQ ID NO: 2) is indicated at the right of the figure, ranging from low solubility (−) to high solubility (++++).

Figure 2:
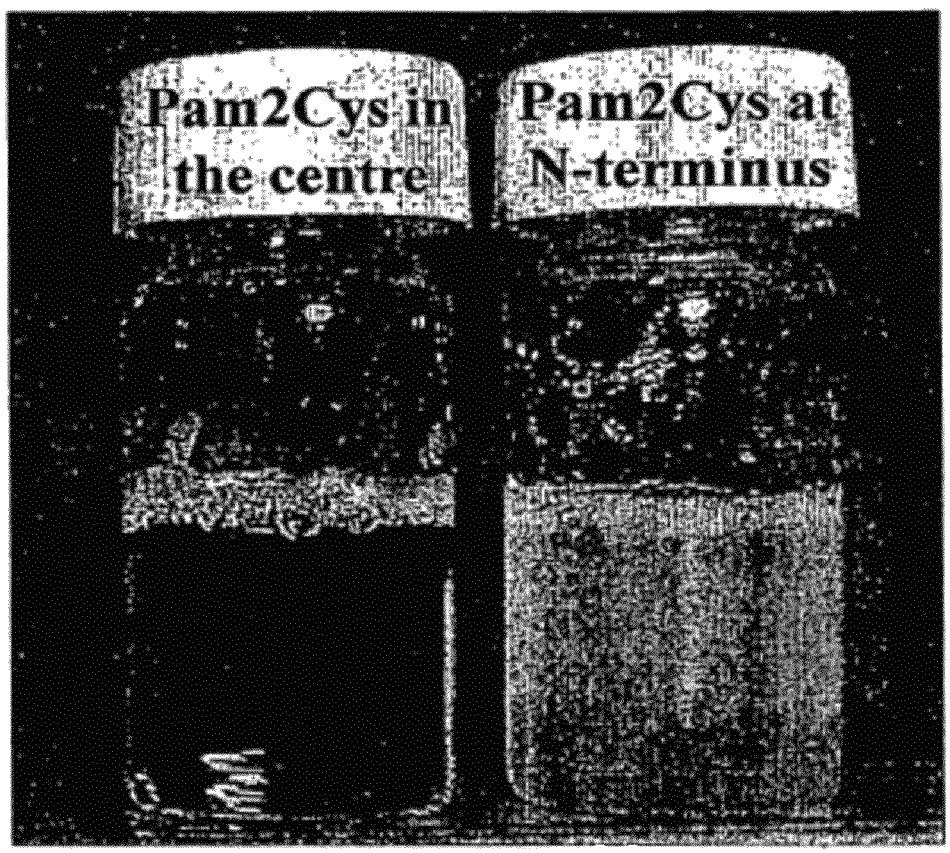

FIG. 2 is a photographic representation showing the solubilities of lipopeptides designated [Th]-Lys(Pam$_2$Cys-Ser-Ser)-[B] (left) and Pam$_2$Cys-Ser-Ser-[Th]-[B] (right) in FIG. 1, wherein the polypeptide moieties have the amino acid sequences set forth in SEQ ID NO: 7 and SEQ ID NO: 5, respectively. Both solutions are approximately 1 mg/ml lipopeptide in saline solution. The enhanced clarity of the solution comprising lipopeptide [Th]-Lys(Pam$_2$Cys-Ser-Ser)-[B] is indicative of its higher solubility compared to lipopeptide Pam$_2$Cys-Ser-Ser-[Th]-[B].

Figure 3:
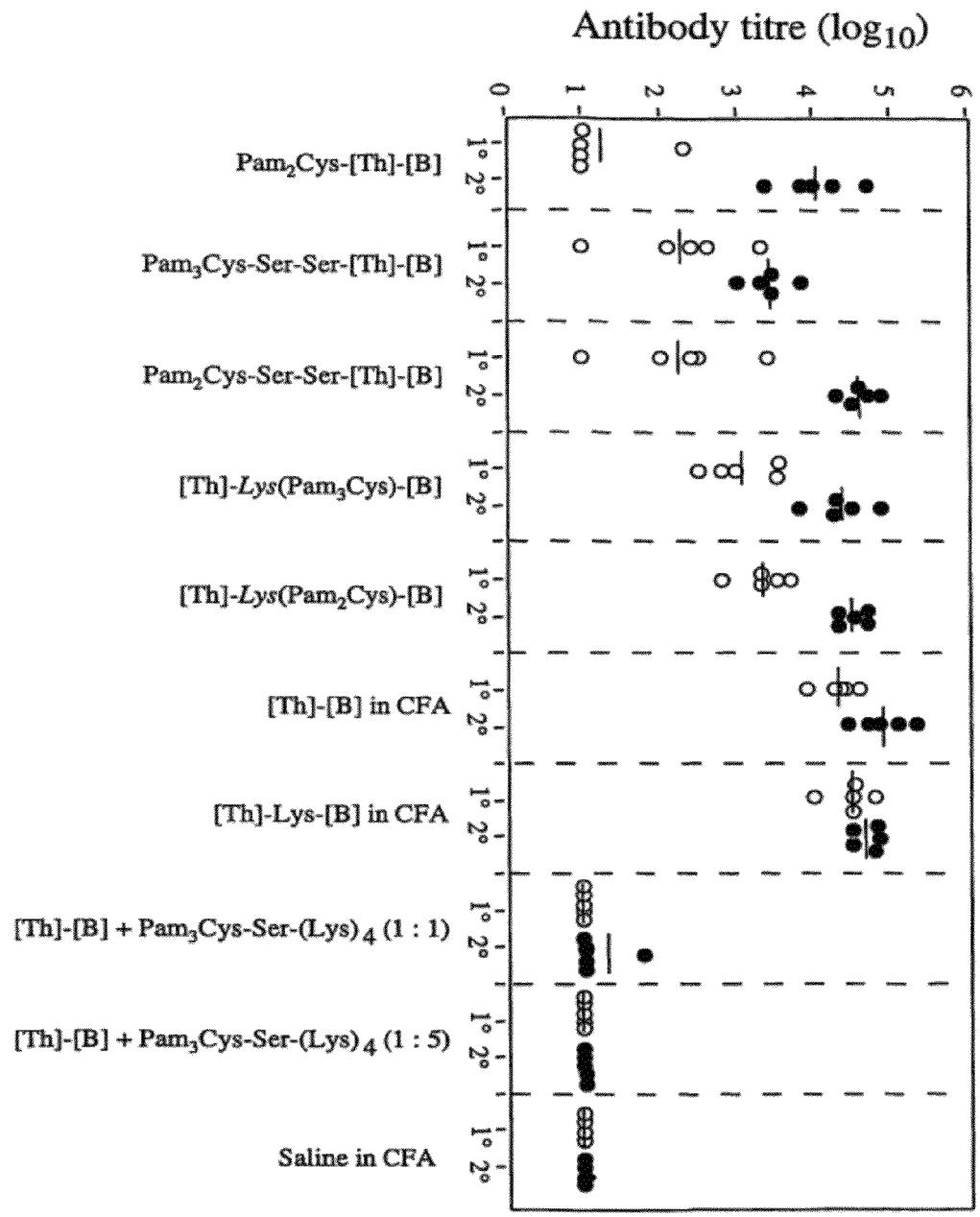

FIG. 3 is a graphical representation showing the anti-LHRH antibody titers obtained using each of the peptides and lipopeptides shown in FIG. 1, wherein the polypeptide moieties have the amino acid sequences set forth in SEQ ID NO: 5 or SEQ ID NO: 7. A negative control lipopeptide designated Pam$_3$Cys-Ser-Lys$_4$ (SEQ ID NO: 114) consisted of the lipid of Formula (I) conjugated to the N-terminus of a peptide having the amino acid sequence Ser-Lys-Lys-Lys-Lys (SEQ ID NO: 17): All peptides and lipopeptides were administered sub-cutaneously (s.c.) in saline for both primary inoculation (open circles) and secondary inoculations (closed circles). The two non-lipidated peptides [Th]-Lys-[B] and [Th]-[B] were administered in complete Freund's adjuvant (CFA) for the primary inoculations, and in incomplete Freund's adjuvant (IFA) for the secondary inoculations. For administration of the peptide [Th]-[B] in combination with the lipopeptide Pam$_3$Cys-S-Lys$_4$ (SEQ ID NO:114), peptide was dissolved in saline and mixed with the lipopeptide in 1:1 or 1:5 molar ratio as indicated. The dose of peptide and lipopeptide immunogens administered was 20 nmole. In all cases, control groups of animals received saline emulsified in CFA for priming and saline emulsified in IFA for the secondary inoculation.

Figure 4:
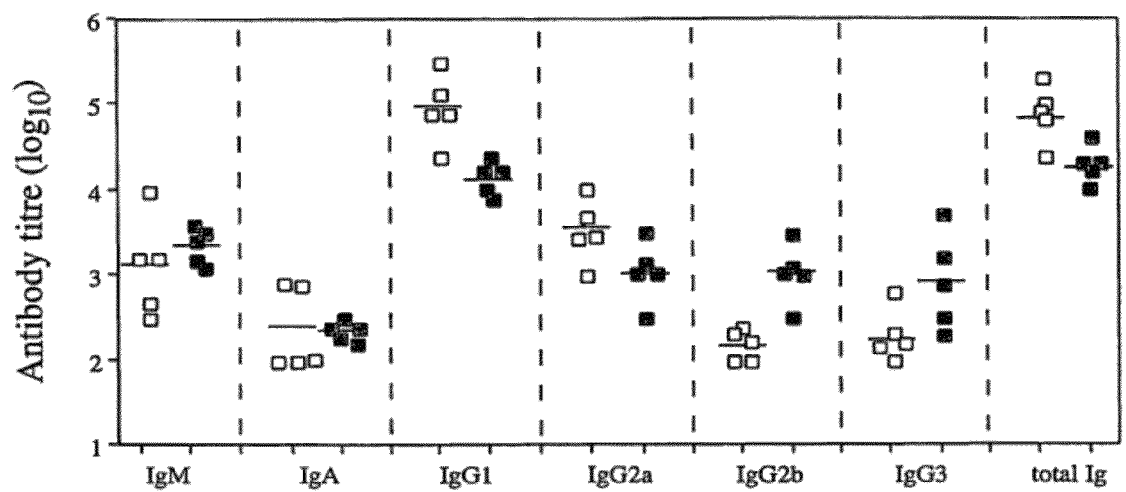

FIG. 4 is a graphical representation showing anti-LHRH antibody titers ($\log_{10}$) on the ordinate for each anti-LHRH antibody isotype (i.e. IgM, IgA, IgG1, IgG2a, IgG2b, IgG3, and total Ig) (abscissa) obtained or elicited during secondary antibody responses following inoculation with the lipopeptide [Th]-Lys(Pam$_2$Cys-Ser-Ser)-[B] (SEQ ID NO: 7). Mice were bled 2 weeks after receiving the second dose of the lipopeptide vaccine administered in saline either subcutaneously (open squares) or intranasally (closed squares) in saline.

Figure 5:
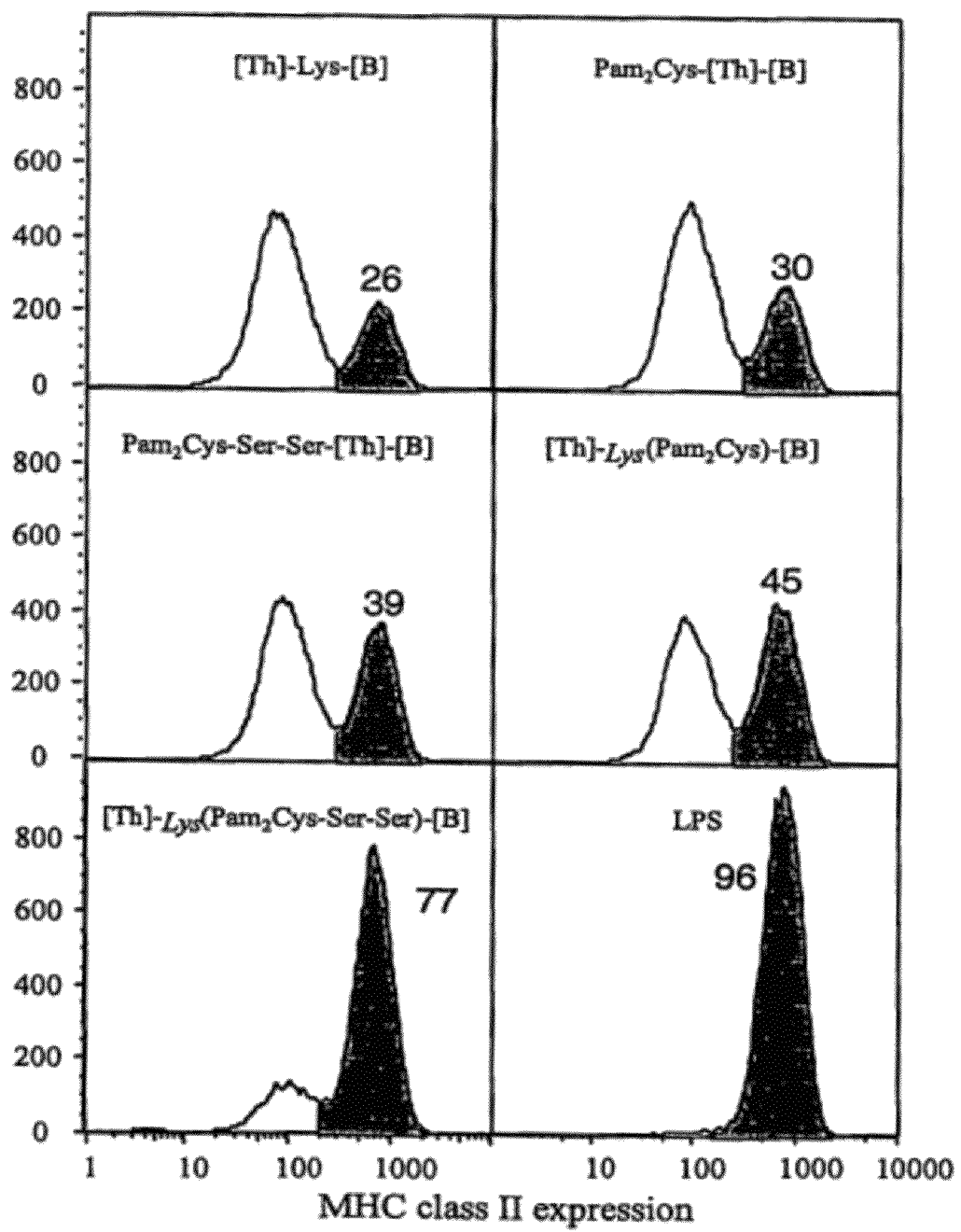

FIG. 5 is a graphical representation showing the relative abilities of peptides and lipopeptides shown in FIG. 1 (i.e. SEQ ID NO: 5 or SEQ ID NO: 7) to enhance the expression of MHC class II molecules on the surface of dendritic cells. Peptides and lipopeptides are indicated in each panel according to the nomenclature of FIG. 1. For each peptide or lipopeptide, $8 \times 10^4$ D1 cells were exposed to 4.5 fmole of peptide or lipopeptide and incubated overnight. The cells were collected and the MHC class II molecules expression was determined by flow cytometry after staining with FITC-conjugated anti-I-E$^{k,d}$ monoclonal antibody. About $3 \times 10^4$ D1 cells were analyzed for each sample. Data shown are for a representative of four independent experiments, and indicate enhanced staining with monoclonal antibody (i.e. enhanced D1 cell maturation) following administration of lipopeptides, particularly lipopeptide [Th]-Lys(Pam$_2$Cys-Ser-Ser)-[B] which induced a D1 maturation rate approaching the level observed for D1 cells challenged with lipopolysaccharide (LPS). Data obtained using the non-lipidated peptide [Th]-Lys-[B] are substantially the same as for D1 cells incubated in medium without any added peptide, lipopeptide or LPS, indicating a spontaneous maturation rate of about 26%.

Figure 6:
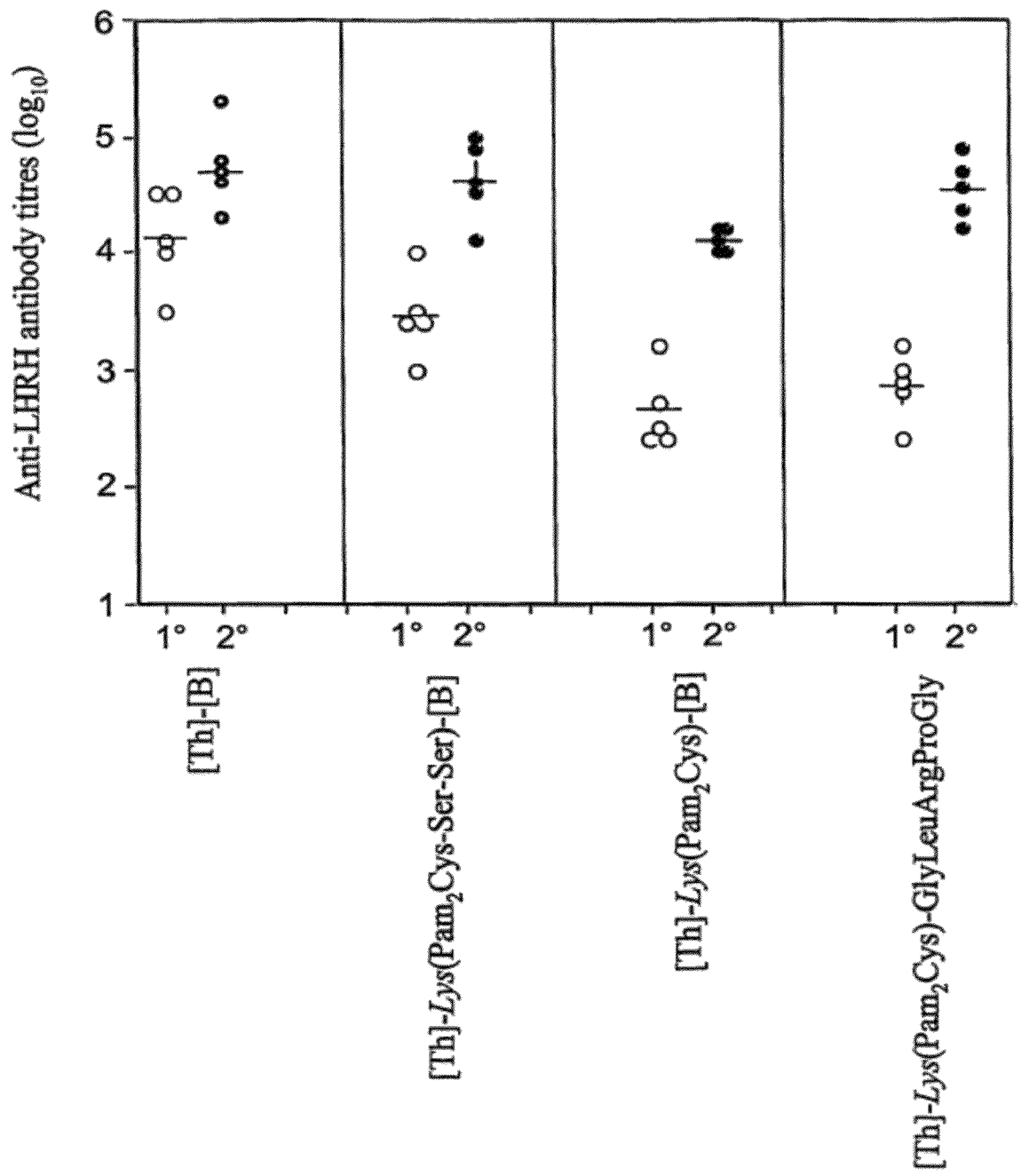
Figure 7A:
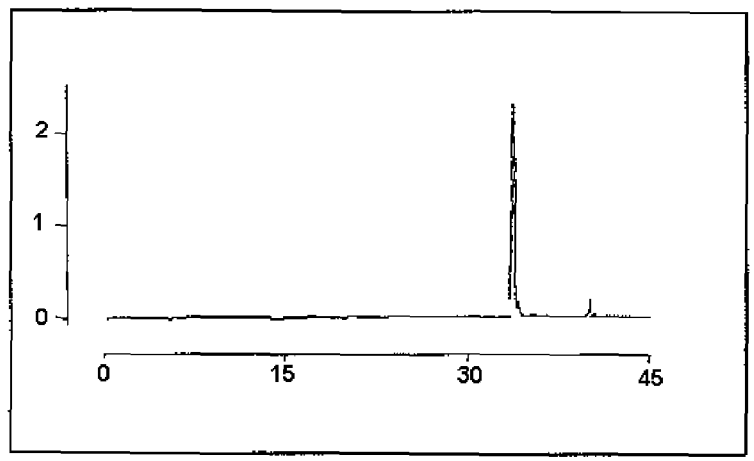
Figure 7A:
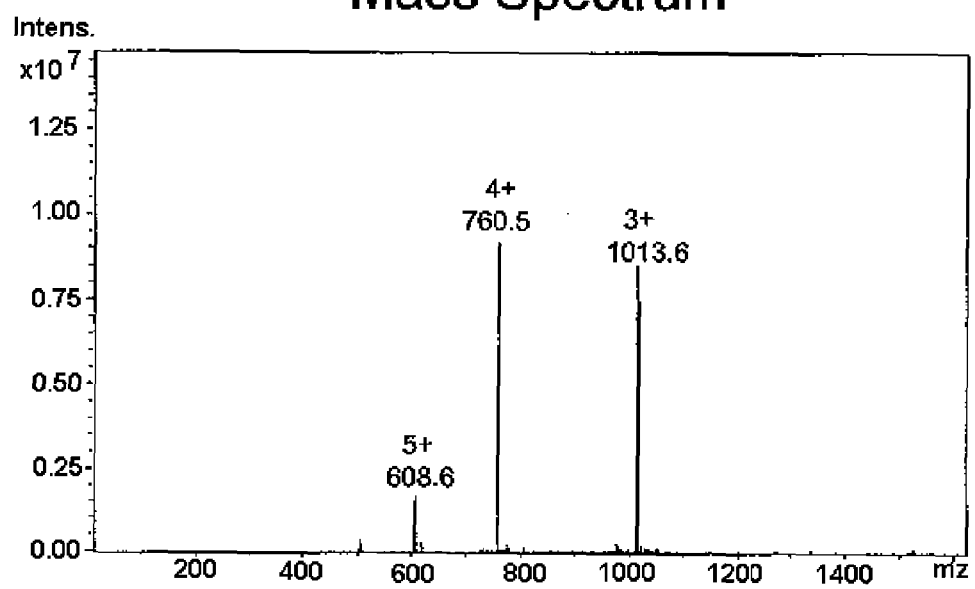
Figure 7B:
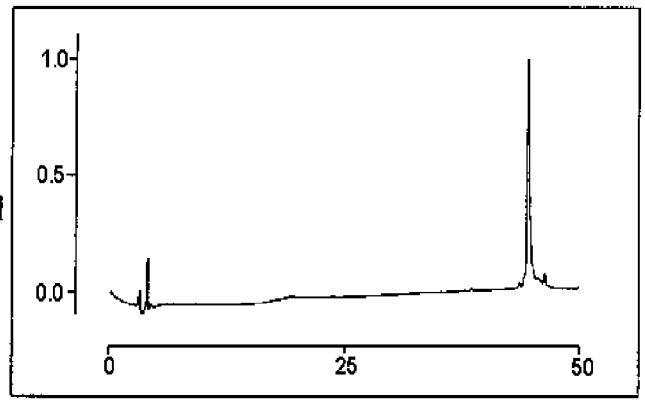
Figure 7B:
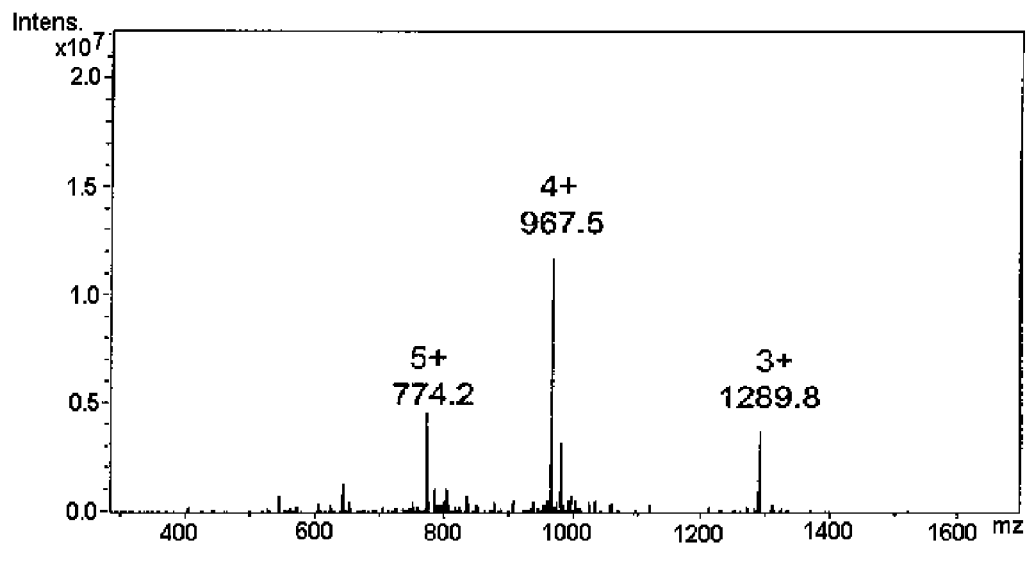
Figure 7C:
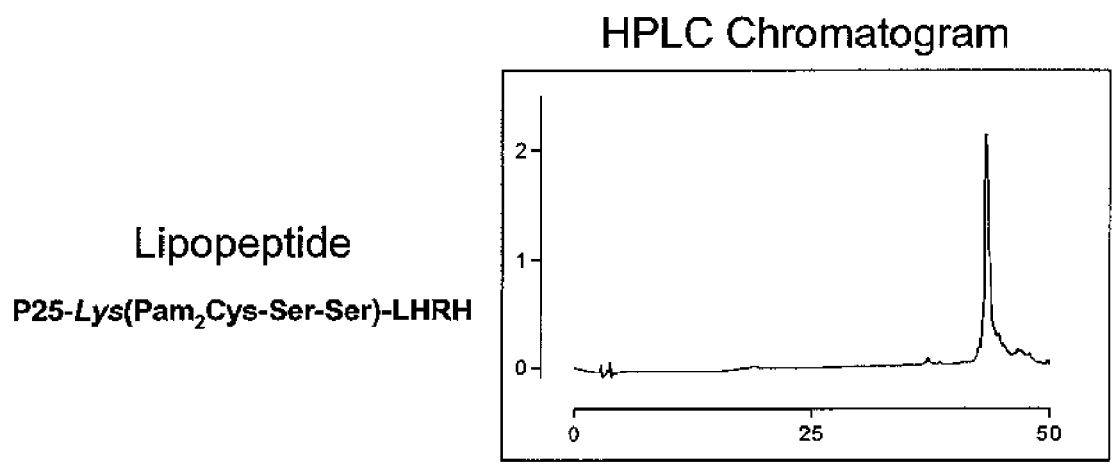
Figure 7C:
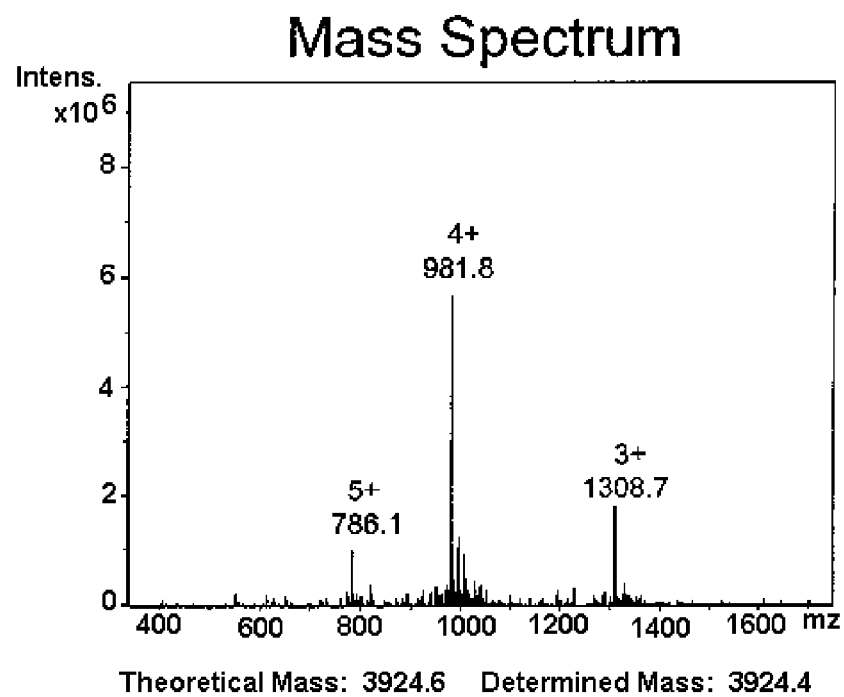
Figure 7D:
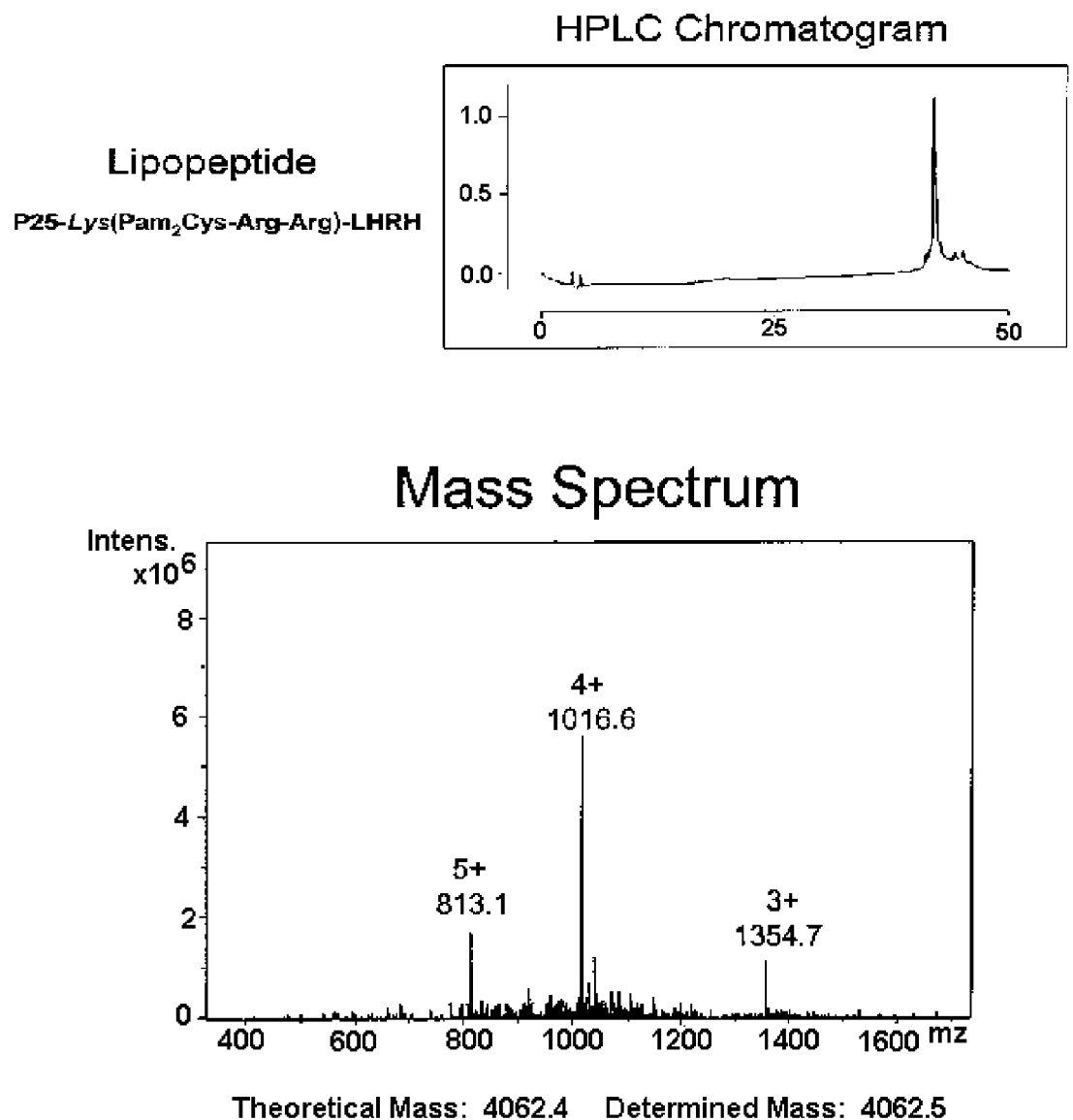
Figure 7E:
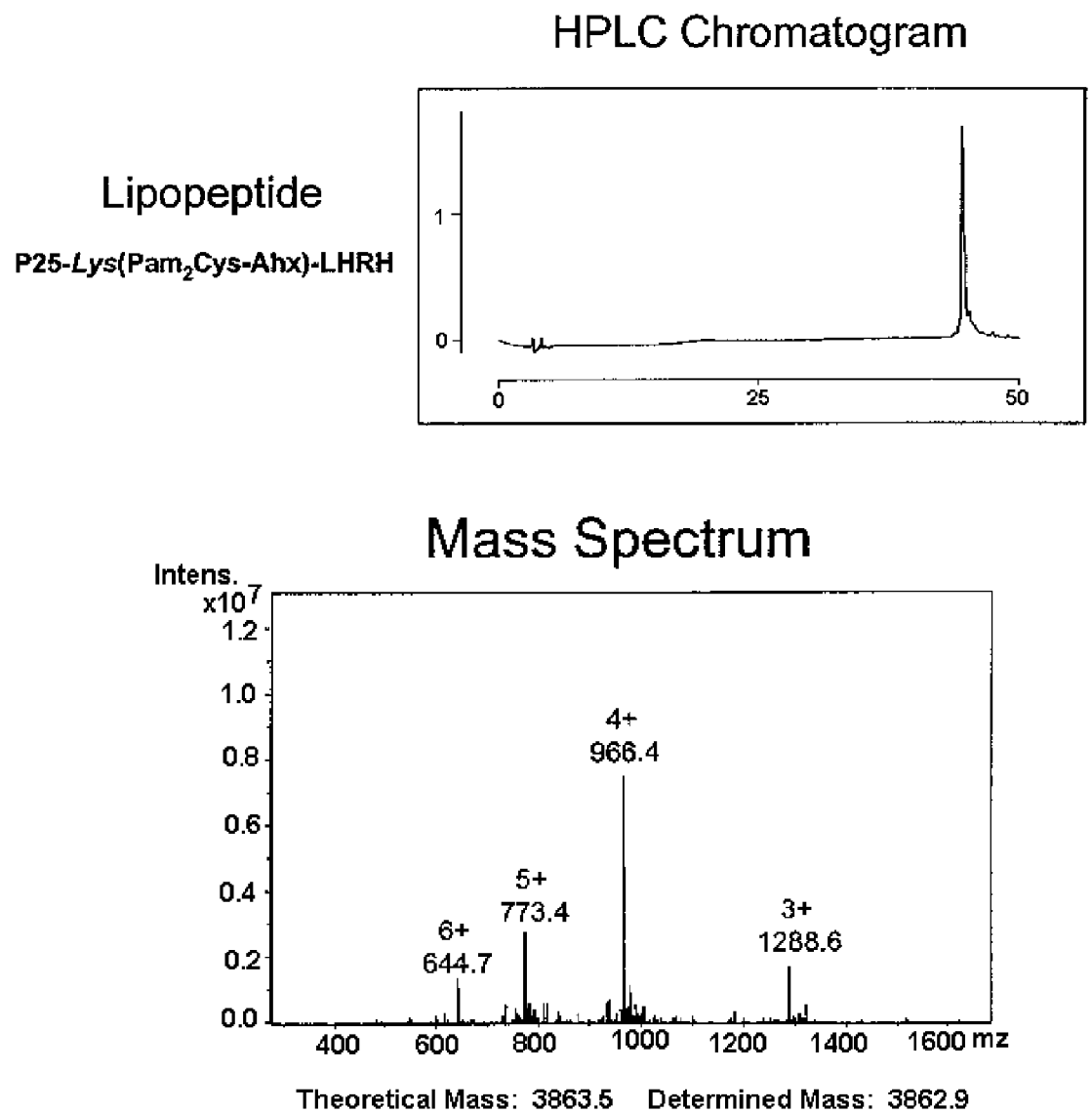
Figure 7F:
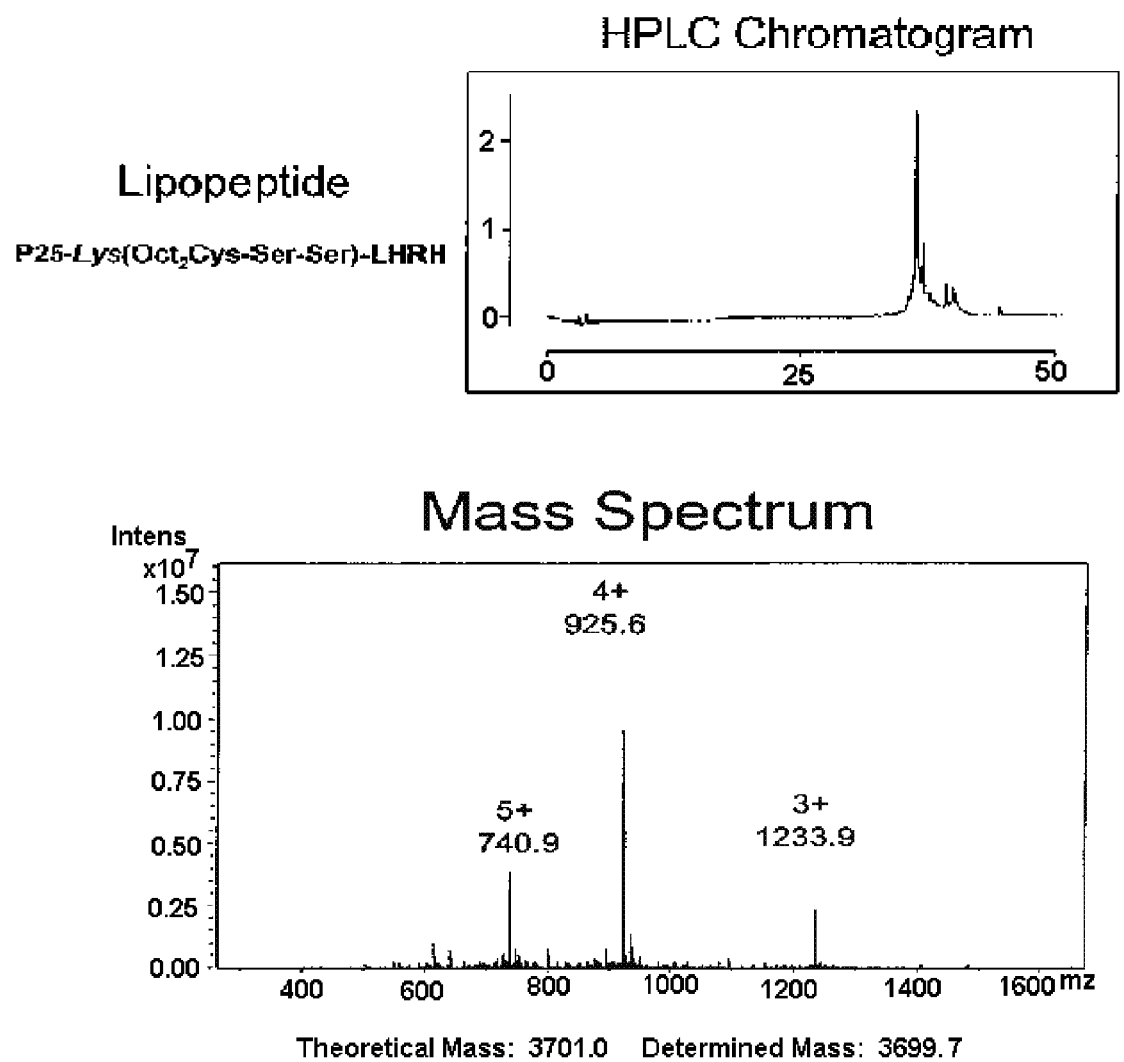
Figure 7G:
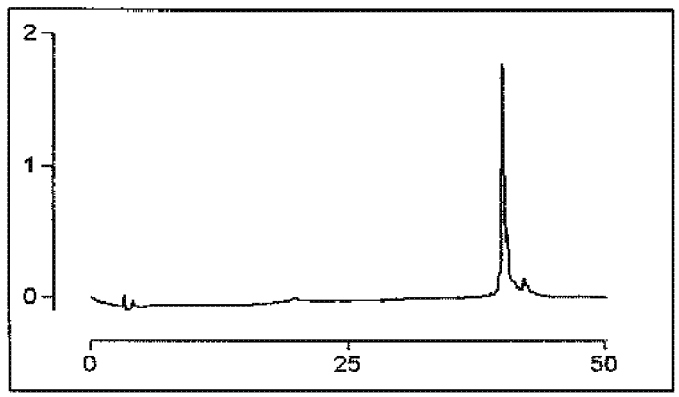
Figure 7G:
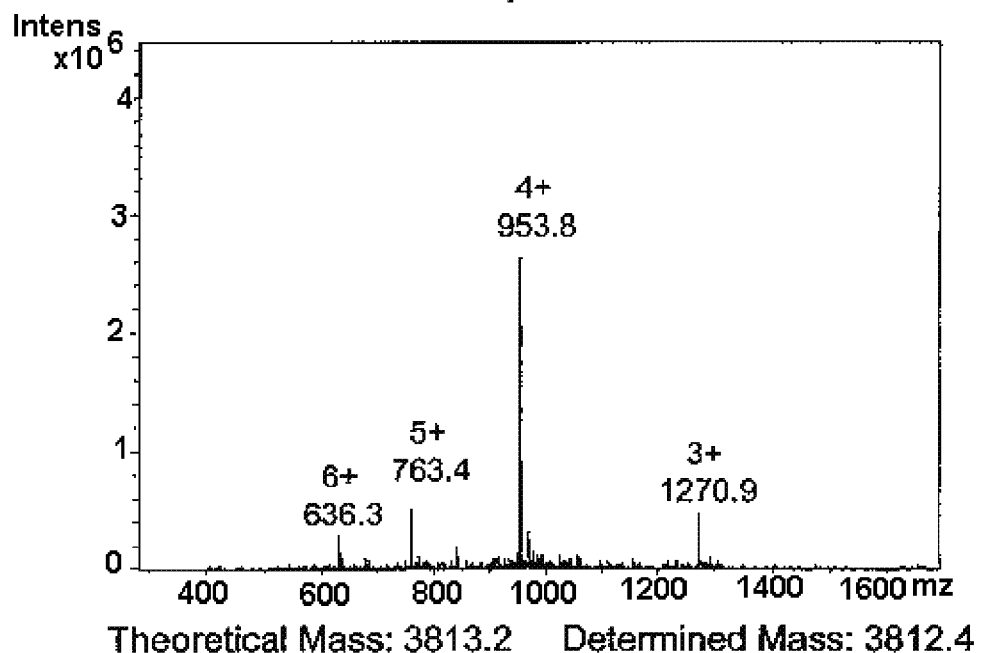
Figure 7H:
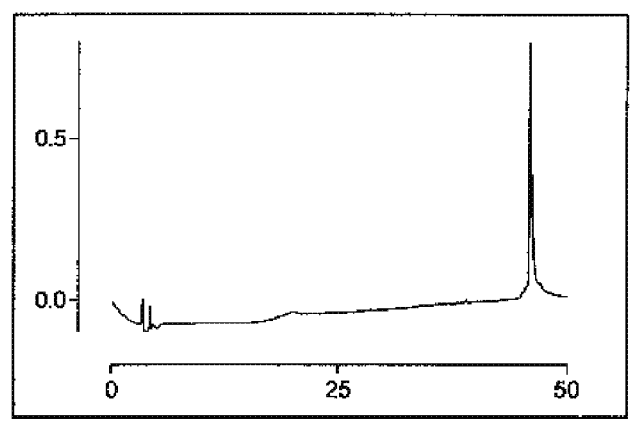
Figure 7H:
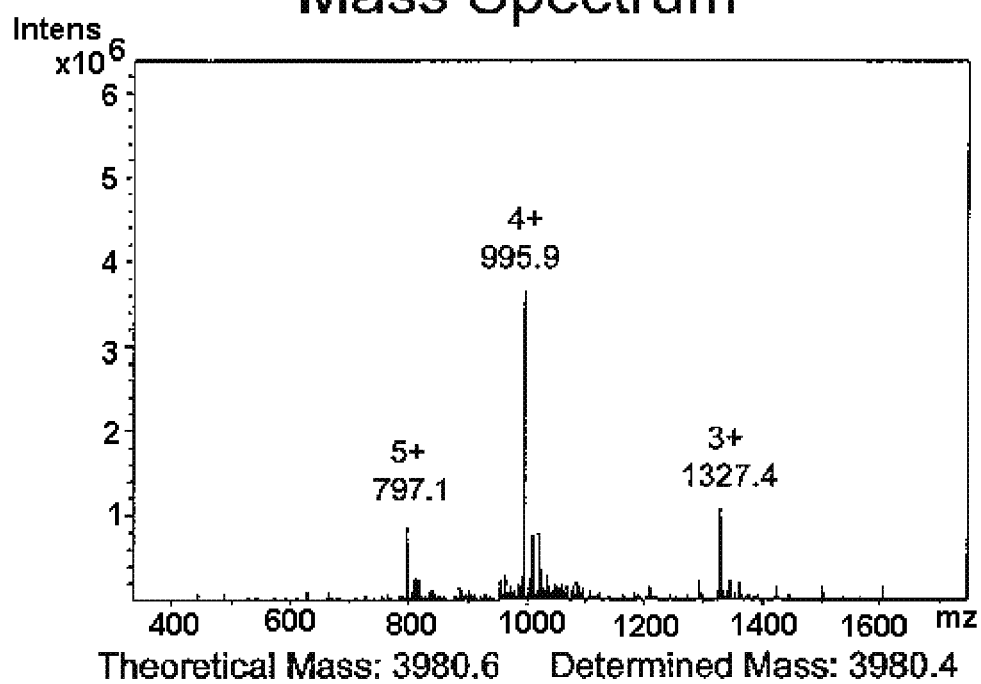

FIG. 6 is a graphical representation showing anti-LHRH antibody responses elicited by lipidated [Th]-Lys(Pam$_2$Cys)-[B] in which [Th] consists of CD4$^+$ T cell epitope from the light chain of influenza hemagglutinin (SEQ ID NO: 1) and [B] is LHRH 1-10 (SEQ ID NO: 2) or LHRH 6-10 (i.e. the C-terminal 5 residues of LHRH; SEQ ID NO: 4), with or without a serine spacer (Ser-Ser) positioned between the lipid and peptide moieties. Lipopeptide [Th]-Lys(Pam$_2$Cys)-GlyLeuArgProGly (SEQ ID NO: 115) is structurally similar to [Th]-Lys(Pam$_2$Cys)-[B], however this lipopeptide comprises SEQ ID NO: 4 in place of SEQ ID NO: 2.

FIG. 7 is a representation showing structural data, HPLC and mass spectra data for different lipopeptide constructs based on the T helper epitope P25 (SEQ ID NO: 24) and LHRH 2-10 (SEQ ID NO: 3), wherein the peptide moiety has the amino acid sequence set forth in SEQ ID NO: 9 and the lipid moiety is selected from the group consisting of: (i) Pam$_2$Cys; (ii) Ste$_2$Cys; (iii) Lau$_2$Cys; and (iv) Oct$_2$Cys. Different spacers were also positioned between the lipid moiety and the peptide moiety, as follows: (i) Ser-Ser, two serine residues; (ii) Arg-Arg, two arginine residues; and (iii) Ahx, 6-aminohexanoic acid. Structures of the lipopeptides are indicated in the left column; HPLC chromatograms for each lipopeptide are indicated in the middle column; and mass spectra are shown in the right column of the figure.

Figure 8:
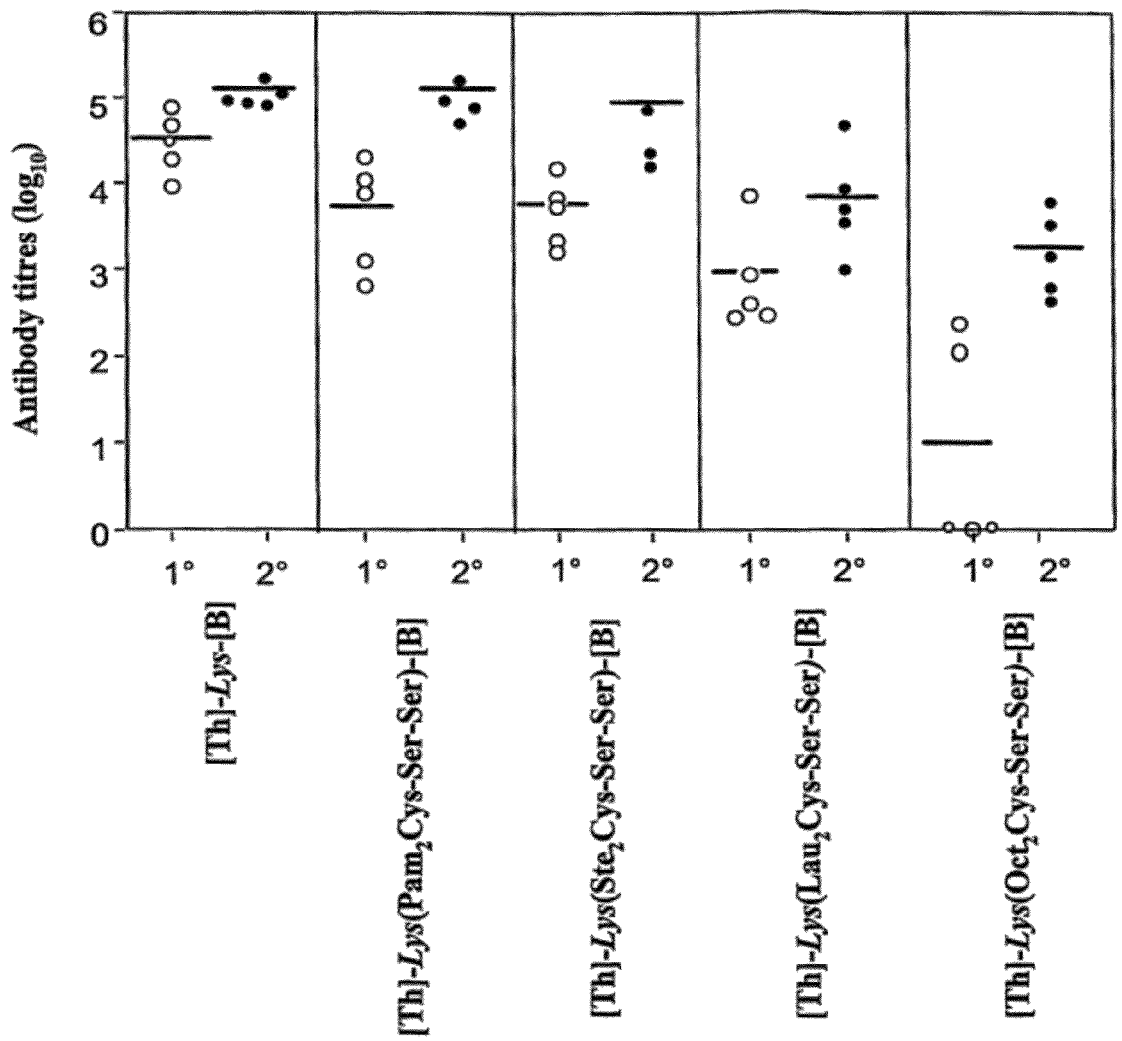

FIG. 8 is a graphical representation showing the immunogenicity of those lipopeptides indicated in the legend to FIG. 7 having a Ser-Ser spacer between the peptide and the lipid moiety and wherein the lipid moiety is selected from the group consisting of: (i) Pam$_2$Cys; (ii) Ste$_2$Cys; (iii) Lau$_2$Cys; and (iv) Oct$_2$Cys. Groups of BALB/c mice (6-8 weeks old) were inoculated subcutaneously with 20 nmoles of peptide immunogens for both primary and secondary vaccinations. All lipopeptides were administered in saline. The non lipidated peptide [Th]-Lys-[B] was administered in CFA as a control. Sera were obtained from blood taken at 4 weeks following the primary vaccination (open circles) and 2 weeks following the secondary vaccination (closed circles).

Figure 9:
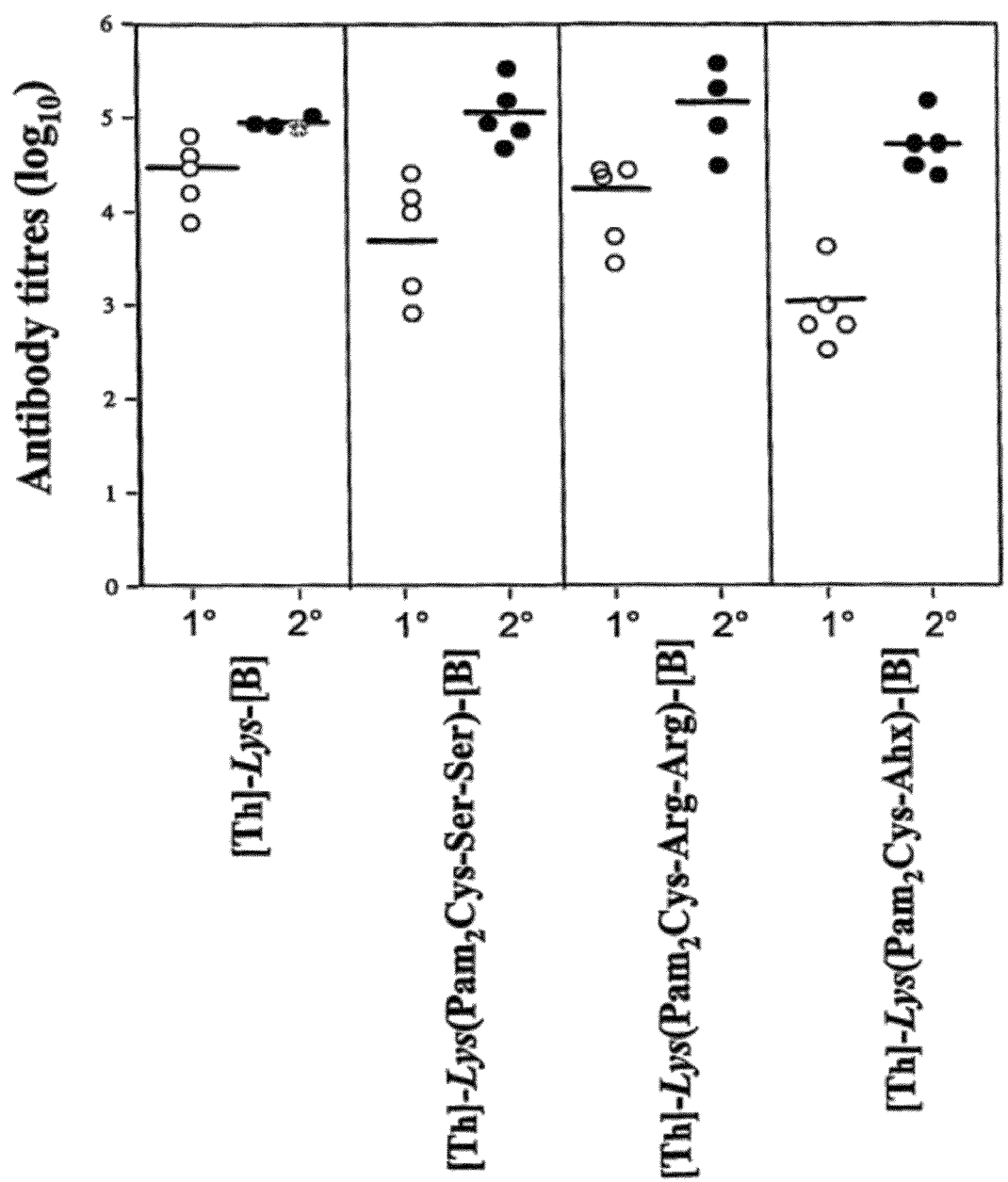

FIG. 9 is a graphical representation showing immunogenicity of lipopeptide immunogens from FIG. 7 having different spacers positioned between the lipid and peptide moieties, in particular spacers consisting of serine homodimers (Ser-Ser), arginine homodimers (Arg-Arg), or 6-aminohexanoic acid (Ahx). Groups of BALB/c mice (6-8 weeks old) were inoculated subcutaneously with 20 nmoles of peptide immunogens for both primary and secondary vaccinations. All lipopeptides were administered in saline. The non lipidated peptide [Th]-Lys-[B] was administered in CFA as a control. Sera were obtained from blood taken at 4 weeks following the primary vaccination (open circles) and 2 weeks following the secondary vaccination (closed circles).

Figure 10:
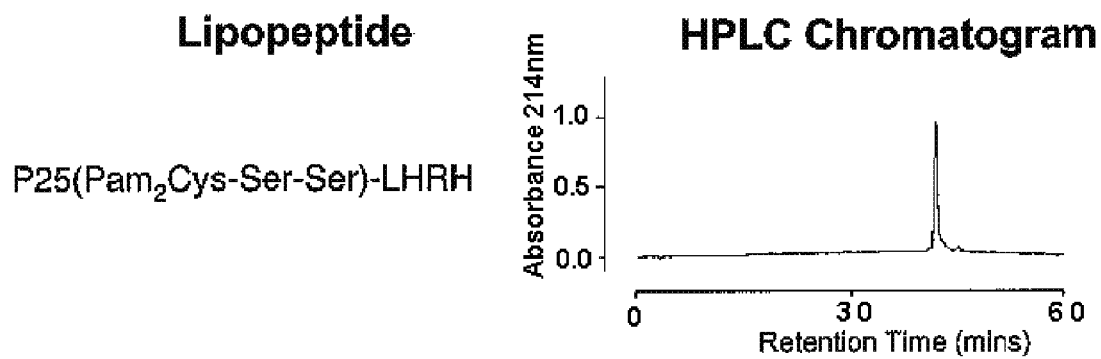
Figure 10:
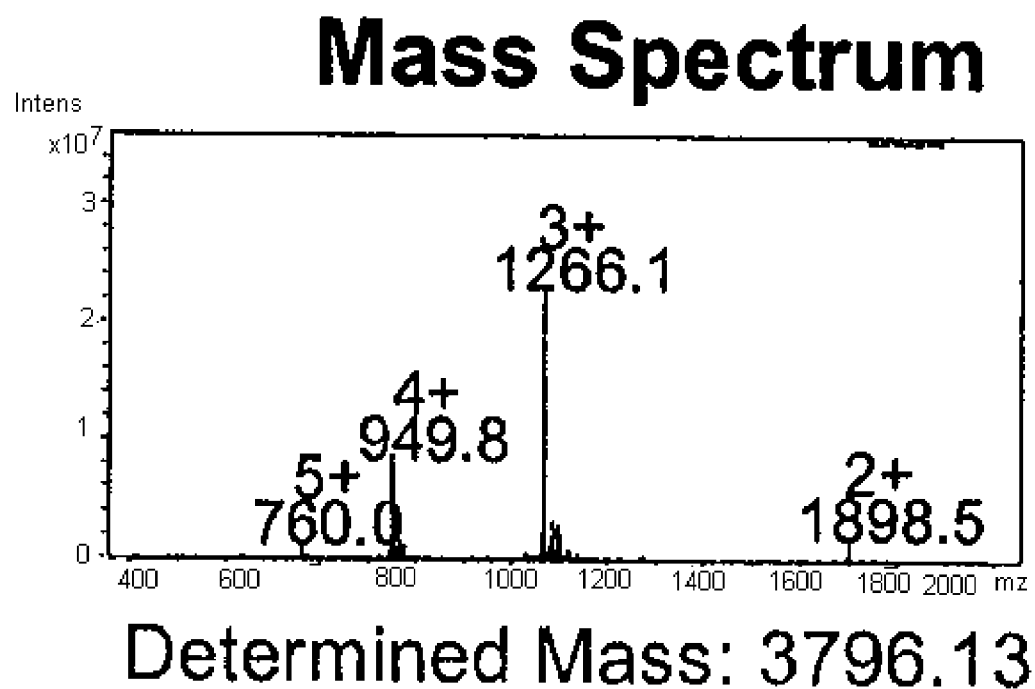

FIG. 10 is a graphical representation showing quality control data for a lipopeptide construct [Th](Pam$_2$Cys-Ser-Ser)-[B] in which the lipid moiety is pendant from the epsilon-amino group of an internal lysine residue (Lys-14) within the helper T cell epitope of the peptide set forth in SEQ ID NO: 103. The structures of the lipopeptide is indicated in the left column; an HPLC chromatogram for the lipopeptide is indicated in the middle column; and mass spectra data are shown in the right column of the figure.

Figure 11:
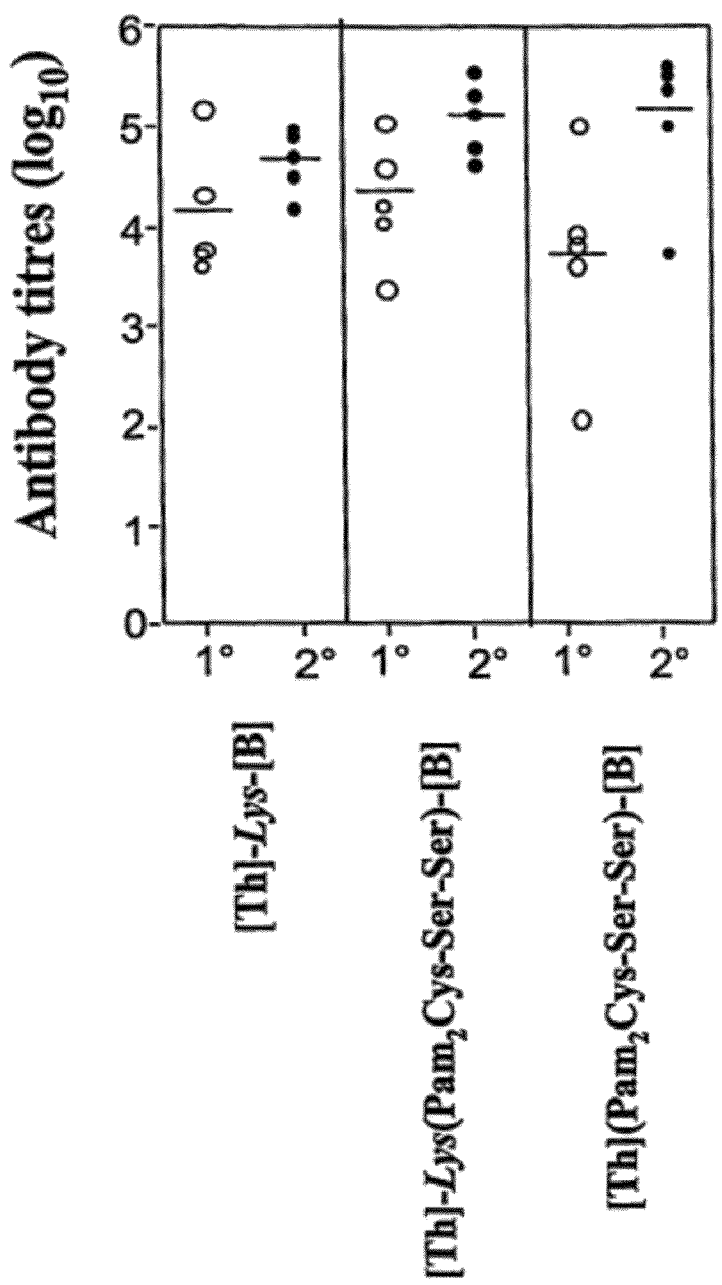

FIG. 11 is a graphical representation showing immunogenicity of the lipopeptide immunogen described in the legend to FIG. 10, compared to a lipopeptide immunogen having the lipid moiety added to an internal lysine residue positioned between the T-helper epitope and the B-cell epitope (i.e., the lipid moiety is added to the amino acid sequence set forth in SEQ ID NO: 9, Which differs from SEQ ID NO: 103 in having an internal lysine added between the T-helper and B-cell epitopes). A control non-lipidated peptide having the amino acid sequence set forth in SEQ ID NO: 9 (i.e., [Th]-Lys-[B]) was also used as a control. Groups of BALB/c mice (6-8 weeks old) were inoculated subcutaneously with 20 nmoles of peptide immunogens for both primary and secondary vaccinations. All lipopeptides were administered in saline. The non lipidated control peptide [Th]-Lys-[B] was administered in CFA. Sera were obtained from blood taken at 4 weeks following the primary vaccination (open circles) and 2 weeks following the secondary vaccination (closed circles). The lipopeptide construct [Th](Pam$_2$Cys-Ser-Ser)-[B] has the lipid moiety attached to the epsilon-amino group of a lysine residue (Lys-14) within the helper T cell epitope. The lipopeptide construct [Th]-Lys(Pam$_2$Cys-Ser-Ser)-[B] has the lipid attached to the epsilon-amino group of a lysine residue placed between the two peptide epitopes.

Figure 12:
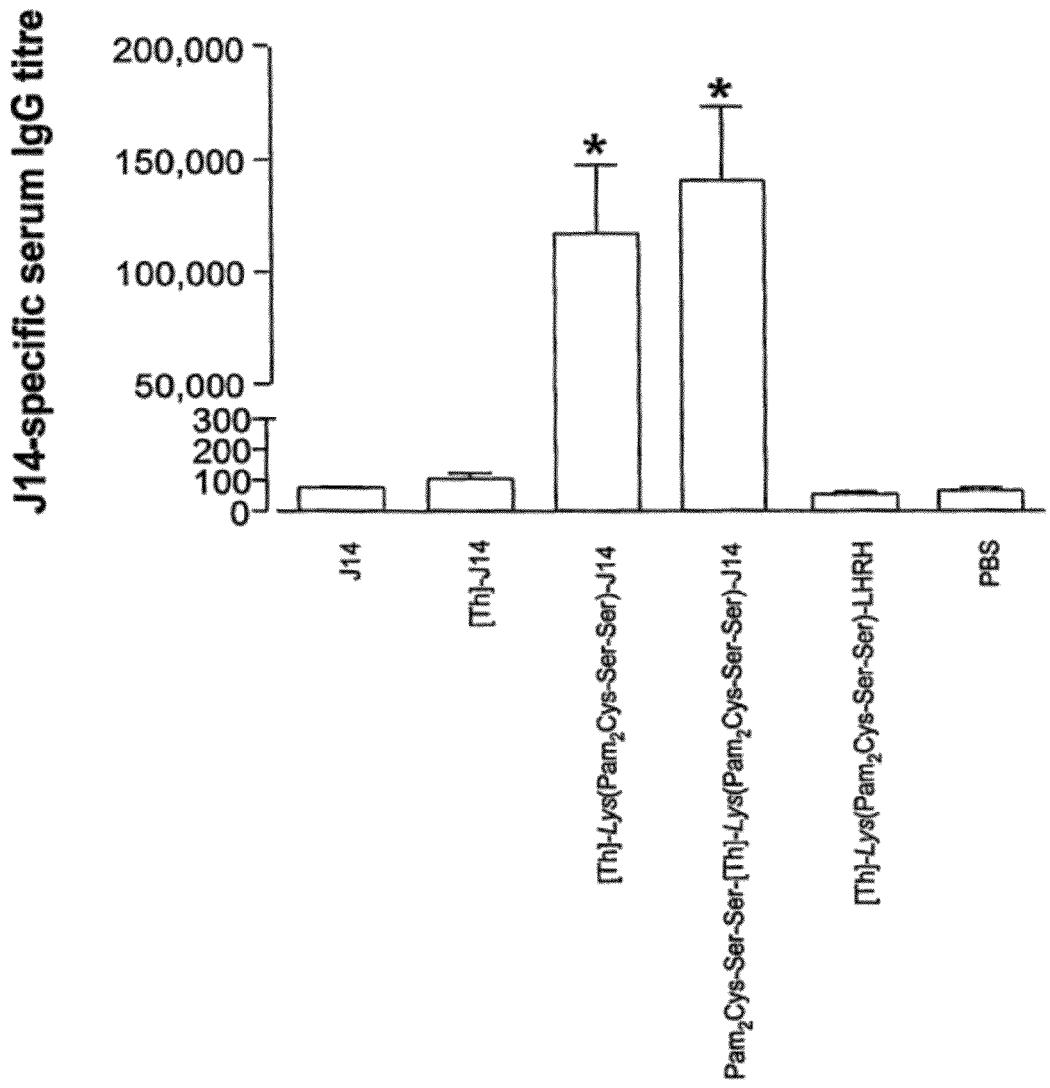

FIG. 12 is a graphical representation showing the ability of a lipopeptide comprising the T-helper epitope P25 (SEQ ID NO: 24) and a Group A *Streptococcus* B cell epitope ("J14"; SEQ ID NO: 101) and having the amino acid sequence of SEQ ID NO: 106, and one or two lipid moieties to elicit serum IgG in mice. The lipoamino acid moiety Pam$_2$Cys-Ser-Ser was added to an internal lysine positioned between the T-helper epitope and the B-cell epitope in all lipopeptides tested. In the lipopeptide [Th]-Lys(Pam$_2$Cys-Ser-Ser)-[J14], this is the only lipid moiety, whereas in the lipopeptide Pam$_2$Cys-Ser-Ser-[Th]-Lys(Pam$_2$Cys-Ser-Ser)-[J14], an additional lipoamino acid moiety Pam$_2$Cys-Ser-Ser was added to the N-terminal amino group of the T-helper epitope. Other immunogens were as follows: J14, non-lipidated peptide consisting of the J14 B-cell epitope-containing peptide (SEQ ID NO: 101); [Th]-[J14], a non-lipidated peptide consisting of the T-helper epitope (SEQ ID NO: 24) and the J14 peptide (SEQ ID NO: 101) and having the amino acid sequence of SEQ ID NO: 106; a lipidated peptide consisting of the T-helper epitope (SEQ ID NO: 24) and the LHRH B-cell epitope-containing peptide (SEQ ID NO: 3) and having the amino acid sequence of SEQ ID NO: 9; and phosphate-buffered saline (PBS). Female outbred Quackenbush mice 4-6 weeks old (15/group) were inoculated intranasally with 60 μg of peptide-based vaccine in a total volume of 30 μl PBS. Mice received three doses of vaccine at 21-day intervals. Seven days following the final dose mice were bled from the tail vein and J14-specific serum IgG was determined. Mice that received either J14-containing lipopeptides had significantly higher ($P<0.05$) serum IgG titres than did the control groups.

Figure 13:
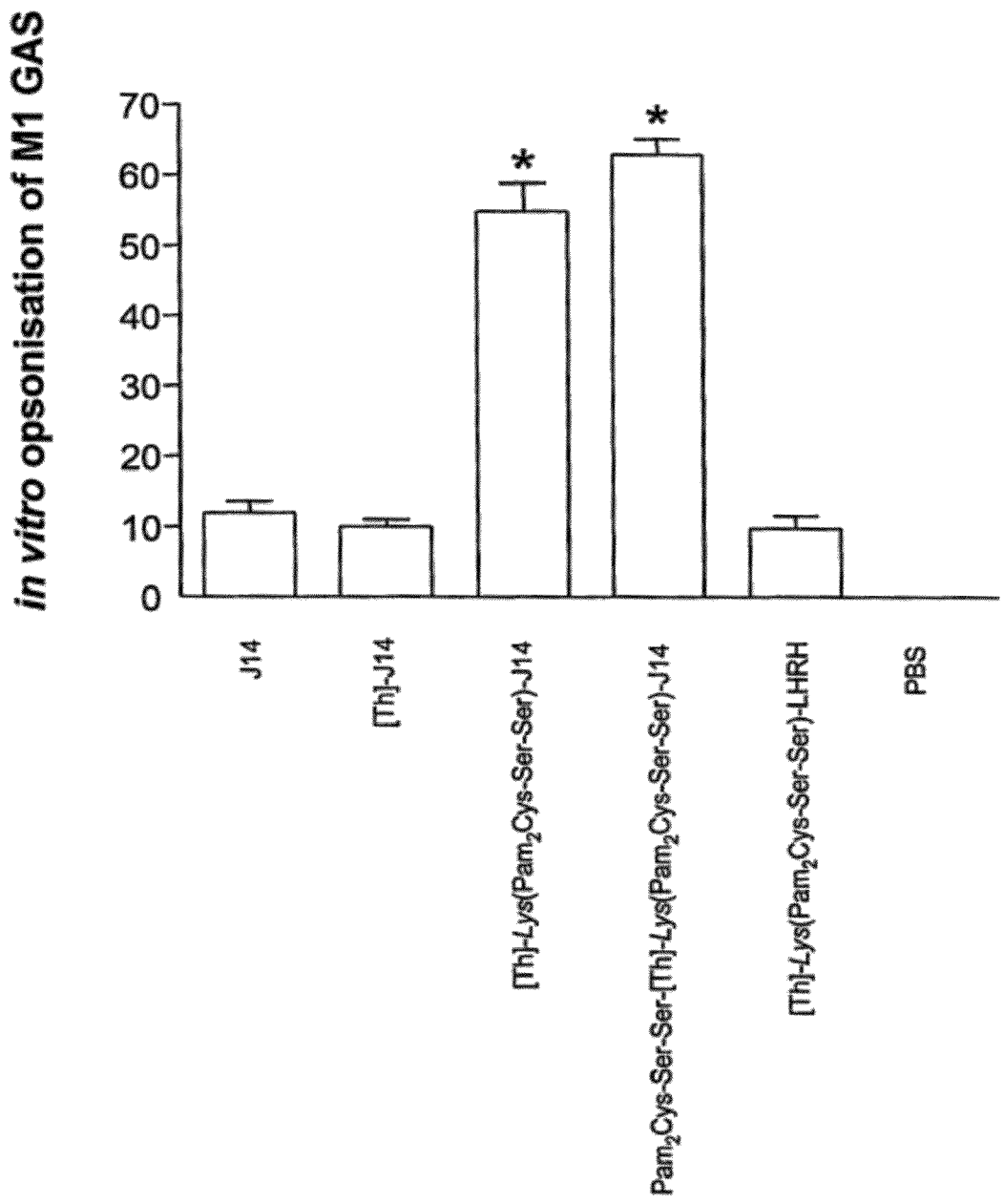

FIG. 13 is a graphical representation showing the opsonisation capability of antisera elicited by the non-lipidated peptides and lipopeptides indicated in the legend to FIG. 12. Female outbred Quackenbush mice 4-6 weeks old (15/group) were inoculated intranasally with 60 μg of peptide-based vaccine in a total volume of 30 μl PBS. Mice received three doses of vaccine at 21-day intervals. Indirect bacteriocidal assays were performed to determine the ability of sera from immunized mice to opsonise or "kill" the M1 GAS strain in vitro. Sera collected from mice immunized with either J14-containing lipopeptides were capable of significant ($P<0.05$) killing of GAS compared to sera collected from animals immunized with control peptides or lipopeptides or PBS.

Figure 14:
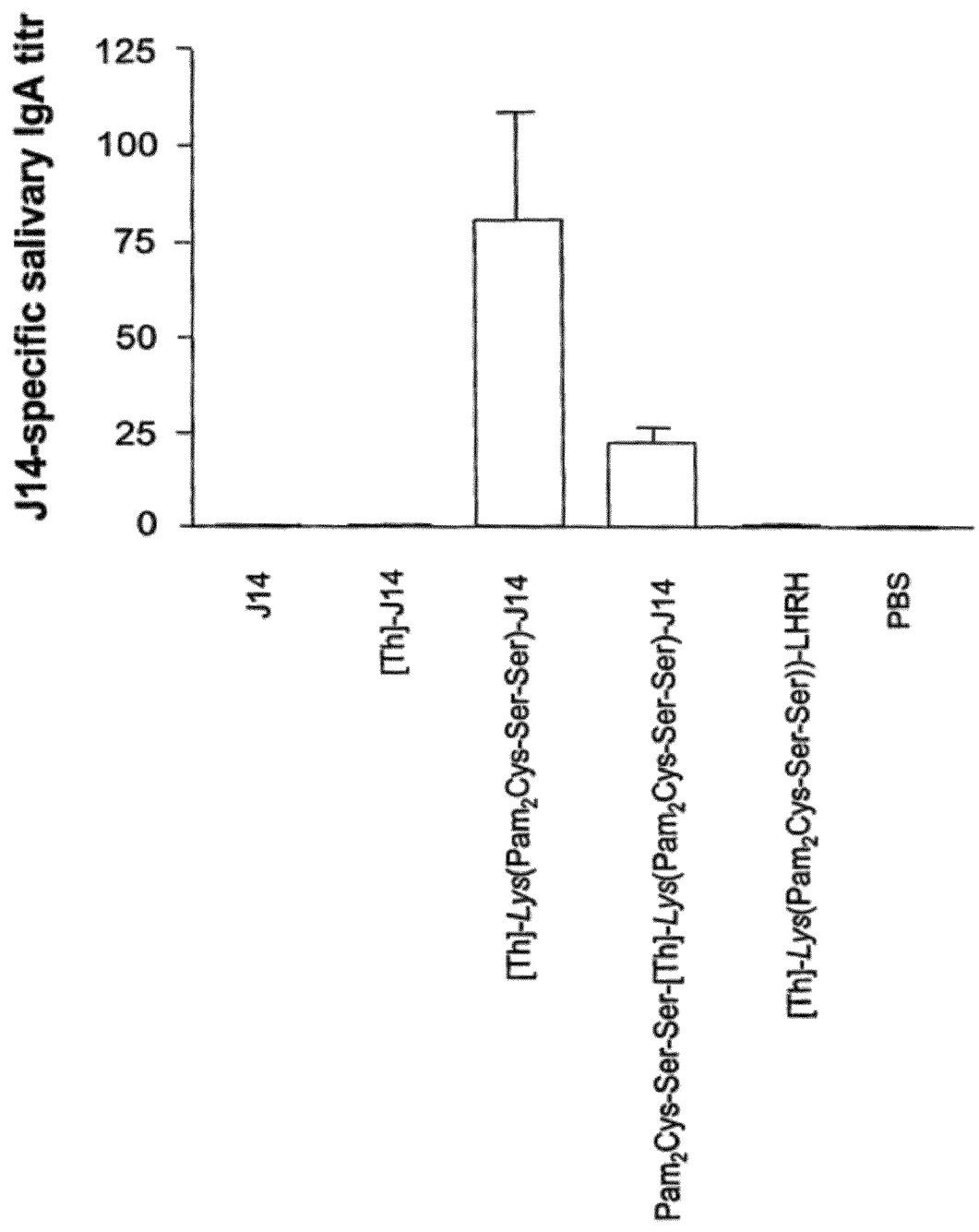

FIG. 14 is a graphical representation showing the ability of the non-lipidated peptides and lipopeptides indicated in the legend to FIG. 12 to elicit salivary IgA in mice. Female outbred Quackenbush mice 4-6 weeks old (15/group) were inoculated intranasally with 60 μg of each peptide-based vaccine in a total volume of 30 μl PBS. Mice received three doses of vaccine at 21-day intervals. Eight days following the final dose saliva was collected from individual mice and the average J14-specific salivary IgA antibody titres were determined by standard ELISA. The mice inoculated with either J14-containing lipopeptides had significantly ($P<0.05$) higher titres than the control groups that were immunized with control peptides or control lipopeptides or PBS.

Figure 15:
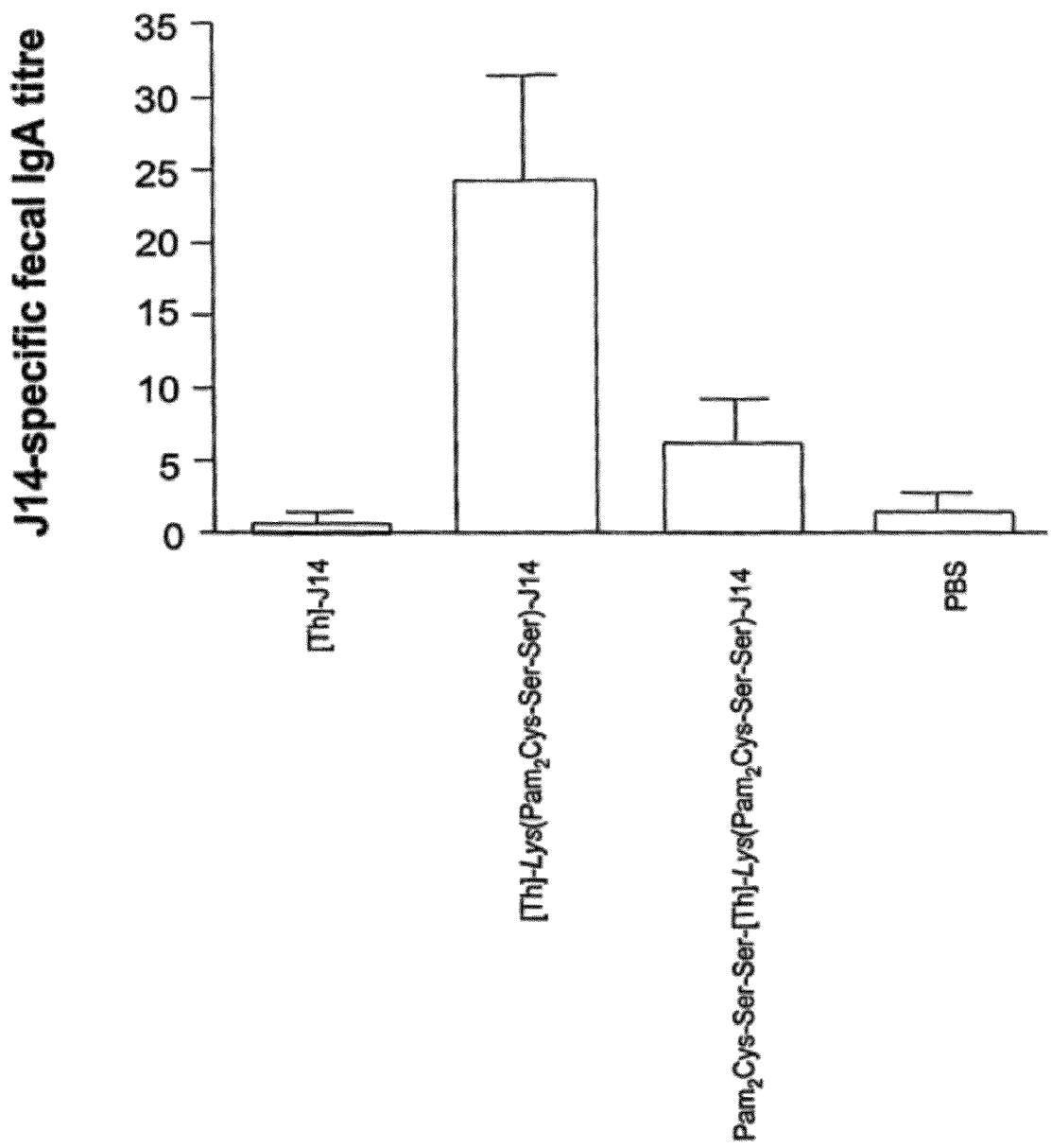

FIG. 15 is a graphical representation showing the ability of the non-lipidated J14-containing peptides and J14-containing lipopeptides indicated in the legend to FIG. 12 to elicit fecal IgA in mice. Female outbred Quackenbush mice 4-6 weeks old (15/group) were inoculated intranasally with 60 μg of peptide-based vaccine in a total volume of 30 μl PBS. Mice received three doses of vaccine at 21-day intervals. Fecal IgA was determined 6 days following the last dose of antigen. Only mice inoculated with mono-lipidated J14-containing peptide, wherein the lipid moiety was positioned between the T-helper epitope and the B-cell epitope (i.e., [Th]-Lys($Pam_2$Cys-Ser-Ser)-[J14]) had significant ($P<0.05$) fecal IgA titres.

Figure 16:
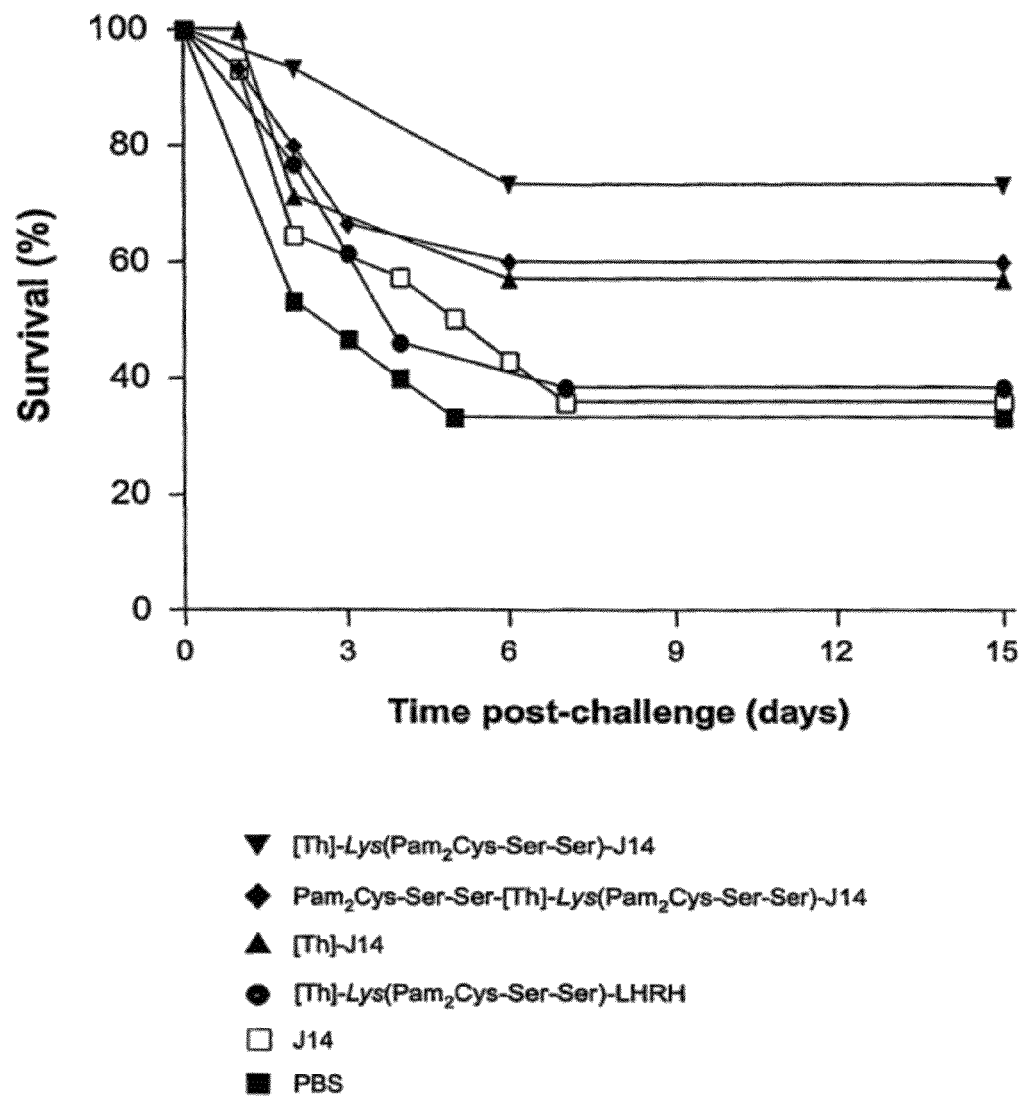

FIG. 16 is a graphical representation showing the ability of mice to survive challenge with bacteria following inoculation with the non-lipidated peptides and lipopeptides indicated in the legend to FIG. 12. Two weeks after the last dose of antigen, mice were challenged intranasally with M1 GAS strain and survival determined at various time points afterwards. Mice inoculated with mono-lipidated J14-containing peptide, wherein the lipid moiety was positioned between the T-helper epitope and the B-cell epitope (i.e., [Th]-Lys($Pam_2$Cys-Ser-Ser)-[J14]) demonstrated the best survival following challenge.

Figure 17:
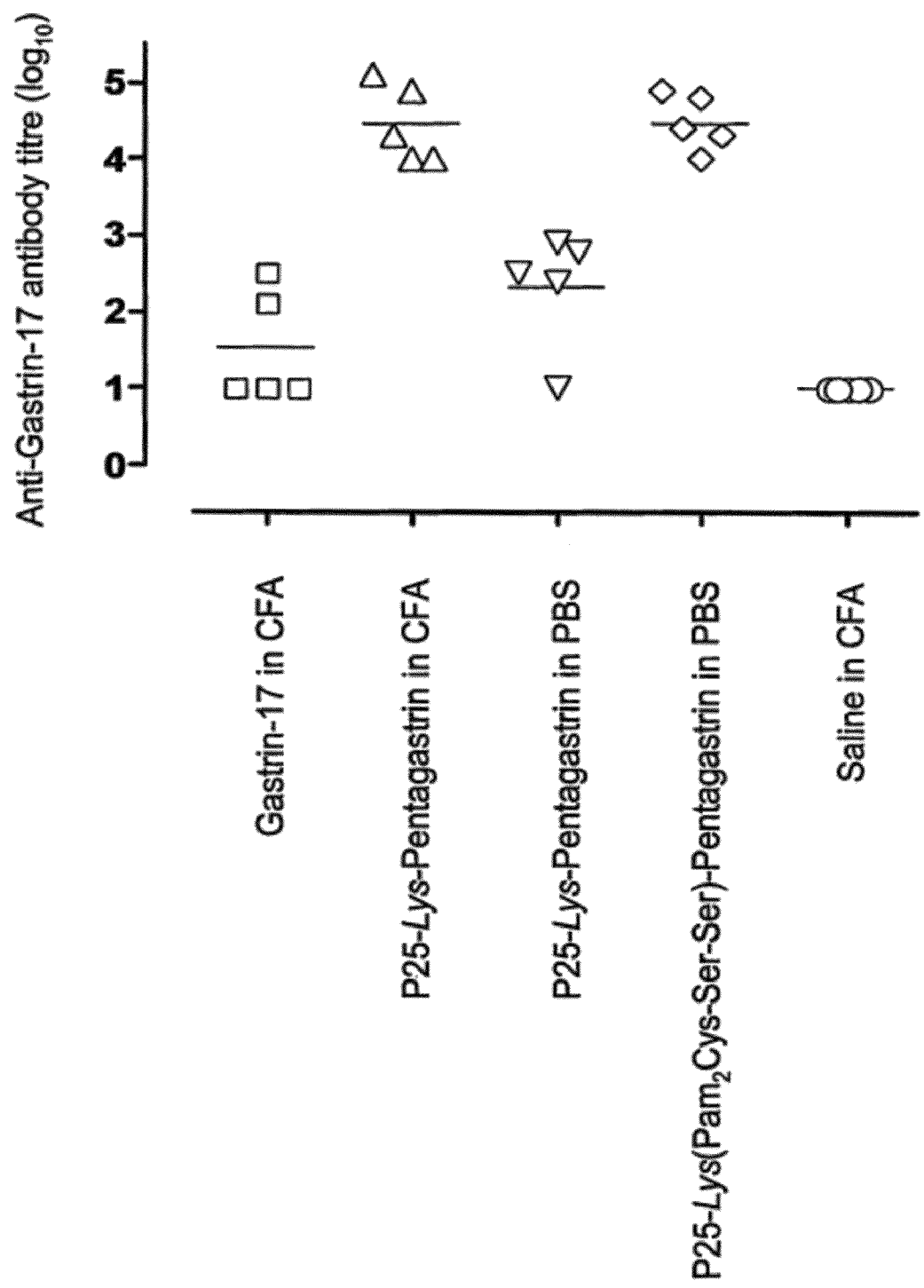

FIG. 17 is a graphical representation showing the immunogenicity of lipopeptide immunogens based on gastrin. Groups (5 animals/group) of BALB/c mice (6-8 weeks of age) were inoculated subcutaneously in the base of tail with 20 nmoles of peptide immunogens. The peptides used were Gastrin-17 (SEQ ID NO: 113); [P25]-Lys-[PentaGastrin] (SEQ ID NO: 110) in which PentaGastrin is the C-terminal sequence GWMDF of gastrin as set forth in (SEQ ID NO: 102); and [P25]-Lys($Pam_2$Cys-Ser-Ser)-[PentaGastrin] (SEQ ID NO: 110 with lipid added to an internal lysine residue). All lipopeptides were administered in PBS and the non-lipidated peptides were administered in CFA. The negative control was saline emulsified with CFA. Sera were obtained from animals 4 weeks after immunisation and at the same time the animals received a second similar dose of antigen. Mice were bled a second time 2 weeks after receiving the second dose of antigen and antibodies capable of reacting with the peptide gastrin-17 sequence detected by ELISA. The results are expressed as the titre of anti-gastrin-17 antibodies.

DETAILED DESCRIPTION OF THE PREFERRED EMBODIMENTS

Lipopeptides

One aspect of the invention provides an isolated lipopeptide comprising a polypeptide conjugated to one or more lipid moieties wherein:
(i) said polypeptide comprises an amino acid sequence that comprises:
 (a) the amino acid sequence of a T helper cell (Th) epitope and the amino acid sequence of a B cell epitope, wherein said amino acid sequences are different; and
 (b) one or more internal lysine residues or internal lysine analog residues for covalent attachment of each of said lipid moieties via the epsilon-amino group or terminal side-chain group of said lysine or lysine analog; and
(ii) each of said one or more lipid moieties is covalently attached directly or indirectly to an epsilon-amino group of said one or more internal lysine residues or to a terminal side-chain group of said internal lysine analog residues.

As used herein, the term "lipopeptide" means any non-naturally occurring composition of matter comprising one or more lipid moieties and one or more amino acid sequences that are directly or indirectly conjugated, said composition of matter being substantially free of non-specific non-conjugated lipid or protein.

By "directly" means that a lipid moiety and an amino acid sequence are not separated by a spacer molecule.

By "indirectly" means that a lipid moiety and an amino acid sequence are separated by a spacer comprising one or more carbon-containing molecules, such as, for example, one or more amino acid residues.

The amino acid sequence may be of any length, constrained by the requirement for functionality of both the T-helper epitope and the B cell epitope.

As used herein, the term "internal lysine residue" means a lysine residue in the polypeptide comprising both the T-helper epitope and the B-cell epitope, wherein said lysine is not the N-terminal amino acid residue or the C-terminal residue of said polypeptide. This means that the internal lysine residue to which the lipid moiety is attached is a residue that is present in the amino acid sequence of the T helper cell epitope or the amino acid sequence of the antigen. The internal lysine residue may also be distinct from the T-helper epitope or the B-cell epitope, in which case it must link these two epitopes of the polypeptide.

Similarly, the term "internal lysine analog residue" means a lysine analog residue in the polypeptide comprising both the T-helper epitope and the B-cell epitope, wherein said lysine analog is not the N-terminal amino acid residue or the C-terminal residue of said polypeptide. The criteria for establishing whether or not a lysine residue is "internal" shall apply mutatis mutandis to determining whether or not a lysine analog is internal.

By "lysine analog" is meant a synthetic compound capable of being incorporated into the internal part of a peptide that has a suitable side-group to which the lipid moiety can be coupled, including an amino acid analog or non-naturally occurring amino acid having such an amino side group. Preferred lysine analogs include compounds of the following general Formula (V):

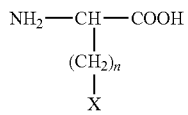

wherein n is an integer from 0 to 3 and wherein X is a terminal side-chain group of said internal lysine analog residue selected from the group consisting of NH, O and S. More preferably, n is an integer having a value from 1 to 3. More preferably, X is an amino group and the lysine analog is a diamino compound. In a particularly preferred embodiment, the lysine analog is selected from the group consisting of 2,3 diaminopropionic acid (Dpr), 2,4-diaminobutyric acid (Dab) and 2,5-diaminovaleric acid [i.e. ornithine (Orn)].

Those skilled in the art will know the meaning of the term "epsilon-amino group".

The term "terminal side-chain group" means a substituent on the side chain of a lysine analog the is distal to the alpha-carbon of said analog, such as, for example, a beta-amino of Dpr, gamma-amino of Dab, or delta-amino of Orn.

The inventors have found that the most effective lipopeptides are highly soluble. The relative ability of the lipopeptides of the invention to induce an antibody response in the absence of external adjuvant was reflected by their ability to upregulate the surface expression of MHC class II molecules on immature dendritic cells (DC), particularly D1 cells as described by Winzler et al *J Exp Med* 185, 317, 1997).

As will be known to those skilled in the art, the epsilon amino group of lysine is the terminal amino group of the side chain of this amino acid. Use of the epsilon amino group of lysine or the terminal side-chain group of a lysine analog for cross-linkage to the lipid moiety facilitates the synthesis of the polypeptide moiety as a co-linear amino acid sequence incorporating both the T-helper epitope and the B cell epitope. There is a clear structural distinction between a lipopeptide wherein lipid is attached via the epsilon amino group of a lysine residue or the terminal side-chain group of a lysine analog and a lipopeptide having the lipid attached via an alpha amino group of lysine, since the latter-mentioned lipopeptides can only have the lipid moiety conjugated to an N-terminal residue.

Accordingly, it is particularly preferred for at least one internal lysine residue or internal lysine analog to which the lipid moiety is attached to be positioned within the polypeptide moiety so as to separate the immunologically-functional epitopes. For example, the internal lysine residue or internal lysine analog residue may act as a spacer and/or linking residue between the epitopes. Naturally, wherein the internal lysine or internal lysine analog is positioned between the T-helper epitope and the B cell epitope, the lipid moiety will be attached at a position that is also between these epitopes, albeit forming a branch from the amino acid sequence of the polypeptide. Preferably, a single internal lysine residue or internal lysine analog is used to separate B cell and T-helper epitopes (e.g., any one of SEQ ID NOs: 7, 9, 13, 106, 108, 110, or 112), in which case the lipid moiety is attached via the epsilon amino group of a lysine residue or the terminal side-chain group of a lysine analog positioned between the amino acid sequences of the T helper epitope and theg antigenic B cell epitope.

The epsilon amino group of the internal lysine or the terminal side-chain group of a lysine analog can be protected by chemical groups which are orthogonal to those used to protect the alpha-amino and side-chain functional groups of other amino acids. In this way, the epsilon amino group of lysine or the terminal side-chain group of a lysine analog can be selectively exposed to allow attachment of chemical groups, such as lipid-containing moieties, specifically to the epsilon amino group or the terminal side-chain group as appropriate.

For peptide syntheses using Fmoc chemistry, a suitable orthogonally protected epsilon group of lysine is provided by the modified amino acid residue Fmoc-Lys(Mtt)-OH(NI-Fmoc-NM-4-methyltrityl-L-lysine). Similar suitable orthogonally-protected side-chain groups are available for various lysine analogs contemplated herein, e.g. Fmoc-Orn(Mtt)-OH (Nα-Fmoc-Nδ-4-methyltrityl-L-Ornithine), Fmoc-Dab(Mtt)-OH (Nα-Fmoc-Nγ-4-methyltrityl-L-diaminobutyric acid) and Fmoc-Dpr(Mtt)-OH (Nα-Fmoc-Nβ-4-methyltrityl-L-diaminopropionic acid). The side-chain protecting group Mtt is stable to conditions under which the Fmoc group present on the alpha amino group of lysine or a lysine analog is removed but can be selectively removed with 1% trifluoroacetic acid in dichloromethane. Fmoc-Lys(Dde)-OH(NI-Fmoc-NM-1-(4,4-dimethyl-2,6-dioxocyclohex-1-ylidene)ethyl-L-lysine) or Fmoc-Lys(ivDde)-OH (NI-Fmoc-NM-1-(4,4-dimethyl-2,6-dioxocyclohex-1-ylidene)-3-methylbutyl-L-lysine) can also be used in this context, wherein the Dde side-chain protecting groups is selectively removed during peptide synthesis by treatment with hydrazine.

For peptide syntheses using Boc chemistry, Boc-Lys(Fmoc)-OH can be used. The side-chain protecting group Fmoc can be selectively removed by treatment with piperidine or DBU (1,8-Diazabicyclo[5.4.0]undec-7-ene) but remains in place when the Boc group is removed from the alpha terminus using trifluoroacetic acid.

The optimum distance between the T-helper epitope and the B cell epitope, and consequently, the precise positioning and number of internal lysine or lysine analog residues in the lipopeptide of the invention, is readily determined empirically, for each combination of T helper epitopes, B cell epitopes, and lipids. In the case of synthetic peptides and polypeptides, the limitations of the synthesis methodology used to prepare the polypeptides may, in part, determine the separation between the T-helper epitope and the B cell epitope that is achievable, and the number and positioning of internal lysine or lysine analog residue(s).

Preferably, the T helper epitope and B cell epitope are separated by at least one or two or three or four or five amino acid residues including a single internal lysine residue or lysine analog residue.

The present invention clearly contemplates the addition of multiple lipid moieties to the polypeptide moiety. To achieve this, the polypeptide may include multiple internal lysine residues or multiple internal lysine analog residues or a combination thereof. Steric hindrance may occur in the addition of lipid if multiple internal lysine or lysine analog residues are positioned more closely together, thereby producing a mixture of end-products, or a reduced yield.

Relevant to this consideration is the fact that it is not necessary for the entire amino acid sequence comprising the T-helper epitope or the entire amino acid sequence comprising the B cell epitope to have an immune function. Accordingly, the said amino acid sequences, whilst comprising said epitopes may have additional sequence not possessing T-helper cell activity or a B cell epitope. Where such additional sequences include one or more internal lysine or lysine analog residues, the terminal side-chain groups of such residues may serve as attachment sites for the lipid moiety. Naturally, it is essential to retain T-helper function and B cell epitope function.

The positioning of the internal lysine residue or internal lysine analog for attachment of the lipid moiety should also be selected such that attachment of the lipid moiety does not interfere with the immune function of the T-helper epitope or the B cell epitope in a subject to whom the lipopeptide is administered. For example, depending upon the selection of lipid moiety, the attachment of said lipid within the B cell epitope may sterically hinder antigen presentation.

A generalized preferred form of the lipopeptide of the invention, wherein the internal lysine or internal lysine analog is positioned between the T-helper and B-cell epitopes is provided by the general Formula (VI).

Formula (VI):

$$\boxed{\text{epitope}} - A - NH - \underset{\underset{\underset{\underset{Z}{|}}{Y}}{\underset{X}{|}}}{\overset{}{CH}} - CO-A - \boxed{\text{epitope}}$$
$$(CH_2)_n$$

wherein:
epitope is a T-helper epitope or B-cell epitope;
A is either present or absent and consists of an amino acid spacer of about 1 to about 6 amino acids in length;
n is an integer having a value of 1, 2, 3, or 4;
X is a terminal side-chain group selected from the group consisting of NH, O and S and preferably consisting of NH;
Y is either present of absent and consists of a spacer of about 1 to about 6 amino acids in length, wherein it is preferred for said spacer to comprise arginine, serine or 6-aminohexanoic acid; and
Z is a lipid moiety, preferably a lipoamino acid moiety selected from the group consisting of $Pam_2Cys$, $Pam_3Cys$, $Ste_2Cys$, $Lau_2Cys$, and $Oct_2Cys$.

Those skilled in the art will be aware that $Ste_2Cys$ is also known as S-[2,3-bis(stearoyloxy)propyl]cysteine or distearoyl-S-glyceryl-cysteine; that $Lau_2Cys$ is also known as S-[2,3-bis(lauroyloxy)propyl]cysteine or dilauroyl-S-glyceryl-cysteine); and that $Oct_2Cys$ is also known as S-[2,3-bis(octanoyloxy)propyl]cysteine or dioctanoyl-S-glyceryl-cysteine).

The T-helper epitope is any T-helper epitope known to the skilled artisan for enhancing an immune response in a particular target subject (i.e. a human subject, or a specific non-human animal subject such as, for example, a rat, mouse, guinea pig, dog, horse, pig, or goat). Preferred T-helper epitopes comprise at least about 10-24 amino acids in length, more generally about 15 to about 20 amino acids in length.

Promiscuous or permissive T-helper epitopes are particularly preferred as these are readily synthesized chemically and obviate the need to use longer polypeptides comprising multiple T-helper epitopes.

Examples of promiscuous or permissive T-helper epitopes suitable for use in the lipopeptides of the present invention are selected from the group consisting of:
(i) a rodent or human T-helper epitope of tetanus toxoid peptide (TTP), such as, for example amino acids 830-843 of TTP (Panina-Bordignon et al., *Eur. J. Immun.* 19, 2237-2242, 1989);
(ii) a rodent or human T-helper epitope of *Plasmodium falciparum* pfg27;
(iii) a rodent or human T-helper epitope of lactate dehydrogenase;
(iv) a rodent or human T-helper epitope of the envelope protein of HIV or HIVgp120 (Berzofsky et al., *J. Clin. Invest.* 88, 876-884, 1991);
(v) a synthetic human T-helper epitope (PADRE) predicted from the amino acid sequence of known anchor proteins (Alexander et al., *Immunity* 1, 751-761, 1994);
(vi) a rodent or human T-helper epitope of measles virus fusion protein (MV-F; Muller et al., *Mol. Immunol.* 32, 37-47, 1995; Partidos et al., *J. Gen. Virol.*, 71, 2099-2105, 1990);
(vii) a T-helper epitope comprising at least about 10 amino acid residues of canine distemper virus fusion protein (CDV-F) such as, for example, from amino acid positions 148-283 of CDV-F (Ghosh et al., *Immunol.* 104, 58-66, 2001; International Patent Publication No. WO 00/46390);
(viii) a human T-helper epitope derived from the peptide sequence of extracellular tandem repeat domain of MUC1 mucin (US Patent Application No. 0020018806);
(ix) a rodent or human T-helper epitope of influenza virus hemagglutinin (IV-H) (Jackson et al. *Virol.* 198, 613-623, 1994; and
(x) a bovine or camel T-helper epitope of the VP3 protein of foot and mouth disease virus (FMDV-$0_1$ Kaufbeuren strain), comprising residues 173 to 176 of VP3 or the corresponding amino acids of another strain of FMDV.

As will be known to those skilled in the art, a T-helper epitope may be recognised by one or more mammals of different species. Accordingly, the designation of any T-helper epitope herein is not to be considered restrictive with respect to the immune system of the species in which the epitope is recognised. For example, a rodent T-helper epitope can be recognised by the immune system of a mouse, rat, rabbit, guinea pig, or other rodent, or a human or dog.

More preferably, the T-helper epitope will comprise an amino acid sequence selected from the group consisting of:

(i)      GALNNRFQIKGVELKS from IV-H;    (SEQ ID NO: 1)

(ii)     ALNNRFQIKGVELKS from IV-H;    (SEQ ID NO: 18)

(iii)    LSEIKGVIVHRLEGV from MV-F;    (SEQ ID NO: 19)

(iv)     TAAQITAGIALHQSNLN from CDV-F;    (SEQ ID NO: 20)

(v)      IGTDNVHYKIMTRPSHQ from CDV-F;    (SEQ ID NO: 21)

(vi)     YKIMTRPSHQYLVIKLI from CDV-F;    (SEQ ID NO: 22)

|  |  | (SEQ ID NO: 23) |
|---|---|---|
| (vii) | SHQYLVIKLIPNASLIE from CDV-F; | |

|  |  | (SEQ ID NO: 24) |
|---|---|---|
| (viii) | KLIPNASLIENCTKAEL from CDV-F; | |

|  |  | (SEQ ID NO: 25) |
|---|---|---|
| (ix) | LIENCTKAELGEYEKLL from CDV-F; | |

|  |  | (SEQ ID NO: 26) |
|---|---|---|
| (x) | AELGEYEKLLNSVLEPI from CDV-F; | |

|  |  | (SEQ ID NO: 27) |
|---|---|---|
| (xi) | KLLNSVLEPINQALTLM from CDV-F; | |

|  |  | (SEQ ID NO: 28) |
|---|---|---|
| (xii) | EPINQALTLMTKNVKPL from CDV-F; | |

|  |  | (SEQ ID NO: 29) |
|---|---|---|
| (xiii) | TLMTKNVKPLQSLGSGR from CDV-F; | |

|  |  | (SEQ ID NO: 30) |
|---|---|---|
| (xiv) | KPLQSLGSGRRQRRFAG from CDV-F; | |

|  |  | (SEQ ID NO: 31) |
|---|---|---|
| (xv) | SGRRQRRFAGVVLAGVA from CDV-F; | |

|  |  | (SEQ ID NO: 32) |
|---|---|---|
| (xvi) | FAGVVLAGVALGVATAA from CDV-F; | |

|  |  | (SEQ ID NO: 33) |
|---|---|---|
| (xvii) | GVALGVATAAQITAGIA from CDV-F; | |

|  |  | (SEQ ID NO: 34) |
|---|---|---|
| (xviii) | GIALHQSNLNAQAIQSL from CDV-F; | |

|  |  | (SEQ ID NO: 35) |
|---|---|---|
| (xix) | NLNAQAIQSLRTSLEQS from CDV-F; | |

|  |  | (SEQ ID NO: 36) |
|---|---|---|
| (xx) | (QSLRTSLEQSNKAIEEI from CDV-F; | |

|  |  | (SEQ ID NO: 37) |
|---|---|---|
| (xxi) | EQSNKAIEEIREATQET from CDV-F; | |

|  |  | (SEQ ID NO: 38) |
|---|---|---|
| (xxii) | SSKTQTHTQQDRPPQPS from CDV-F; | |

|  |  | (SEQ ID NO: 39) |
|---|---|---|
| (xxiii) | QPSTELEETRTSRARHS from CDV-F; | |

|  |  | (SEQ ID NO: 40) |
|---|---|---|
| (xxiv) | RHSTTSAQRSTHYDPRT from CDV-F; | |

|  |  | (SEQ ID NO: 41) |
|---|---|---|
| (xxv) | PRTSDRPVSYTMNRTRS from CDV-F; | |

|  |  | (SEQ ID NO: 42) |
|---|---|---|
| (xxvi) | TRSRKQTSHRLKNIPVH from CDV-F; | |

|  |  | (SEQ ID NO: 43) |
|---|---|---|
| (xxvii) | TELLSIFGPSLRDPISA from CDV-F; | |

|  |  | (SEQ ID NO: 44) |
|---|---|---|
| (xxviii) | PRYIATNGYLISNFDES from CDV-F; | |

|  |  | (SEQ ID NO: 45) |
|---|---|---|
| (xxix) | CIRGDTSSCARTLVSGT from CDV-F; | |

|  |  | (SEQ ID NO: 46) |
|---|---|---|
| (xxx) | DESSCVFVSESAICSQN from CDV-F; | |

|  |  | (SEQ ID NO: 47) |
|---|---|---|
| (xxxi) | TSTIINQSPDKLLTFIA from CDV-F; | |

|  |  | (SEQ ID NO: 48) |
|---|---|---|
| (xxxii) | SPDKLLTFIASDTCPLV from CDV-F; | |

|  |  | (SEQ ID NO: 49) |
|---|---|---|
| (xxxiii) | STAPPAHGVTSAPDTRAPGSTAPP from MUC-1; | |

|  |  | (SEQ ID NO: 50) |
|---|---|---|
| (xxxiv) | GVTSAPDTRPAPGSTASSL from MUC-1; | |

|  |  | (SEQ ID NO: 51) |
|---|---|---|
| (xxxv) | GVTSAPDTRPAPGSTASL from MUC-1; | |

|  |  | (SEQ ID NO: 52) |
|---|---|---|
| (xxxvi) | TAPPAHGVTSAPDTRPAPGSTAPPKKG from MUC-1; | |

|  |  | (SEQ ID NO: 53) |
|---|---|---|
| (xxxvii) | STAPPAHGVTSAPDTRPAPGSTAPPK from MUC-1; | |

|  |  | (SEQ ID NO: 54) |
|---|---|---|
| (xxxviii) | GVAE from FMDV-VP3 protein; | |

|  |  | (SEQ ID NO: 55) |
|---|---|---|
| (xxxix) | TASGVAETTN from FMDV-VP3 protein (residues 170 to 179); | | and

|  |  | (SEQ ID NO: 56) |
|---|---|---|
| (xl) | TAKSKKFPSYTATYQF from FMDV. | |

The T-helper epitopes disclosed herein are included for the purposes of exemplification only. Using standard peptide synthesis techniques known to the skilled artisan, the T-helper epitopes referred to herein are readily substituted for a different T-helper epitope to adapt the lipopeptide of the invention for use in a different species. Accordingly, additional T-helper epitopes known to the skilled person to be useful in eliciting or enhancing an immune response in a target species are not to be excluded.

Additional T-helper epitopes may be identified by a detailed analysis, using in vitro T-cell stimulation techniques of component proteins, protein fragments and peptides to identify appropriate sequences (Goodman and Sercarz, *Ann. Rev. Immunol.*, 1, 465, (1983); Berzofsky, In: "The Year in Immunology, Vol. 2" page 151, Karger, Basel, 1986; and Livingstone and Fathman, *Ann. Rev. Immunol.*, 5, 477, 1987).

The B cell epitope is conveniently derived from the amino acid sequence of an immunogenic protein, lipoprotein, or glycoprotein of a virus, prokaryotic or eukaryotic organism, including but not limited to an antigen derived from a mammalian subject or a bacterium, fungus, protozoan, or parasite that infects said subject. Idiotypic and anti-idiotypic B cell epitopes against which an immune response is desired are specifically included, as are lipid-modified B cell epitopes. Alternatively, the B cell epitope may be a carbohydrate antigen, such as, for example, an ABH blood group antigen, transplantation antigen (e.g. Gal alpha1-3Gal beta1-4GlcNAc; Sandrin et al., *Proc. Natl. Acad. Sci. USA* 90, 11391-11395, 1993; Galili et al., *Proc. Natl. Acad. Sci. USA* 84, 1369-1373, 1987; Schofield et al., *Nature* 418: 785-789, 2002) or a conjugate thereof.

The B-cell epitope will be capable of eliciting the production of antibodies when administered to a mammal, preferably neutralizing antibody, and more preferably, a high titer neutralizing antibody.

Shorter B cell epitopes are preferred, to facilitate peptide synthesis.

Preferably, the length of the B cell epitope will not exceed about 30 amino acids in length. More preferably, the B cell epitope sequence consists of about 25 amino acid residues or less, and more preferably less than 20 amino acid residues, and even more preferably about 5-20 amino acid residues in length.

Preferably, peptides will assume a conformation that mimics the conformation of the native polypeptide from which the B cell epitope is derived.

Preferred B cell epitopes from parasites are those associated with *leishmania*, malaria, trypanosomiasis, babesiosis, or schistosomiasis, such as, for example a B cell epitope selected from the group consisting of:

(i) a B cell epitope of *Plasmodium falciparum* (NANP) 3 (Good et al., *J. Exp. Med.* 164, 655 1986);
(ii) a B cell epitope of *Circumsporozoa* (Good et al., *Protein Sci.*, 235, 1059, 1987);
(iii) a B cell epitope comprising amino acid residues 326-343 of *Leishmania donovani* Repetitive Peptide (Liew et al., *J. Exp. Med.* 172, 1359 (1990));
(iv) a B cell epitope of *Toxoplasma gondii* P30 surface protein (Darcy et al., *J. Immunol.* 149, 3636 (1992)); and
(v) a B cell epitope of *Schistosoma mansoni* Sm-28GST antigen (Wolowxzuk et al., *J. Immunol.* 146:1987 (1991)).

Preferred virus-specific B cell epitopes are derived from and/or capable of generating antibodies against Rotaviruses, Herpes viruses, Corona viruses, Picornaviruses (e.g. Apthovirus), Respiratory Synctial virus, Influenza Virus, Parainfluenza virus, Adenovirus, Pox viruses, Bovine herpes virus Type I, Bovine viral diarrhea virus, Bovine rotaviruses, Canine Distemper Virus (CDV), Equine Rhinitis A Virus (ERAV); Equine Rhinitis B Virus (ERBV); Foot and Mouth Disease Virus (FMDV), Measles Virus (MV), Human Immunodeficiency Viruses (HIV), Feline Immunodeficiency Viruses (FIV), Epstein-Barr virus (EBV), or hepatitis virus, and the like. Suitable viral B cell epitopes include, but are not limited to epitopes selected from the group consisting of:

(i) HIV gp120 V3 loop, amino acid residues 308-331 (Jatsushita et al., *J. Virol.* 62, 2107 (1988));
(ii) HIV gp120 amino acid residues 428-443 (Ratner et al., *Nature* 313:277 (1985));
(iii) HIV gp120 amino acid residues 112-124 (Berzofsky et al., *Nature* 334, 706 (1988));
(iv) a B cell epitope of HIV Reverse transcriptase (Hosmalin et al. *Proc. Natl. Acad. Sci.* (USA) 87, 2344 (1990));
(v) Influenza virus nucleoprotein amino acid residues 335-349 (Townsend et al. *Cell* 44, 959 (1986));
(vi) Influenza virus nucleoprotein amino acid residues 366-379 (Townsend et al. *Cell* 44, 959 (1986));
(vii) Influenza virus hemagglutinin amino acid residues 48-66 (Mills et al., *J. Exp. Med.* 163, 1477 (1986));
(viii) Influenza virus hemagglutinin amino acid residues 111-120 (Hackett et al., *J. Exp. Med.* 158, 294 (1983));
(ix) Influenza virus hemagglutinin amino acids 114-131 (Lamb and Green, *Immunology* 50, 659 (1983));
(x) Epstein-Barr LMP amino acid residues 43-53 (Thorley-Lawson et al., *Proc. Natl. Acad. Sci.* (USA) 84, 5384 (1987));
(xi) Hepatitis B virus surface antigen amino acid residues 95-109 (Milich et al., *J. Immunol.* 134, 4203 (1985));
(xii) Hepatitis B virus surface antigen amino acid residues 140-154;
(xiii) Hepatitis B virus Pre-S antigen amino acid residues 120-132 (Milich et al., *J. Exp. Med.* 164, 532 (1986));
(xiv) Herpes simplex virus gD protein amino acid residues 5-23 (Jayaraman et al., *J. Immunol.* 151, 5777 (1993));
(xv) Herpes simplex virus gD protein amino acid residues 241-260 (Wyckoff et al., *Immunobiol.,* 177, 134 (1988));
(xvi) Rabies glycoprotein amino acid residues 32-44 (MacFarlan et al., *J. Immunol.* 133, 2748 (1984));
(xvii) The major FMDV epitope comprising at least amino acid residues 134-168 or 137-160 or residues 142-160 or residues 137-162 or residues 145-150 of the VP1 capsid protein of FMDV serotype $O_1$ or the corresponding amino acid residues of another serotype, such as, for example, serotypes A, C, SAT1, SAT2, SAT3, or ASIA1 (U.S. Pat. Nos. 5,864,008 and 6,107,021); and
(xviii) The hypervariable region-1 (HVR1) of the E2 protein of hepatitis C virus (HCV) variant AD78 (Zibert et al., *J. Virol.* 71, 4123-4127, 1997).

Preferred bacteria-specific B cell epitopes are derived from and/or capable of generating antibodies against *Pasteurella, Actinobacillus, Haemophilus, Listeria monocytogenes, Mycobacterium, Staphylococcus, E. coli, Shigella*, and the like. Suitable bacterial B cell epitopes include, but are not limited to epitopes selected from the group consisting of:

(i) *Mycobacterium tuberculosis* 65 Kd protein amino acid residues 112-126 (Lamb et al., *EMBO J.,* 6, 1245 (1987));
(ii) *M. tuberculosis* 65 Kd protein amino acid residues 163-184 (Lamb et al., *EMBO J.,* 6, 1245 (1987));
(iii) *M. tuberculosis* 65 Kd protein amino acid residues 227-243 (Lamb et al., *EMBO J.,* 6, 1245 (1987));
(iv) *M. tuberculosis* 65 Kd protein amino acid residues 242-266 (Lamb et al., *EMBO J.,* 6, 1245 (1987));
(v) *M. tuberculosis* 65 Kd protein amino acid residues 437-459 (Lamb et al., *EMBO J.,* 6, 1245 (1987));
(vi) *M. tuberculosis* ESAT-6 protein residues 3-15 (Morten et al., *Infect. Immun.* 66, 717-723, 1998);
(vii) *M. tuberculosis* ESAT-6 protein residues 40-62 (Morten et al., *Infect. Immun.* 66, 717-723, 1998);
(viii) *Mycobacterium scrofulaceum* alpha-antigen residues 279-290 (Mikiko et al., *Microb. Path.* 23, 95-100, 1997);
(ix) *Staphylococcus aureus* nuclease protein amino acid residues 61-80 (Finnegan et al., *J. Exp. Med.* 164, 897 (1986));
(x) a B cell epitope of *Escherichia coli* heat stable enterotoxin (Cardenas et al., *Infect. Immunity* 61, 4629 (1993));
(xi) a B cell epitope of *Escherichia coli* heat labile enterotoxin (Clements et al., *Infect. Immunity* 53, 685 (1986));
(xii) a B cell epitope of *Shigella sonnei* form I antigen (Formal et al., *Infect. Immunity* 34, 746 (1981));
(xiii) a B cell epitope from Group A *Streptococcus*, preferably derived from the M protein, more preferably from the C-terminal half of the M protein and more preferably a minimum, helical, non-host-cross-reactive peptide derived from the conserved C-terminal half of the M protein and comprising a non-M-protein peptide designed to maintain helical folding and antigenicity displayed within said minimum, helical, non-host-cross-reactive peptide. For example, the non-M-protein peptide (eg peptide J14) can be linked to one or more serotypic M protein peptides using chemistry that enables the immunogen to display all the individual peptides pendant from an alkane backbone, thereby conferring excellent immunogenicity and protection (U.S. Pat. No. 6,174,528; Brandt et al., *Nat. Med.* 6: 455-459, 2000);
(xiv) a B cell epitope of the Cholera toxin B subunit (CTB), such as, for example described by Kazemi and Finkelstein *Mol. Immunol.* 28, 865-876, 1991;
(xv) a B cell epitope of a protein of *Bacillus anthracis* (anthrax), such as, for example, a B cell epitope derived from a protein of the outer exosporium of anthrax such as the 250 kDa glycoprotein (Sylvestre et al., In: Proc. $4^{th}$ Int. Conf. Anthrax, St John's College Annapolid, Mayland, Calif. Jun. 10-13, 2001, Abstract 31B; and
(xvi) a B cell epitope from a protein of tetanus, such as, for example, the tetanus toxoid protein.

Preferred B cell epitopes from mammalian subjects are derived from and/or capable of generating antibodies against a tumor antigen. Tumor antigens are usually native or foreign antigens, the expression of which is correlated with the development, growth, presence or recurrence of a tumor. In as much as tumor antigens are useful in differentiating abnormal from normal tissue, they are useful as a target for therapeutic intervention. Tumor antigens are well known in the art. Indeed, several examples are well-characterized and are currently the focus of great interest in the generation of tumor-specific therapies. Non-limiting examples of tumor antigens are carcinoembryonic antigen (CEA), prostate specific antigen (PSA), melanoma antigens (MAGE, BAGE, GAGE), and mucins, such as MUC-1.

Alternatively, a preferred B cell epitope from a mammalian subject is derived from zona pellucida protein such as ZP3 (Chamberlin and Dean *Proc. Natl. Acad. Sci.* (USA) 87, 6014-6018, 1990) or ZP3a (Yurewicz et al., *Biochim. Biophys. Acta* 1174, 211-214, 1993)] of humans or other mammals such as pigs. Particularly preferred B cell epitopes within this category include amino acid residues 323-341 of human ZP3 (Chamberlin and Dean *Proc. Natl. Acad. Sci.* (USA) 87, 6014-6018, 1990); amino acid residues 8-18 or residues 272-283 or residues 319-330 of porcine ZP3a (Yurewicz et al., *Biochim. Biophys. Acta* 1174, 211-214, 1993).

Further preferred B cell epitopes from a mammalian subject are derived from and/or capable of generating antibodies against a peptide hormone, such as, for example, a satiety hormone (e.g. leptin), a digestive hormone (e.g. gastrin), or a reproductive peptide hormone [e.g. luteinising hormone-releasing hormone (LHRH), follicle stimulating hormone (FSH), luteinising hormone (LH), human chorionic gonadotropin (hCG; Carlsen et al., *J. Biol. Chem.* 248, 6810-6827, 1973), or alternatively, a hormone receptor such as, for example, the FSH receptor (Kraaij et al., *J. Endocrinol.* 158, 127-136, 1998). Particularly preferred B cell epitopes within this category include the C-terminal portion (CTP) of b-hCG that is antigenically non cross-reactive with LH (Carlsen et al., *J. Biol. Chem.* 248, 6810-6827, 1973).

In a particularly preferred embodiment, a peptide comprising a B-cell epitope will comprise an amino acid sequence selected from the group consisting of:

(i) EHWSYGLRPG derived from LHRH (herein referred to as "LHRH 1-10"; SEQ ID NO: 2);

(ii) HWSYGLRPG derived from LHRH (herein referred to as "LHRH 2-10"; SEQ ID NO: 3);

(iii) GLRPG derived from LHRH ((herein referred to as "LHRH 6-10"; SEQ ID NO: 4);

(iv) EAEEAARLQA from Leishmani major (SEQ ID NO: 57);

(v) a sequence from a non-structural protein 3A, 3B, or 3C of FMDV (U.S. Pat. No. 6,048,538) selected from the group consisting of: FRERTLTGQRACNDVNSE (SEQ ID NO: 58), NPLETSGASTVGFRERTL (SEQ ID NO: 59), IRETRKRQKMVDDAVNEY (SEQ ID NO: 60), AKAPVVKEGPYEGPVKKPV (SEQ ID NO: 61), AGPLERQKPLKVKAKAPVV (SEQ ID NO: 62), KVRAKLPQQEGPYAGPLER (SEQ ID NO: 63), GPYTGPLERQRPLKVRAKL (SEQ ID NO: 64), VGRLIFSGEALTYKDIVV (SEQ ID NO: 65), TKHFRDTARMKKGTPVVGV (SEQ ID NO: 66), and SGAPPTDLQKMVMGNTKPV (SEQ ID NO: 67);

(vi) NKYSASGSGVRGDFGSLAPRVARQLPASFNYGAIK from the FMDV VP1 major epitope (U.S. Pat. No. 6,107,021; SEQ ID NO: 68);

(vii) a sequence from prostate specific antigen (U.S. Pat. No. 6,326,471) selected from the group consisting of: LYTKVVHYRKWIKDTIVANP (SEQ ID NO: 69), AVKVMDLPQEPALGTTCYA (SEQ ID NO: 70), IVGGWECEKHSQPWQVLVAS (SEQ ID NO: 71), CAQVHPQKVTKFML (SEQ ID NO: 72), YLMLLRLSEPAELTDDAVKVM (SEQ ID NO: 73), LLKNRFL-RPGDDSSHDLMLLY (SEQ ID NO: 74), and ILLGRHSLFHPEDTGQVFQVY (SEQ ID NO: 75);

(viii) TCDDPRFQDSSSSKAPPPSLPSPSRLPGPSDTPILPQ from b-hCG (SEQ ID NO: 76);

(ix) CQDSKVTEIPTLPRNAI from the FSH receptor (SEQ ID NO: 77);

(x) NKGDCGTPSHSRRQPHVMS from human ZP3 protein (SEQ ID NO: 78);

(xi) a sequence from porcine ZP3a protein selected from the group consisting of: WLCFPLCLALP (SEQ ID NO: 79) LGGLYCGPSSF (SEQ ID NO: 80), GSITRDSIFRLR (SEQ ID NO: 81), SALPVNIQVFTL (SEQ ID NO: 82), ELQIAKDERYGS (SEQ ID NO: 83), and VKLLREPIYVEV (SEQ ID NO: 84);

(xii) PPAQYSWLIDGN from carcinoembryonic antigen (CEA; SEQ ID NO: 85);

(xiii) a sequence from Staphylococcal nuclease (Cone et al., *J. Biol. Chem.* 246, 3103-3110. 1971) selected from the group consisting of: ANASQTDNGVNRSGSEDPTV (SEQ ID NO: 86) and PETKHPKKGVEKYGPEASAF (SEQ ID NO: 87);

(xiv) a sequence of Hepatitis B virus Surface antigen (Kobayashi and Koike, *Gene* 30, 227-232, 1984) selected from the group consisting of: LVLLDYQGMLPVCPL (SEQ ID NO: 88) and TKPSDGNCTCIPIPS (SEQ ID NO: 89);

(xv) MQWNSTTFHQALL from Hepatitis B virus precursor Surface antigen (SEQ ID NO: 90);

(xvi) a sequence from Influenza virus nucleoprotein (Gregory et al., *J. Gen. Virol.* 82, 1397-1406, 2001) selected from the group consisting of: AAFEDLRVSSFIRGT (SEQ ID NO: 91) and SNENMETMDSSTLE (SEQ ID NO: 92);

(xvii) a sequence from Influenza virus hemagglutinin selected from the group consisting of: HPLILDTCTIEGLIYGNPS (SEQ ID NO: 93), YQRIQIFPDT (SEQ ID NO: 94), and IQIFPDTIWNVSYSGTSK (SEQ ID NO: 95);

(xviii) CKYSASGSGVRGDFGSLAPRVARCLPASFNTGAIKNKY from the FMDV envelope glycoprotein VP1 (SEQ ID NO: 96);

(xix) a sequence from the *M. tuberculosis* ESAT-6 protein selected from the group consisting of: EQQWNFAGIEAAA (SEQ ID NO: 97) and AAAWGGSGSEAYQGVQQKWDATA (SEQ ID NO: 98).

(xx) GGPTRTIGGSQAQTASGLVSMFSVGPSQK (SEQ ID NO: 99) from HCV;

(xxi) KFQDAYNAAGGH (SEQ ID NO: 100) from *M. scrofulaceum* alpha antigen;

(xxii) KQAEDKVKASREAKKQVEKALEQLEDKVK (SEQ ID NO: 101) from the M protein of group A *Streptococcus* (i.e., peptide designated herein as "J14"); and (xxiii) GWMDF (SEQ ID NO: 102) from gastrin (i.e., pentagastrin consisting of the C-terminal five amino acid residues of gastrin).

(xxiv) It will be apparent from the preceding description that the polypeptide moiety of the subject lipopeptide is synthesized conveniently as a single amino acid chain, thereby requiring no post-synthesis modification to incorporate both epitopes.

A polypeptide moiety which comprises a highly immunogenic B cell epitope of LHRH (e.g. SEQ ID NO: 2 or 3 or 4) linked either to a T-helper epitope of influenza virus hemagglutinin (e.g. SEQ ID NO: 1) or a T-helper epitope of CDV-F (e.g. SEQ ID NO: 20, 24, 26, or 44) is particularly preferred, such as, for example, a polypeptide comprising an amino acid sequence selected from the group consisting of:

```
(i)
GALNNRFQIKGVELKSEHWSYGLRPG;            (SEQ ID NO: 5)

(ii)
EHWSYGLRPGGALNNRFQIKGVELKS;            (SEQ ID NO: 6)

(iii)
GALNNRFQIKGVELKSKEHWSYGLRPG;           (SEQ ID NO: 7)

(iv)
EHWSYGLRPGKGALNNRFQIKGVELKS;           (SEQ ID NO: 8)

(v)
KLIPNASLIENCTKAELKHWSYGLRPG;           (SEQ ID NO: 9)

(vi)
AELGEYEKLLNSVLEPIKEHWSYGLRPG;          (SEQ ID NO: 10)

(vii)
TAAQITAGIALHQSNLNKEHWSYGLRPG;          (SEQ ID NO: 11)

(viii)
PRYIATNGYLISNFDESKEHWSYGLRPG;          (SEQ ID NO: 12)

(ix)
KLIPNASLIENCTKAELKGLRPG;               (SEQ ID NO: 13)

(x)
AELGEYEKLLNSVLEPIKGLRPG;               (SEQ ID NO: 14)

(xi)
TAAQITAGIALHQSNLNKGLRPG;               (SEQ ID NO: 15)

(xii)
PRYIATNGYLISNFDESKGLRPG;               (SEQ ID NO: 16)

(xiii)
KLIPNASLIENCTKAELHWSYGLRPG;            (SEQ ID NO: 103)
and (xiv)
KLIPNASLIENCTKAELGLRPG.                (SEQ ID NO: 104)
```

In a particularly preferred embodiment, the LHRH epitope (i.e. LHRH1-10 as set forth in SEQ ID NO: 2; LHRH 2-10 as set forth in SEQ ID NO: 3; or LHRH 6-10 as set forth in SEQ ID NO: 4) is positioned such that the C-terminal glycine residue is exposed or not internal. Accordingly, the configuration set forth in any one of SEQ ID Nos: 5, 7, or 9-16 is particularly preferred.

In one exemplified embodiment, LHRH 1-10 is conjugated to the T-helper epitope of influenza virus hemagglutinin (i.e., SEQ ID NO: 1) as described by the sequence set forth in SEQ ID NO: 5 or 7, and LHRH 2-10 or LHRH 6-10 is conjugated to a T-helper epitope of CDV-F (i.e., SEQ ID NO: 24) as described by the sequence set forth in SEQ ID NO: 9, 13, 103 or 104. Other combinations are clearly possible and encompassed by the present invention.

In an alternative embodiment, a polypeptide moiety which comprises a highly immunogenic B cell epitope of the M protein of Group A *streptococcus* (e.g. the J14 peptide set forth in SEQ ID NO: 101) linked to a T-helper epitope of CDV-F (e.g. SEQ ID NO: 24) or influenza virus hemagglutinin (e.g., SEQ ID NO: 1) is particularly preferred, such as, for example, a polypeptide comprising an amino acid sequence selected from the group consisting of:

```
(i)                                    (SEQ ID NO: 105)
KLIPNASLIENCTKAELKQAEDKVKASREAKKQVEKALEQLEDKVK;

(ii)                                   (SEQ ID NO: 106)
KLIPNASLIENCTKAELKKQAEDKVKASREAKKQVEKALEQLEDKVK;

(iii)                                  (SEQ ID NO: 107)
GALNNRFQIKGVELKSKQAEDKVKASREAKKQVEKALEQLEDKVK;
and (iv)                                   (SEQ ID NO: 108)
GALNNRFQIKGVELKSKKQAEDKVKASREAKKQVEKALEQLEDKVK.
```

In a further alternative embodiment, a polypeptide moiety which comprises a highly immunogenic B cell epitope of pentagastrin (e.g. SEQ ID NO: 102) linked to a T-helper epitope of CDV-F (e.g. SEQ ID NO: 24) or influenza virus hemagglutinin (e.g., SEQ ID NO: 1) is particularly preferred, such as, for example, a polypeptide comprising an amino acid sequence selected from the group consisting of:

```
(i)     KLIPNASLIENCTKAELGWMDF;   (SEQ ID NO: 109)

(ii)    KLIPNASLIENCTKAELKGWMDF;  (SEQ ID NO: 110)

(iii)   GALNNRFQIKGVELKSGWMDF;    (SEQ ID NO: 111)
and (iv)    GALNNRFQIKGVELKSKGWMDF.   (SEQ ID NO: 112)
```

The skilled artisan will readily be able to synthesize additional polypeptide moieties to those exemplified herein for use in the subject lipopeptides, by substituting the T-helper epitope and/or the B cell epitope of any one of SEQ ID Nos: 5-16 or any one of SEQ ID Nos: 103-112 with another T-helper epitope or B cell epitope, such as, for example a T-helper epitope set forth in any one of SEQ ID Nos: 18-56, or a B cell epitope set forth in any one of SEQ ID Nos: 57-102. Moreover, the selection of appropriate T-helper epitope and B cell combinations will be apparent to the skilled artisan from the disclosure provided herein, according to the target species and the antigen against which an immune response is sought.

The amino acid sequences of the polypeptide moities described herein, including those exemplified polypeptides set forth in SEQ ID Nos: 5-16 and SEQ ID Nos: 103-112, may be modified for particular purposes according to methods well known to those of skill in the art without adversely affecting their immune function. For example, particular peptide residues may be derivatized or chemically modified in order to enhance the immune response or to permit coupling of the peptide to other agents, particularly lipids. It also is possible to change particular amino acids within the peptides without disturbing the overall structure or antigenicity of the peptide. Such changes are therefore termed "conservative" changes and tend to rely on the hydrophilicity or polarity of the residue. The size and/or charge of the side chains also are relevant factors in determining which substitutions are conservative.

It is well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which specific amino acids may be substituted. Particular embodiments encompass variants that have one, two, three, four, five or more variations in the amino acid sequence of the peptide. Of course, a plurality of distinct proteins/peptides with different substitutions may easily be made and used in accordance with the invention.

Those skilled in the art are well aware that the following substitutions are permissible conservative substitutions (i) substitutions involving arginine, lysine and histidine; (ii) substitutions involving alanine, glycine and serine; and (iii) substitutions involving phenylalanine, tryptophan and tyrosine. Peptides incorporating such conservative substitutions are defined herein as biologically functional equivalents.

The importance of the hydropathic amino acid index in conferring interactive biological function on a protein is generally understood in the art (Kyte & Doolittle, *J. Mol. Biol.* 157, 105-132, 1982). It is known that certain amino acids may be substituted for other amino acids having a similar hydropathic index or score and still retain a similar biological activity. The hydropathic index of amino acids also may be considered in determining a conservative substitution that produces a functionally equivalent molecule. Each amino acid has been assigned a hydropathic index on the basis of their hydrophobicity and charge characteristics, as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making changes based upon the hydropathic index, the substitution of amino acids whose hydropathic indices are within .+/−0.2 is preferred. More preferably, the substitution will involve amino acids having hydropathic indices within .+/−0.1, and more preferably within about +/−0.05.

It is also understood in the art that the substitution of like amino acids is made effectively on the basis of hydrophilicity, particularly where the biological functional equivalent protein or peptide thereby created is intended for use in immunological embodiments, as in the present case (e.g. U.S. Pat. No. 4,554,101), As detailed in U.S. Pat. No. 4,554,101, the following hydrophilicity values have been assigned to amino acid residues: arginine (+3.0); lysine (+3.0); aspartate (+3.0+/−0.1); glutamate (+3.0+/−0.1); serine (+0.3); asparagine (+0.2); glutamine (+0.2); glycine (0); threonine (−0.4); proline (−0.5+/−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, it is preferred to substitute amino acids having hydrophilicity values within about +/−0.2 of each other, more preferably within about +/−0.1, and even more preferably within about +/−0.05.

Having identified peptides suitable for use as immunogens, it also is contemplated that other sterically similar compounds may be formulated to mimic the key portions of the peptide structure. Such compounds, which may be termed peptidomimetics, may be used in the same manner as the peptides of the invention and hence are also functional equivalents. The generation of a structural functional equivalent may be achieved by the techniques of modeling and chemical design known to those of skill in the art. It will be understood that all such sterically similar constructs fall within the scope of the present invention.

Another method for determining the "equivalence" of modified peptides involves a functional approach. For example, a given peptide is used to generate monoclonal or polyclonal antibodies. These antibodies can then, in turn, be used to screen libraries of degenerate peptides that include thousands or hundreds of thousands of other peptides, thereby identifying structures that are, at least to a certain extent, immunologically equivalent. Of course, these structures may bear some primary sequence homology to the peptide used to generate the antibodies, but they also may be quite different.

The polypeptide moiety is readily synthesized using standard techniques, such as the Merrifield method of synthesis (Merrifield, *J Am Chem Soc,* 85:2149-2154, 1963) and the myriad of available improvements on that technology (see e.g., Synthetic Peptides: A User's Guide, Grant, ed. (1992) W.H. Freeman & Co., New York, pp. 382; Jones (1994) The Chemical Synthesis of Peptides, Clarendon Press, Oxford, pp. 230.); Barany, G. and Merrifield, R. B. (1979) in *The Peptides* (Gross, E. and Meienhofer, J. eds.), vol. 2, pp. 1-284, Academic Press, New York; Wünsch, E., ed. (1974) *Synthese von Peptiden in Houben-Weyls Methoden der Organischen Chemie* (Müler, E., ed.), vol. 15, 4th edn., Parts 1 and 2, Thieme, Stuttgart; Bodanszky, M. (1984) *Principles of Peptide Synthesis*, Springer-Verlag, Heidelberg; Bodanszky, M. & Bodanszky, A. (1984) *The Practice of Peptide Synthesis*, Springer-Verlag, Heidelberg; Bodanszky, M. (1985) *Int. J. Peptide Protein Res.* 25, 449-474.

The lipid moiety may comprise any $C_2$ to $C_{30}$ saturated, monounsaturated, or polyunsaturated linear or branched fatty acyl group, and preferably a fatty acid group selected from the group consisting of: palmitoyl, myristoyl, stearoyl, lauroyl, octanoyl, and decanoyl.

Lipoamino acids are particularly preferred lipid moieties within the present context. As used herein, the term "lipoamino acid" refers to a molecule comprising one or two or three or more lipids covalently attached to an amino acid residue, such as, for example, cysteine or serine or lysine or an analog thereof. In a particularly preferred embodiment, the lipoamino acid comprises cysteine and optionally, one or two or more arginine or serine residues, or alternatively, 6-aminohexanoic acid.

The lipid moiety is preferably a compound having a structure of General Formula (VII):

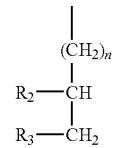

wherein:
(i) X is selected from the group consisting of sulfur, oxygen, disulfide (—S—S—), methylene (—CH$_2$—), and amino (—NH—);
(ii) m is an integer being 1 or 2;
(iii) n is an integer from 0 to 5;
(iv) R$_1$ is selected from the group consisting of hydrogen, carbonyl (—CO—), and R'—CO— wherein R' is selected from the group consisting of alkyl having 7 to 25 carbon atoms, alkenyl having 7 to 25 carbon atoms, and alkynyl having 7 to 25 carbon atoms, wherein said alkyl, alkenyl or alkynyl group is optionally substituted by a hydroxyl, amino, oxo, acyl, or cycloalkyl group;
(v) R$_2$ is selected from the group consisting of R'—CO—O—, R'—O—, R'—O—CO—, R'—NH—CO—, and R'—CO—NH—, wherein R' is selected from the group consisting of alkyl having 7 to 25 carbon atoms, alkenyl having 7 to 25 carbon atoms, and alkynyl having 7 to 25 carbon atoms, wherein said alkyl, alkenyl or alkynyl group is optionally substituted by a hydroxyl, amino, oxo, acyl, or cycloalkyl group; and
(vi) R$_3$ is selected from the group consisting of R'—CO—O—, R'—O—, R'—O—CO—, R'—NH—CO—, and R'—CO—NH—, wherein R' is selected from the group consisting of alkyl having 7 to 25 carbon atoms, alkenyl having 7 to 25 carbon atoms, and alkynyl having 7 to 25 carbon atoms, wherein said alkyl, alkenyl or alkynyl group is optionally substituted by a hydroxyl, amino, oxo, acyl, or cycloalkyl group;

and wherein each of $R_1$, $R_2$ and $R_3$ are the same or different.

Depending upon the substituent, the lipid moiety of general structure VII may be a chiral molecule, wherein the carbon atoms directly or indirectly covalently bound to integers $R_1$ and $R_2$ are asymmetric dextrorotatory or levorotatory (i.e. an R or S) configuration.

Preferably, X is sulfur; m and n are both 1; $R_1$ is selected from the group consisting of hydrogen, and R'—CO—, wherein R' is an alkyl group having 7 to 25 carbon atoms; and $R_2$ and $R_3$ are selected from the group consisting of R'—CO—O—, R'—O—, R'—O—CO—, R'—NH—CO—, and R'—CO—NH—, wherein R' is an alkyl group having 7 to 25 carbon atoms.

Preferably, R' is selected from the group consisting of: palmitoyl, myristoyl, stearoyl, lauroyl, octanoyl, and decanoyl. More preferably, R' is selected from the group consisting of: palmitoyl, stearoyl, lauroyl, and octanoyl, and decanoyl.

Each integer R' in said lipid moiety may be the same or different.

In a particularly preferred embodiment, X is sulfur; m and n are both 1; $R_1$ is hydrogen or R'—CO— wherein R' is selected from the group consisting of: palmitoyl, stearoyl, lauroyl, and octanoyl; and $R_2$ and $R_3$ are each R'—CO—O— wherein R' is selected from the group consisting of: palmitoyl, stearoyl, lauroyl, and octanoyl. Particularly preferred compounds wherein R' is palmitoyl are shown by Formula (I) and Formula (II) supra.

The lipid moiety can also have the following General Formula (VIII):

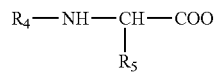

wherein:
$R_4$ is selected from the group consisting of: (i) an alpha-acyl-fatty acid residue consisting of between about 7 and about 25 carbon atoms; (ii) an alpha-alkyl-beta-hydroxy-fatty acid residue; (iii) a beta-hydroxy ester of an alpha-alkyl-beta-hydroxy-fatty acid residue wherein the ester group is preferably a straight chain or branched chain comprising more than 8 carbon atoms; and (iv) a lipoamino acid residue; and
(ii) $R_5$ is hydrogen or the side chain of an amino acid residue.

Preferably, $R_4$ consists of between about 10 and about 20 carbon atoms, and more preferably between about 14 and about 18 carbon atoms.

Optionally, wherein $R_4$ is a lipoamino acid residue, the side-chain of the integers $R_4$ and $R_5$ can form a covalent linkage. For example, wherein $R_4$ comprises an amino acid selected from the group consisting of lysine, ornithine, glutamic acid, aspartic acid, a derivative of lysine, a derivative of ornithine, a derivative of glutamic acid, and a derivative of aspartic acid, then the side chain of that amino acid or derivative is covalently attached, by virtue of an amide or ester linkage, to $R_5$.

Preferably, the structure set forth in General Formula VIII is a lipid moiety selected from the group consisting of: N,N'-diacyllysine; N,N'-diacylornithine; di(monoalkyl)amide or ester of glutamic acid; di(monoalkyl)amide or ester of aspartic acid; a N,O-diacyl derivative of serine, homoserine, or threonine; and a N,S-diacyl derivative of cysteine or homocysteine.

Amphipathic molecules, particularly those having a hydrophobicity not exceeding the hydrophobicity of $Pam_3Cys$ (Formula (I)) are also preferred.

The lipid moieties of Formula (I), Formula (II), Formula (VI) or Formula (VIII) are further modified during synthesis or post-synthetically, by the addition of one or more spacer molecules, preferably a spacer that comprises carbon, and more preferably one or more amino acid residues. These are conveniently added to the lipid structure via the terminal carboxy group in a conventional condensation, addition, substitution, or oxidation reaction. The effect of such a spacer molecule is to separate the lipid moiety from the polypeptide moiety to reduce steric hindrance effects that might otherwise reduce immunogenicity of the lipopeptide product.

Arginine or serine dimers, trimers, tetramers, etc, or alternatively, 6-aminohexanoic acid, are particularly preferred for this purpose.

Preferably, such spacers include a terminal protected amino acid residue to facilitate the later conjugation of the modified lipoamino acid to the polypeptide.

Exemplary modified lipoamino acids produced according to this embodiment are presented as Formulae (III) and (IV), which are readily derived from Formulae (I) and (II), respectively by the addition of a serine homodimer. As exemplified herein, $Pam_3Cys$ of Formula (I), or $Pam_2Cys$ of Formula (II) is conveniently synthesized as the lipoamino acids $Pam_3Cys$-Ser-Ser of Formula (III), or $Pam_2Cys$-Ser-Ser of Formula (IV) for this purpose.

Formula (III):

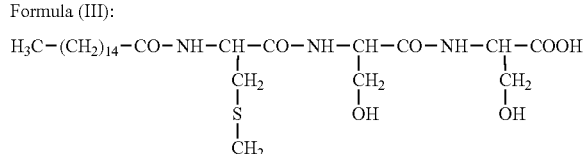

Formula (IV):

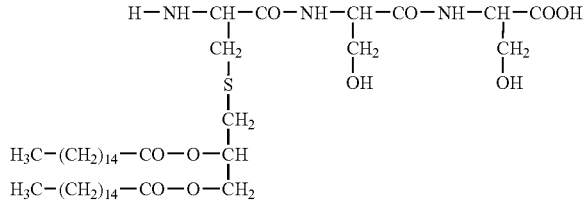

As an alternative to the addition of a spacer to the lipid moiety, the spacer may be added to the epsilon amino group of the internal lysine residue or to the terminal side-chain group of a lysine analog in the polypeptide moiety, either as a short peptide, such as, for example an arginine or serine homodimer, homotrimer, homotetramer, etc, or alternatively, by the sequential addition of amino acid residues, thereby producing a branched polypeptide chain. This approach takes advantage of the modified nature of the epsilon amino group on the internal lysine residue or to the terminal side-chain group of a lysine analog, as appropriate, to achieve specificity in the addition of the spacer. Naturally, to avoid sequential spacer addition, the terminal amino acid residue of the spacer should preferably be protected, such that de-protection can facilitate conjugation of the lipid moiety to the branched polypeptide.

Alternatively, the spacer may be added to a non-modified epsilon amino group of the polypeptide by conventional nucleophilic substitution reaction. However, it is preferred to follow this approach if the polypeptide has an amino acid sequence comprising a single internal lysine or lysine analog residue and a blocked N-terminus.

The lipid moiety is prepared by conventional synthetic means, such as, for example, the methods described in U.S. Pat. Nos. 5,700,910 and 6,024,964, or alternatively, the method described by Wiesmuller et al., *Hoppe Seylers Zur Physiol. Chem.* 364, 593 (1983), Zeng et al., *J. Pept. Sci* 2, 66 (1996), Jones et al., *Xenobiotica* 5, 155 (1975), or Metzger et al., *Int. J. Pept. Protein Res.* 38, 545 (1991). Those skilled in the art will be readily able to modify such methods to achieve the synthesis of a desired lipid for use conjugation to a polypeptide.

Combinations of different lipids are also contemplated for use in the lipopeptides of the invention. For example, one or two myristoyl-containing lipids or lipoamino acids are attached via internal lysine or lysine analog residues to the polypeptide moiety, optionally separated from the polypeptide by a spacer. Other combinations are not excluded.

The lipopeptides of the invention are readily modified for diagnostic purposes. For example, it is modified by addition of a natural or synthetic hapten, an antibiotic, hormone, steroid, nucleoside, nucleotide, nucleic acid, an enzyme, enzyme substrate, an enzyme inhibitor, biotin, avidin, polyethylene glycol, a peptidic polypeptide moiety (e.g. tuftsin, polylysine), a fluorescence marker (e.g. FITC, RITC, dansyl, luminol or coumarin), a bioluminescence marker, a spin label, an alkaloid, biogenic amine, vitamin, toxin (e.g. digoxin, phalloidin, amanitin, tetrodotoxin), or a complex-forming agent.

As exemplified herein, highly immunogenic and soluble lipopeptides are provided comprising $Pam_3Cys$ of Formula (I), or $Pam_2Cys$ of Formula (II) or $Ste_2Cys$ or $Lau_2Cys$ or $Oct_2Cys$ conjugated via the epsilon amino group of an internal lysine residue of a polypeptide that comprises: (i) the amino acid sequence of a $CD4^+$ T-helper epitope derived from the light chain of influenza virus hemagglutinin (Jackson et al. *Virol.* 198, 613-623, 1994; i.e. amino acid sequence GALNNRFQIKGVELKS; SEQ ID NO:1) or a peptide derived from the CDV-F protein (SEQ ID NO: 24); (ii) a B-cell epitope-containing peptide comprising an amino acid sequence selected from the group consisting of the amino acid sequence of luteinising hormone-releasing hormone (LHRH; Fraser et al., *J. Endocrinol.* 63, 399 (1974); Fraser and Baker, *J. Endocrinol.* 77, 85 (1978); i.e. "LHRH 1-10", amino acid sequence EHWSYGLRPG; SEQ ID NO: 2; "LHRH 2-10", amino acid sequence HWSYGLRPG; SEQ ID NO: 3; or "LHRH 6-10", amino acid sequence GLRPG; SEQ ID NO: 4), Group A *Streptococcus* (GAS) M protein (i.e., SEQ ID NO: 101), and pentagastrin (i.e., SEQ ID NO: 102); (iii) a lysine residue positioned between said $CD4^+$ T-helper epitope and said B-cell epitope; and optionally (iv) a lysine residue positioned within said $CD4^+$ T-helper epitope.

Preparation of Lipopeptides

A second aspect of the invention provides a method of producing a lipopeptide comprising:

(i) producing a polypeptide comprising an amino acid sequence that comprises:
  (a) the amino acid sequence of a T helper cell (Th) epitope and the amino acid sequence of a B cell epitope, wherein said amino acid sequences are different; and
  (b) one or more internal lysine residues or internal lysine analog residues; and
(ii) covalently attaching each of said one or more lipid moieties directly or indirectly to an epsilon-amino group of said one or more internal lysine residues or to the terminal side-chain group of said one or more internal lysine analog residues so as to produce a lipopeptide having the lipid moiety attached to the epsilon amino group of said internal lysine residue or having the lipid moiety attached to the terminal side-chain group of said internal lysine analog residue.

Preferably, the method further comprises production of the lipid moiety.

Conventional chemical syntheses referred to herein are the preferred means for producing the polypeptide moiety and the lipid moiety.

Preferably, the internal lysine residue or internal lysine analog is modified by selective removal of a blocking group (eg: Mtt) from the terminal side-chain group, particularly from the terminal side-chain amino group, so as to permit the addition of an amino acid residue, a spacer or lipid moiety, including a lipoamino acid, at that position.

For attachment of the lipid to the polypeptide, it is convenient for the functional groups of the polypeptide to be protected in a manner known in the art of peptide synthesis, to ensure that no undesirable reactions at those groups takes place at a significant reaction rate.

By known coupling processes, the polypeptide is synthesized on a solid or soluble carrier, such as a polymer (for example Merrifield resin) and made available for conjugation to a spacer, amino acid, or lipid. For example, the epsilon amino group of the internal lysine or the terminal side-chain group of an internal lysine analog is protected by one of a number of protecting groups. Blocking groups (also called protecting groups or masking groups) are used to protect the amino group of the amino acid having an activated carboxyl group that is involved in the coupling reaction, or to protect the carboxyl group of the amino acid having an acylated amino group that is involved in the coupling reaction. For coupling to occur, a blocking group must be removed without disrupting a peptide bond, or any protecting group attached to another part of the peptide.

For solid phase peptide synthesis, blocking groups that are stable to the repeated treatments necessary for removal of the amino blocking group of the growing peptide chain and for repeated amino acid couplings, are used for protecting the amino acid side-chains. Additionally, the peptide-resin anchorage that protects the C-terminus of the peptide must be protected throughout the synthetic process until cleavage from the resin is required. Accordingly, by the judicious selection of orthogonally protected alpha-amino acids, lipids and/or amino acids are added at desired locations to a growing peptide whilst it is still attached to the resin.

Preferred amino blocking groups are easily removable but sufficiently stable to survive conditions for the coupling reaction and other manipulations, such as, for example, modifications to the side-chain groups. Preferred amino blocking groups are selected from the group consisting of: (i) a benzyloxycarbonyl group (Z or carbobenzoxy) that is removed easily by catalytic hydrogenation at room temperature and ordinary pressure, or using sodium in liquid ammonia and hydrobromic acid in acetic acid; (ii) a t-Butoxycarbonyl group (Boc) that is introduced using t-butoxycarbonyl azide or di-tert-butyldicarbonate and removed using mild acid such as, for example, trifluoroacetic acid (50% TFA in dichloromethane), or HCl in acetic acid/dioxane/ethylacetate; (iii) a 9-fluorenylmethyloxycarbonyl group (Fmoc) that is cleaved under mildly basic, non-hydrolytic conditions, such as, for example, using a primary or secondary amine (e.g. 20% piperidine in dimethyl formamide); (iv) a 2-(4-biphenylyl)propyl(2)oxycarbonyl group (Bpoc); (v) a 2-nitro-phenylsulfenyl group (Nps); and (vi) a dithia-succionyl group (Dts).

Side chain-protecting groups will vary for the functional side chains of the amino acids forming the peptide being synthesized. Side-chain protecting groups are generally based on the Bzl group or the tBu group. Amino acids having alcohols or carboxylic acids in the side-chain are protected as Bzl ethers, Bzl esters, cHex esters, tBu ethers, or tBu esters. Side-chain protection of Fmoc amino acids requires blocking groups that are ideally base stable and weak acid (TFA) labile. For example, the epsilon-amino group of lysine is protected using Mtt (e.g. Fmoc-lysine(Mtt)-OH). Alternatively, a halogenated benzyl derivative such as ClZ is used to protect the lysine side chain should enhanced acid stability be required. The thiol group of Cystine, the imidazole of Histidine, or guanidino group of Arginine, generally require specialised protection. Many different protecting groups for peptide synthesis have been described (see The Peptides, Gross et al. eds., Vol. 3, Academic Press, New York, 1981).

The two most widely used protection strategies are the Boc/Bzl- and the Fmoc/tBu-strategies. In Boc/Bzl, Boc is used for amino protection and the side-chains of the various amino acids are protected using Bzl- or cHex-based protecting groups. A Boc group is stable under catalytic hydrogenation conditions and is used orthogonally along with a Z group for protection of many side chain groups. In Fmoc/tBu, Fmoc is used for amino protection and the side-chains are protected with tBu-based protecting groups.

Peptides are lipidated by methods well known in the art. Standard condensation, addition, substitution or oxidation (e.g. disulfide bridge formation or amide bond formation between a terminal amino group on the internal lysine or internal lysine analog with the carboxy terminal group of an incoming amino acid or peptide or lipoamino acid) reactions result in the addition of lipid to the polypeptide.

In an alternative embodiment, a peptide of the present invention for use as an immunogen is produced by chemoselective ligation or chemical conjugation. Such methods are well-known in the art, and allow for the individual peptide components to be produced by chemical or recombinant means, followed by their chemoselective ligation in an appropriate configuration or conformation or order (e.g. Nardin et al., *Vaccine* 16, 590 (1998); Nardin et al., *J. Immunol.* 166, 481 (2001); Rose et al., *Mol. Immunol.* 32, 1031 (1995); Rose et al., *Bioconjug. Chem.* 7, 552 (1996); and Zeng et al., *Vaccine* 18, 1031 (2000), which are incorporated herein by reference).

Lipopeptide Formulations

The lipopeptide is conveniently formulated in a pharmaceutically acceptable excipient or diluent, such as, for example, an aqueous solvent, non-aqueous solvent, non-toxic excipient, such as a salt, preservative, buffer and the like. Examples of non-aqueous solvents are propylene glycol, polyethylene glycol, vegetable oil and injectable organic esters such as ethyloleate. Aqueous solvents include water, alcoholic/aqueous solutions, saline solutions, parenteral vehicles such as sodium chloride, Ringer's dextrose, etc. Preservatives include antimicrobial, anti-oxidants, chelating agents and inert gases. The pH and exact concentration of the various components the pharmaceutical composition are adjusted according to routine skills in the art.

The addition of an extrinsic adjuvant to the lipopeptide formulation, although generally not required, is also encompassed by the invention. Such extrinsic adjuvants include all acceptable immunostimulatory compounds such as, for example, a cytokine, toxin, or synthetic composition. Exemplary adjuvants include IL-1, IL-2, BCG, aluminum hydroxide, N-acetyl-muramyl-L-threonyl-D-isoglutamine (thur-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 1983A, referred to as MTP-PE), lipid A, MPL and RIBI, which contains three components extracted from bacteria, monophosphoryl lipid A, trehalose dimycolate and cell wall skeleton (MPL-TDM+CWS) in a 2% squalene/Tween 80 emulsion.

It may be desirable to co-administer biologic response modifiers (BRM) with the lipopeptide, to down regulate suppressor T cell activity. Exemplary BRM's include, but are not limited to, Cimetidine (CIM; 1200 mg/d) (Smith/Kline, PA, USA); Indomethacin (IND; 150 mg/d) (Lederle, NJ, USA); or low-dose Cyclophosphamide (CYP; 75, 150 or 300 mg/m.sup.2) (Johnson/Mead, NJ, USA).

Use of the Lipopeptide in Immunization

The novel lipopeptides of the invention differ in essential aspects from known lipopeptide conjugates of antigens in their enhanced solubility and immunogenicity, and their ability to elicit immune responses without the administration of additional adjuvant. Accordingly, a particular utility of the lipopeptides of the present invention is in the fields of antibody production, synthetic vaccine preparation, diagnostic methods employing antibodies and antibody ligands, and immunotherapy for veterinary and human medicine.

More particularly, the lipopeptide of the present invention induces the specific production of a high titer antibody against the B cell epitope moiety when administered to an animal subject, without any requirement for an adjuvant to achieve a similar antibody titer. This utility is supported by the enhanced maturation of dendritic cells following administration of the subject lipopeptides (i.e. enhanced antigen presentation compared to lipopeptides having N-terminally coupled lipid).

Accordingly, a third aspect of the invention provides a method of eliciting the production of antibody against an antigenic B cell epitope comprising administering an isolated lipopeptide comprising a polypeptide conjugated to one or more lipid moieties to said subject for a time and under conditions sufficient to elicit the production of antibodies against said antigenic B cell epitope, wherein:

(i) said polypeptide comprises:
  (a) the amino acid sequence of a T helper cell (Th) epitope and the amino acid sequence of a B cell epitope, wherein said amino acid sequences are different; and
  (b) one or more internal lysine residues or internal lysine analog residues for covalent attachment of each of said lipid moieties via an epsilon-amino group of said internal lysine or via a terminal side-chain group of said internal lysine analog; and (ii) each of said one or more lipid moieties is covalently attached directly or indirectly to an epsilon-amino group of said one or more internal lysine residues or to a terminal side-chain group of said one or more internal lysine analog residues.

The effective amount of lipopeptide used in the production of antibodies varies upon the nature of the immunogenic B cell epitope, the route of administration, the animal used for immunization, and the nature of the antibody sought. All such variables are empirically determined by art-recognized means.

Reference herein to antibody or antibodies includes whole polyclonal and monoclonal antibodies, and parts thereof, either alone or conjugated with other moieties. Antibody parts include Fab and F(ab)$_2$ fragments and single chain antibodies. The antibodies may be made in vivo in suitable laboratory animals, or, in the case of engineered antibodies (Single Chain Antibodies or SCABS, etc) using recombinant DNA techniques in vitro.

In accordance with this aspect of the invention, the antibodies may be produced for the purposes of immunizing the subject, in which case high titer or neutralizing antibodies that bind to the B cell epitope will be especially preferred. Suitable subjects for immunization will, of course, depend upon the immunizing antigenic B cell epitope. It is contemplated that the present invention will be broadly applicable to the immunization of a wide range of animals, such as, for example, farm animals (e.g. horses, cattle, sheep, pigs, goats, chickens, ducks, turkeys, and the like), laboratory animals (e.g. rats, mice, guinea pigs, rabbits), domestic animals (cats, dogs, birds and the like), feral or wild exotic animals (e.g. possums, cats, pigs, buffalo, wild dogs and the like) and humans.

Alternatively, the antibodies may be for commercial or diagnostic purposes, in which case the subject to whom the lipopeptide is administered will most likely be a laboratory or farm animal. A wide range of animal species are used for the production of antisera. Typically the animal used for production of antisera is a rabbit, a mouse, rat, hamster, guinea pig, goat, sheep, pig, dog, horse, or chicken.

Because of the relatively large blood volume of rabbits, a rabbit is a preferred choice for production of polyclonal antibodies. However, as will be known to those skilled in the art, larger amounts of immunogen are required to obtain high antibodies from large animals as opposed to smaller animals such as mice. In such cases, it will be desirable to isolate the antibody from the immunized animal.

Preferably, the antibody is a high titer antibody. By "high titer" means a sufficiently high titer to be suitable for use in diagnostic or therapeutic applications. As will be known in the art, there is some variation in what might be considered "high titer". For most applications a titer of at least about $10^3$-$10^4$ is preferred. More preferably, the antibody titer will be in the range from about $10^4$ to about $10^5$, even more preferably in the range from about $10^5$ to about $10^6$.

More preferably, in the case of B cell epioptes from pathogens, viruses or bacteria, the antibody is a neutralizing antibody (i.e. it is capable of neutralizing the infectivity of the organism from which the Bcell epitope is derived).

To generate antibodies, the lipopeptide, optionally formulated with any suitable or desired carrier, adjuvant, BRM, or pharmaceutically acceptable excipient, is conveniently administered in the form of an injectable composition. Injection may be intranasal, intramuscular, sub-cutaneous, intravenous, intradermal, intraperitoneal, or by other known route. The lipopeptides of the present invention have demonstrated efficacy when administered Intranasally. For intravenous injection, it is desirable to include one or more fluid and nutrient replenishers. Means for preparing and characterizing antibodies are well known in the art. (See, e.g., ANTIBODIES: A LABORATORY MANUAL, Cold Spring Harbor Laboratory, 1988, incorporated herein by reference).

The efficacy of the lipopeptide in producing an antibody is established by immunizing an animal, for example, a mouse, rat, rabbit, guinea pig, dog, horse, cow, goat or pig, with a formulation comprising the lipopeptide, and then monitoring the immune response to the B cell epitope, as described in the Examples. Both primary and secondary immune responses are monitored. The antibody titer is determined using any conventional immunoassay, such as, for example, ELISA, or radio immunoassay.

The production of polyclonal antibodies may be monitored by sampling blood of the immunized animal at various points following immunization. A second, booster injection, may be given, if required to achieve a desired antibody titer. The process of boosting and titering is repeated until a suitable titer is achieved. When a desired level of immunogenicity is obtained, the immunized animal is bled and the serum isolated and stored, and/or the animal is used to generate monoclonal antibodies (Mabs).

For the production of monoclonal antibodies (Mabs) any one of a number of well-known techniques may be used, such as, for example, the procedure exemplified in U.S. Pat. No. 4,196,265, incorporated herein by reference.

For example, a suitable animal will be immunized with an effective amount of the lipopeptide of the invention and under conditions sufficient to stimulate antibody producing cells. Rodents such as mice and rats are preferred animals, however, the use of rabbit, sheep, or frog cells is also possible. The use of rats may provide certain advantages, but mice are preferred, with the BALB/c mouse being most preferred as the most routinely used animal and one that generally gives a higher percentage of stable fusions.

Following immunization, somatic cells capable of producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer removed. Spleen lymphocytes are obtained by homogenizing the spleen with a syringe. Typically, a spleen from an immunized mouse contains approximately $5 \times 10^7$ to $2 \times 10^8$ lymphocytes.

The B cells from the immunized animal are then fused with cells of an immortal myeloma cell, generally derived from the same species as the animal that was immunized with the lipopeptide formulation. Myeloma cell lines suited for use in hybridoma-producing fusion procedures preferably are non-antibody-producing, have high fusion efficiency and enzyme deficiencies that render then incapable of growing in certain selective media which support the growth of only the desired fused cells, or hybridomas. Any one of a number of myeloma cells may be used and these are known to those of skill in the art (e.g. murine P3-X63/Ag8, X63-Ag8.653, NS1/1.Ag 4 1, Sp210-Ag14, FO, NSO/U, MPC-11, MPC11-X45-GTG 1.7 and S194/5XX0; or rat R210.RCY3, Y3-Ag 1.2.3, IR983F and 4B210; and U-266, GM1500-GRG2, LICR-LON-HMy2 and UC729-6). A preferred murine myeloma cell is the NS-1 myeloma cell line (also termed P3-NS-1-Ag4-1), which is readily available from the NIGMS Human Genetic Mutant Cell Repository under Accession No. GM3573. Alternatively, a murine myeloma SP2/0 non-producer cell line which is 8-azaguanine-resistant is used.

To generate hybrids of antibody-producing spleen or lymph node cells and myeloma cells, somatic cells are mixed with myeloma cells in a proportion between about 20:1 to about 1:1, respectively, in the presence of an agent or agents (chemical or electrical) that promote the fusion of cell membranes. Fusion methods using Sendai virus have been described by Kohler and Milstein, *Nature* 256, 495-497, 1975; and Kohler and Milstein, *Eur. J. Immunol.* 6, 511-519, 1976. Methods using polyethylene glycol (PEG), such as 37% (v/v) PEG, are described in detail by Gefter et al., *Somatic Cell Genet.* 3, 231-236, 1977. The use of electrically induced fusion methods is also appropriate.

Hybrids are amplified by culture in a selective medium comprising an agent that blocks the de novo synthesis of nucleotides in the tissue culture media. Exemplary and preferred agents are aminopterin, methotrexate and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT, because only those hybridomas capable of operating nucleotide salvage pathways are able to survive in HAT medium, whereas myeloma cells are defective in key enzymes of the salvage pathway, (e.g., hypoxanthine phosphoribosyl transferase or HPRT), and they cannot survive. B cells can operate this salvage pathway, but they have a limited life span in culture and generally die within about two weeks. Accordingly, the only cells that can survive in the selective media are those hybrids formed from myeloma and B cells.

The amplified hybridomas are subjected to a functional selection for antibody specificity and/or titer, such as, for example, by immunoassay (e.g. radioimmunoassay, enzyme immunoassay, cytotoxicity assay, plaque assay, dot immunobinding assay, and the like).

The selected hybridomas are serially diluted and cloned into individual antibody-producing cell lines, which clones can then be propagated indefinitely to provide MAbs. The cell lines may be exploited for MAb production in two basic ways. A sample of the hybridoma is injected, usually in the peritoneal cavity, into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they are readily obtained in high concentrations. MAbs produced by either means may be further purified, if desired, using filtration, centrifugation and various chromatographic methods such as HPLC or affinity chromatography.

Monoclonal antibodies of the present invention also include anti-idiotypic antibodies produced by methods well-known in the art. Monoclonal antibodies according to the present invention also may be monoclonal heteroconjugates, (i.e., hybrids of two or more antibody molecules). In another embodiment, monoclonal antibodies according to the invention are chimeric monoclonal antibodies. In one approach, the chimeric monoclonal antibody is engineered by cloning recombinant DNA containing the promoter, leader, and variable-region sequences from a mouse anti-PSA producing cell and the constant-region exons from a human antibody gene. The antibody encoded by such a recombinant gene is a mouse-human chimera. Its antibody specificity is determined by the variable region derived from mouse sequences. Its isotype, which is determined by the constant region, is derived from human DNA.

In another embodiment, monoclonal antibodies according to the present invention is a "humanized" monoclonal antibody, produced by techniques well-known in the art. That is, mouse complementary determining regions ("CDRs") are transferred from heavy and light V-chains of the mouse Ig into a human V-domain, followed by the replacement of some human residues in the framework regions of their murine counterparts. "Humanized" monoclonal antibodies in accordance with this invention are especially suitable for use in in vivo diagnostic and therapeutic methods.

As stated above, the monoclonal antibodies and fragments thereof according to this invention are multiplied according to in vitro and in vivo methods well-known in the art. Multiplication in vitro is carried out in suitable culture media such as Dulbecco's modified Eagle medium or RPMI 1640 medium, optionally replenished by a mammalian serum such as fetal calf serum or trace elements and growth-sustaining supplements, e.g., feeder cells, such as normal mouse peritoneal exudate cells, spleen cells, bone marrow macrophages or the like. In vitro production provides relatively pure antibody preparations and allows scale-up to give large amounts of the desired antibodies. Techniques for large scale hybridoma cultivation under tissue culture conditions are known in the art and include homogenous suspension culture, (e.g., in an airlift reactor or in a continuous stirrer reactor or immobilized or entrapped cell culture).

Large amounts of the monoclonal antibody of the present invention also may be obtained by multiplying hybridoma cells in vivo. Cell clones are injected into mammals which are histocompatible with the parent cells, (e.g., syngeneic mice, to cause growth of antibody-producing tumors. Optionally, the animals are primed with a hydrocarbon, especially oils such as Pristane (tetramethylpentadecane) prior to injection.

In accordance with the present invention, fragments of the monoclonal antibody of the invention are obtained from monoclonal antibodies produced as described above, by methods which include digestion with enzymes such as pepsin or papain and/or cleavage of disulfide bonds by chemical reduction.

The monoclonal conjugates of the present invention are prepared by methods known in the art, e.g., by reacting a monoclonal antibody prepared as described above with, for instance, an enzyme in the presence of a coupling agent such as glutaraldehyde or periodate. Conjugates with fluorescein markers are prepared in the presence of these coupling agents, or by reaction with an isothiocyanate. Conjugates with metal chelates are similarly produced. Other moieties to which antibodies may be conjugated include radionuclides such as, for example, $^3$H, $^{125}$I, $^{32}$P, $^{35}$S, $^{14}$C, $^{51}$Cr, $^{36}$Cl, $^{57}$Co, $^{58}$Co, $^{59}$Fe, $^{75}$Se, and $^{152}$Eu. Radioactively labeled monoclonal antibodies of the present invention are produced according to well-known methods in the art. For instance, monoclonal antibodies are iodinated by contact with sodium or potassium iodide and a chemical oxidizing agent such as sodium hypochlorite, or an enzymatic oxidizing agent, such as lactoperoxidase. Monoclonal antibodies according to the invention may be labeled with technetium$^{99}$ by ligand exchange process, for example, by reducing pertechnate with stannous solution, chelating the reduced technetium onto a Sephadex column and applying the antibody to this column or by direct labeling techniques, (e.g., by incubating pertechnate, a reducing agent such as $SNCl_2$, a buffer solution such as sodium-potassium phthalate solution, and the antibody).

Any immunoassay may be used to monitor antibody production by the lipopeptide formulations. Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and Western blotting, dot blotting, FACS analyses, and the like may also be used.

Most preferably, the assay will be capable of generating quantitative results.

For example, antibodies are tested in simple competition assays. A known antibody preparation that binds to the B cell epitope and the test antibody are incubated with an antigen composition comprising the B cell epitope, preferably in the context of the native antigen. "Antigen composition" as used herein means any composition that contains some version of the B cell epitope in an accessible form. Antigen-coated wells of an ELISA plate are particularly preferred. In one embodiment, one would pre-mix the known antibodies with varying amounts of the test antibodies (e.g., 1:1, 1:10 and 1:100) for a period of time prior to applying to the antigen composition. If one of the known antibodies is labeled, direct detection of the label bound to the antigen is possible; comparison to an unmixed sample assay will determine competition by the test antibody and, hence, cross-reactivity. Alternatively, using secondary antibodies specific for either the known or test antibody, one will be able to determine competition.

An antibody that binds to the antigen composition will be able to effectively compete for binding of the known antibody and thus will significantly reduce binding of the latter. The reactivity of the known antibodies in the absence of any test antibody is the control. A significant reduction in reactivity in the presence of a test antibody is indicative of a test antibody that binds to the B cell epitope (i.e., it cross-reacts with the known antibody).

In one exemplary ELISA, the antibodies against the B cell epitope are immobilized onto a selected surface exhibiting protein affinity, such as a well in a polystyrene microtiter plate. Then, a composition containing the B cell epitope is added to the wells. After binding and washing to remove non-specifically bound immune complexes, the bound epitope may be detected. Detection is generally achieved by the addition of a second antibody that is known to bind to the B cell epitope and is linked to a detectable label. This type of ELISA is a simple "sandwich ELISA". Detection may also be achieved by the addition of said second antibody, followed by the addition of a third antibody that has binding affinity for the second antibody, with the third antibody being linked to a detectable label.

Induction of Sterility

An appropriately configured lipopeptide of the present invention comprising an antigenic B cell epitope of a reproductive hormone or a hormone receptor is capable of inducing infertility in a subject.

Accordingly, a further aspect of the invention provides a method of inducing infertility in a subject comprising administering to said subject an isolated lipopeptide comprising a polypeptide conjugated to one or more lipid moieties, wherein:

(i) said polypeptide comprises:
 (a) the amino acid sequence of a T helper cell (Th) epitope and the amino acid sequence of a B cell epitope of a reproductive hormone or hormone receptor, and wherein said amino acid sequences are different; and
 (b) one or more internal lysine residues or internal lysine analog residues for covalent attachment of each of said lipid moieties via an epsilon-amino group of said internal lysine or via a terminal side-chain group of said internal lysine analog; and (ii) each of said one or more lipid moieties is covalently attached directly or indirectly to an epsilon-amino group of said one or more internal lysine residues or to a terminal side-chain group of said one or more internal lysine analog residues; and (iii) said lipopeptide is administered for a time and under conditions sufficient to elicit a humoral immune response against said antigenic B cell epitope.

The lipopeptides may be administered in the form of any convenient lipopeptide formulation as described herein.

By "humoral immune response" means that a secondary immune response is generated against the B cell epitope sufficient to prevent oogenesis, spermatogenesis, fertilization, implantation, or embryo development.

Preferably, the humoral immunity generated includes a sustained level of antibodies against the B cell epitope in the subject. By a "sustained level of antibodies" is meant a sufficient level of circulating antibodies against the B cell epitope to prevent oogenesis, spermatogenesis, fertilization, implantation, or embryo development.

Preferably, antibodies levels are sustained for at least a single reproductive cycle of an immunized female subject, and more preferably for at least about six months or 9 months or 12 months or 2 years.

Preferably, the B cell epitope is derived from the amino acid sequence of luteinising hormone-releasing hormone (LHRH), follicle stimulating hormone (FSH), luteinising hormone (LH), human chorionic gonadotropin (hCG), a zona pellucida protein such as ZP3, or a FSH receptor ZP3a of humans or other mammals, such as pigs.

Particularly preferred B cell epitopes within this category include the C-terminal portion (CTP) of β-hCG; amino acid residues 323-341 of human ZP3; amino acid residues 8-18 or residues 272-283 or residues 319-330 of porcine ZP3a.

Even more preferably, the B cell epitope comprises an amino acid sequence selected from the group consisting of: SEQ ID NO: 2, SEQ ID NO: 3, SEQ ID NO: 4, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, and SEQ ID NO: 84.

The T-helper epitope preferably comprises an amino acid sequence selected from the group consisting of SEQ ID NO: 1, SEQ ID NO: 20, SEQ ID NO: 24, SEQ ID NO: 26 and SEQ ID NO: 44, however any one of SEQ ID Nos: 1 or 18-56 can be used.

In a particularly preferred embodiment of the invention, the T-helper epitope comprises an amino acid sequence as set forth in any one of SEQ ID NO: 1, SEQ ID NO: 20, SEQ ID NO: 24, SEQ ID NO: 26 and SEQ ID NO: 44, and the B-cell epitope comprises an amino acid sequence of LHRH as set forth in SEQ ID NO: 2 or SEQ ID NO: 3 or SEQ ID NO: 4. In accordance with such a preferred embodiment, the polypeptide comprises an amino acid sequence selected from the group consisting of SEQ ID Nos: 5-16, 103 or 104. Also in accordance with this preferred embodiment, it is preferred (albeit not essential) that the lipid moiety comprise a lipoamino acid selected from the group consisting of: (i) $Pam_2Cys$; (ii) $Ste_2Cys$; (iii) $Lau_2Cys$; and (iv) $Oct_2Cys$.

The sustained production of antibodies against LHRH achieved by the lipopeptides of the invention demonstrates the general utility of the subject lipopeptides as an active agent in a vaccine preparation for inducing sterility, or as a contraceptive agent.

Accordingly, a further aspect of the invention provides a contraceptive agent comprising a pharmaceutically acceptable diluent and a lipopeptide comprising an isolated polypeptide conjugated to one or more lipid moieties wherein:
(i) said polypeptide comprises:
(a) the amino acid sequence of a T helper cell (Th) epitope and the amino acid sequence of a B cell epitope of a reproductive hormone or hormone receptor, wherein said amino acid sequences are different; and
(b) one or more internal lysine residues or internal lysine analog residues for covalent attachment of each of said lipid moieties via an epsilon-amino group of said internal lysine or via a terminal side-chain group of said internal lysine analog; and
(ii) each of said one or more lipid moieties is covalently attached directly or indirectly to an epsilon-amino group of said one or more internal lysine residues or to a terminal side-chain group of said one or more internal lysine analog residues.

The vaccine/contraceptive agent of the invention may comprise one or more carriers or excipients or other agents as described herein above under "lipopeptide formulations".

Similarly, administration of the subject vaccine/contraceptive agent is achieved by means described herein above. Preferably, the subject is a human, or an animal subject such as, for example, a farm animal, laboratory animal, domestic animal, feral animal or wild exotic animal.

Immunization Against Group A *Streptococcus*

Group A *streptococcus* (GAS) is the bacterial agent of relatively mild illnesses such as, for example, "strep throat," and impetigo, as well as rarer severe and even life-threatening diseases such as, for example, necrotizing fasciitis and streptococcal toxic shock syndrome. Severe, sometimes life-threatening, GAS disease may occur when bacteria get into parts of the body where bacteria usually are not found, such as the blood, muscle, or the lungs, an infection termed "invasive GAS disease". Two of the most severe forms of invasive GAS disease are necrotizing fasciitis and Streptococcal Toxic Shock Syndrome (STSS). Necrotizing fasciitis destroys muscles, fat, and skin tissue. STSS causes blood pressure to drop rapidly and organs (e.g., kidney, liver, lungs) to fail. About 20% of patients with necrotizing fasciitis and more than half with STSS die. About 10%-15% of patients with other forms of invasive group A streptococcal disease die. There were about 9,400 cases of invasive GAS disease in the United States alone in 1999.

Invasive GAS infections generally occur when the bacteria get past the defenses of the person who is infected, such as, for example, when a person has sores or other breaks in the skin that allow the bacteria to get into the tissue, or when the person's ability to fight off the infection is decreased because of chronic illness or an illness that affects the immune system, including HIV/AIDS. Also, some virulent strains of GAS are more likely to cause severe disease than others. People suffering from chronic illnesses like cancer, diabetes, and kidney dialysis, and those who use medications such as steroids have a higher risk.

As exemplified herein, an appropriately configured lipopeptide of the present invention comprising an antigenic B cell epitope of a Group A *streptococcus* antigen, preferably protein M, is capable of immunizing an animal host against GAS, and more particularly inducing serum IgG, saliva IgA and fecal IgA against the M protein of GAS, and also providing a protective immune response against a subsequent challenge by GAS thereby reducing GAS-induced mortality.

Accordingly, a further aspect of the invention provides a method of inducing an immune response against a Group A *streptococcus* antigen in a subject comprising administering to said subject an isolated lipopeptide comprising a polypeptide conjugated to one or more lipid moieties, wherein:
(i) said polypeptide comprises:
(a) the amino acid sequence of a T helper cell (Th) epitope and the amino acid sequence of a B cell epitope of a Group A *streptococcus* antigen, wherein said amino acid sequences are different; and
(b) one or more internal lysine residues or internal lysine analog residues for covalent attachment of each of said lipid moieties via an epsilon-amino group of said internal lysine or via a terminal side-chain group of said internal lysine analog; and
(ii) each of said one or more lipid moieties is covalently attached directly or indirectly to an epsilon-amino group of said one or more internal lysine residues or to a terminal side-chain group of said one or more internal lysine analog residues; and
(iii) said lipopeptide is administered for a time and under conditions sufficient to elicit a humoral immune response against said antigenic B cell epitope.

The lipopeptides may be administered in the form of any convenient lipopeptide formulation as described herein.

By "humoral immune response" means that a secondary immune response is generated against the B cell epitope sufficient to induce serum IgG, saliva IgA or fecal IgA against a peptide comprising the B-cell epitope, or alternatively or in addition, providing a protective immunity against a subsequent challenge with Group A *streptococcus*.

Preferably, the humoral immunity generated includes a sustained level of antibodies against the B cell epitope in the subject. By a "sustained level of antibodies" is meant a sufficient level of circulating antibodies against the B cell epitope to prevent the spread of infection by a Group A *streptococcus* following a subsequently challenge, and/or reduce morbidity or mortality in a subject that is subsequently challenged with a Group A *streptococcus*.

Preferably, antibodies levels are sustained for at least about six months or 9 months or 12 months or 2 years.

Preferably, the B cell epitope is derived from the amino acid sequence of the M protein of Group A *streptococcus*.

Particularly preferred B cell epitopes within this category include a peptide that comprises the amino acid sequence set forth in SEQ ID NO: 101.

The T-helper epitope preferably comprises an amino acid sequence selected from the group consisting of SEQ ID NO: 1, SEQ ID NO: 20, SEQ ID NO: 24, SEQ ID NO: 26 and SEQ ID NO: 44, however any one of SEQ ID Nos: 1 or 18-56 can be used.

In a particularly preferred embodiment of the invention, the T-helper epitope comprises an amino acid sequence as set forth in SEQ ID NO: 24 and the B-cell epitope comprises an amino acid sequence set forth in SEQ ID NO: 101. In accordance with such a preferred embodiment, the polypeptide comprises an amino acid sequence selected from the group consisting of SEQ ID Nos: 105-108. Also in accordance with this preferred embodiment, it is preferred (albeit not essential) that the lipid moiety comprise a lipoamino acid of Formula (I) or (II), however any lipid as described herein will be useful.

The sustained production of antibodies against the J14 peptide achieved by the lipopeptides of the invention demonstrates the general utility of the subject lipopeptides as an active agent in a vaccine preparation for providing protective immunity against Group A *streptococcus*.

Accordingly, a further aspect of the invention provides a vaccine against Group A *streptococcus* comprising a pharmaceutically acceptable diluent and a lipopeptide comprising an isolated polypeptide conjugated to one or more lipid moieties wherein:
(i) said polypeptide comprises:
   (a) the amino acid sequence of a T helper cell (Th) epitope and the amino acid sequence of a B cell epitope of a Group A *streptococcus* antigen, wherein said amino acid sequences are different; and
   (b) one or more internal lysine residues or internal lysine analog residues for covalent attachment of each of said lipid moieties via an epsilon-amino group of said internal lysine or via a terminal side-chain group of said internal lysine analog; and
(ii) each of said one or more lipid moieties is covalently attached directly or indirectly to an epsilon-amino group of said one or more internal lysine residues or to a terminal side-chain group of said one or more internal lysine analog residues.

The vaccine of the invention may comprise one or more carriers or excipients or other agents as described herein above under "lipopeptide formulations".

Similarly, administration of the subject vaccine is achieved by means described herein above, preferably by an intranasal route. Preferably, the subject is a human, or an animal subject such as, for example, a farm animal, laboratory animal, domestic animal, feral animal or wild exotic animal.

Inhibition or Prevention of Excessive and Unregulated Gastric Acid Secretion

Gastrin is known to stimulate gastric acid secretion by parietal cells, an activity mediated by binding of gastrin to gastrin receptors or cholecystekinin receptors. The terminal four-to-five amino acid residues of gastrin provide the same receptor specificity and activity as the full-length protein. The terminal five amino acid residues of gastrin are termed "pentagastrin". Unregulated gastrin expression or secretion causes hypergastrinemia, which can lead to Zollinger-Ellison syndrome, the formation of gastric and duodenal ulcers, or gastrinoma in the pancreas or duodenum, as a consequence of excessive and unregulated gastric acid secretion. Immunoneutralization of gastrin using antibodies against gastrin is also known to block secretion of gastric acid in response to intragastric secretion of gastrin peptides.

As exemplified herein, an appropriately configured lipopeptide of the present invention comprising an antigenic B cell epitope of a gastrin peptide is capable of immunizing an animal host against gastrin or an effect of excessive gastrin production in a mouse model of other mammals in which inhibition of gastric acid secretion is indicated. The data provided herein demonstrate the general utility of the subject lipopeptides in inducing humoral immunity against gastrin and immunoneutralization of gastrin, to thereby block secretion of gastric acid, in an animal suffering from hypergastrinemia, Zollinger-Ellison syndrome, gastric ulceration or duodenal ulceration due to excessive and unregulated secretion of gastric acid, or to reduce or prevent the formation of gastrin-secreting tumors in the pancreas or duodenum (i.e. the prophylaxis and/or therapy of gastrinoma).

Accordingly, a further aspect of the invention provides a method of inducing an immune response against a gastrin peptide in a subject comprising administering to said subject an isolated lipopeptide comprising a polypeptide conjugated to one or more lipid moieties, wherein:
(i) said polypeptide comprises:
   (a) the amino acid sequence of a T helper cell (Th) epitope and the amino acid sequence of a B cell epitope of a gastrin peptide antigen, wherein said amino acid sequences are different; and
   (b) one or more internal lysine residues or internal lysine analog residues for covalent attachment of each of said lipid moieties via an epsilon-amino group of said internal lysine or via a terminal side-chain group of said internal lysine analog; and
(ii) each of said one or more lipid moieties is covalently attached directly or indirectly to an epsilon-amino group of said one or more internal lysine residues or to a terminal side-chain group of said one or more internal lysine analog residues; and
(iii) said lipopeptide is administered for a time and under conditions sufficient to elicit a humoral immune response against said antigenic B cell epitope.

The lipopeptides may be administered in the form of any convenient lipopeptide formulation as described herein.

By "humoral immune response" means that a secondary immune response is generated against the B cell epitope sufficient to induce serum IgG against a gastrin peptide comprising the B-cell epitope.

Preferably, the humoral immunity generated includes a sustained level of antibodies against the B cell epitope in the subject. By a "sustained level of antibodies" is meant a sufficient level of circulating antibodies against the B cell epitope to prevent excessive or unregulated gastric acid secretion in response to gastrin.

Preferably, antibodies levels are sustained for at least about six months or 9 months or 12 months or 2 years.

Preferably, the B cell epitope is contained within a pentagastrin peptide. Particularly preferred B cell epitopes within this category include a peptide that comprises the amino acid sequence set forth in SEQ ID NO: 102, however the full length gastrin protein or any immunogenic fragment thereof comprising a B-cell epitope may also be used.

The T-helper epitope preferably comprises an amino acid sequence selected from the group consisting of SEQ ID NO: 1, SEQ ID NO: 20, SEQ ID NO: 24, SEQ ID NO: 26 and SEQ ID NO: 44, however any one of SEQ ID Nos: 1 or 18-56 can be used.

In a particularly preferred embodiment of the invention, the T-helper epitope comprises an amino acid sequence as set forth in SEQ ID NO: 24 and the B-cell epitope comprises an amino acid sequence set forth in SEQ ID NO: 102. In accordance with such a preferred embodiment, the polypeptide comprises an amino acid sequence selected from the group consisting of SEQ ID Nos: 109-112. Also in accordance with this preferred embodiment, it is preferred (albeit not essential) that the lipid moiety comprise a lipoamino acid of Formula (I) or (II), however any lipid as described herein will be useful.

The sustained production of antibodies against pentagastrin or gastrin that is achieved by the lipopeptides of the invention demonstrates the general utility of the subject lipopeptides as an active agent in a vaccine preparation for reducing an adverse effect of gastrin in a subject in need thereof.

Accordingly, a further aspect of the invention provides a vaccine against a disease or condition induced by excessive gastrin secretion in a subject comprising a pharmaceutically acceptable diluent and a lipopeptide comprising an isolated polypeptide conjugated to one or more lipid moieties wherein:
(i) said polypeptide comprises:
   (a) the amino acid sequence of a T helper cell (Th) epitope and the amino acid sequence of a B cell epitope of a gastrin peptide antigen, wherein said amino acid sequences are different; and (b) one or more internal lysine residues or internal lysine analog residues for covalent attachment of each of said lipid moieties via an epsilon-amino group of said internal lysine or via a terminal side-chain group of said internal lysine analog; and (ii) each of said one or more lipid moieties is covalently attached directly or indirectly to an epsilon-amino group of said one or more internal lysine residues or to a terminal side-chain group of said one or more internal lysine analog residues.

The vaccine of the invention may comprise one or more carriers or excipients or other agents as described herein above under "lipopeptide formulations".

Similarly, administration of the subject vaccine is achieved by means described herein above. Preferably, the subject is a human.

The present invention is further described with reference to the following non-limiting examples and the drawings.

EXAMPLE 1

Materials and Methods

Chemicals

Unless otherwise stated chemicals were of analytical grade or its equivalent. N,N'-dimethylformamide (DMF), piperidine, trifluoroacetic acid (TFA), O'benzotriazole-N,N,N',N'-tetramethyluronium hexafluorophosphate (HBTU), 1-hydroxybenzotriazole (HOBt) and diisopropylethylamine (DIPEA) and diisopropylcarbodiimide (DIPCDI) were obtained from Auspep Pty. Ltd., Melbourne, Australia and Sigma-Aldrich Pty. Ltd., Castle Hill, Australia. O'benzotriazole-N,N,N',N'-tetramethyluronium tetrafluoroborate (TBTU) was obtained from Bachem, (Bachem AG, Switzerland). Dichloromethane (DCM) and diethylether were from Merck Pty Ltd. (Kilsyth, Australia). Phenol and triisopropylsilane (TIPS) were from Aldrich (Milwaulke, Wis.) and trinitrobenzylsulphonic acid (TNBSA) and diaminopyridine (DMAP) from Fluka; 1,8-diazabicyclo[5.4.0]undec-7-ene (DBU) was obtained from Sigma and palmitic acid was from Fluka.

Synthesis of Lipid Moieties of Formulae (I)

Pam$_3$Cys was prepared according to the method described by Weismuller et al., *Hoppe Seylers Z Physiol Chem* 364, 593 (1983), as modified according to the method described by Zeng et al., *J Pept Sci* 2, :66 (1996). The lipoamino acid Pam$_3$Cys is coupled to the exposed epsilon-amino group of lysine according to the procedure described by Zeng et al. (supra). Briefly, a 2-fold excess of Pam$_3$Cys, TBTU and HOBt was dissolved in DCM and a 3-fold excess of DIPEA added. This solution was then added to the resin-bound peptide to generate the lipopeptide.

Synthesis of Lipid Moieties of Formulae (II)

Pam$_2$Cys and its derivative Fmoc-Pam$_2$Cys-OH were prepared according to the methods described by Jones et al., *Xenobiotica* 5, 155 (1975) and Metzger et al., *Int J Pept Protein Res* 38, 545 (1991).

Synthesis of Lipopeptides

Pam$_2$Cys, Ste$_2$Cys, Oct$_2$Cys, or Lau$_2$Cys were coupled to peptide using a variation of the methods described by Jones et al., Xenobiotica 5, 155 (1975) and Metzger et al., *Int J Pept Protein Res* 38, 545 (1991).

I. Synthesis of S-(2,3-Dihydroxypropyl)cysteine

Triethylamine (6 g, 8.2 ml, 58 mmoles) was added to L-cysteine hydrochloride (3 g, 19 mmole) and 3-bromo-propan-1,2-diol (4.2 g, 2.36 ml, 27 mmole) in water and the homogeneous solution kept at room temperature for 3 days. The solution was reduced in vacuo at 40° C. to a white residue which was boiled with methanol (100 ml), centrifuged and the residue dissolved in water (5 ml). This aqueous solution was added to acetone (300 ml) and the precipitate isolated by centrifugation. The precipitate was purified by several precipitations from water with acetone to give S-(2,3-dihydroxypropyl)cysteine as a white amorphous powder (2.4 g, 12.3 mmol, 64.7%).

II. Synthesis of N-Fluorenylmethoxycarbonyl-S-(2, 3-dihydroxypropyl)cysteine (Fmoc-Dhc-OH)

S-(2,3-dihydroxypropyl)cysteine (2.45 g, 12.6 mmole) was dissolved in 9% sodium carbonate (20 ml). A solution of fluorenylmethoxycarbonyl-N-hydroxysuccinimide (3.45 g, 10.5 mmole) in acetonitrile (20 ml) was added and the mixture stirred for 2 h, then diluted with water (240 ml), and extracted with diethyl ether (25 ml×3). The aqueous phase was acidified to pH 2 with concentrated hydrochloric acid and was then extracted with ethyl acetate (70 ml×3). The extract was washed with water (50 ml×2) and saturated sodium chloride solution (50 ml×2), dried over sodium sulfate and evaporated to dryness. Recrystallisation from ether and ethyl acetate at −20° C. yielded a colourless powder (2.8 g, 6.7 mmole, 63.8%).

III. Coupling of Fmoc-Dhc-OH to Resin-Bound Peptide

Fmoc-Dhc-OH (100 mg, 0.24 mmole) was activated in DCM and DMF (1:1, v/v, 3 ml) with HOBt (36 mg, 0.24 mmole) and DICI (37 ul, 0.24 mmol) at 0° C. for 5 min. The mixture was then added to a vessel containing the resin-bound peptide (0.04 mmole, 0.25 g amino-peptide resin). After shaking for 2 h the solution was removed by filtration and the resin was washed with DCM and DMF (3×30 ml each). The reaction was monitored for completion using the TNBSA test. If necessary a double coupling was performed.

IVa. Palmitoylation of the Two Hydroxy Groups of the Fmoc-Dhc-Peptide Resin

Palmitic acid (204 mg, 0.8 mmole), DICI (154 ul, 1 mmole) and DMAP (9.76 mg, 0.08 mmole) were dissolved in 2 ml of DCM and 1 ml of DMF. The resin-bound Fmoc-Dhc-peptide resin (0.04 mmole, 0.25 g) was suspended in this solution and shaken for 16 h at room temperature. The solution was removed by filtration and the resin was then washed with DCM and DMF thoroughly to remove any residue of urea. The removal of the Fmoc group was accomplished with 2.5% DBU (2×5 mins).

IVb. Stearoylation of the Two Hydroxy Groups of the Fmoc-Dhc-Peptide Resin

Stearic acid (about 0.8 mmole), DICI (154 ul, 1 mmole) and DMAP (9.76 mg, 0.08 mmole) were dissolved in 2 ml of DCM and 1 ml of DMF. The resin-bound Fmoc-Dhc-peptide resin (0.04 mmole, 0.25 g) was suspended in this solution and shaken for 16 h at room temperature. The solution was removed by filtration and the resin was then washed with DCM and DMF thoroughly to remove any residue of urea. The removal of the Fmoc group was accomplished with 2.5% DBU (2×5 mins).

IVc. Lauroylation of the Two Hydroxy Groups of the Fmoc-Dhc-Peptide Resin

Lauric acid (about 0.8 mmole), DICI (154 ul, 1 mmole) and DMAP (9.76 mg, 0.08 mmole) were dissolved in 2 ml of DCM and 1 ml of DMF. The resin-bound Fmoc-Dhc-peptide resin (0.04 mmole, 0.25 g) was suspended in this solution and shaken for 16 h at room temperature. The solution was removed by filtration and the resin was then washed with DCM and DMF thoroughly to remove any residue of urea. The removal of the Fmoc group was accomplished with 2.5% DBU (2×5 mins).

IVd. Octanoylation of the Two Hydroxy Groups of the Fmoc-Dhc-Peptide Resin

Octanoic acid (about 0.8 mmole), DICI (154 ul, 1 mmole) and DMAP (9.76 mg, 0.08 mmole) were dissolved in 2 ml of DCM and 1 ml of DMF. The resin-bound Fmoc-Dhc-peptide resin (0.04 mmole, 0.25 g) was suspended in this solution and shaken for 16 h at room temperature. The solution was removed by filtration and the resin was then washed with DCM and DMF thoroughly to remove any residue of urea. The removal of the Fmoc group was accomplished with 2.5% DBU (2×5 mins).

Peptide Synthesis

The general procedure used for the peptide synthesis has been described by Jackson et al., Vaccine 18, 355 (1999). To enable lipid attachment between the CD4$^+$ T cell epitope and B-cell epitope, Fmoc-lysine(Mtt)-OH was inserted at a point between the two epitopes in the approximate centre of the resin-bound peptide. If lipid was to be added to another position within the peptide, such as, for example, the Lys-14 residue of SEQ ID NO: 24, then the Fmoc-lysine(Mtt)-OH was also inserted at that position. Following completion of peptide synthesis the Mtt group was removed by continual flow washing with 1% TFA in dichloromethane over a period of 30-45 mins to expose the epsilon amino group of the lysine residue. Two serine residues were coupled to this epsilon amino group in the case where two serine residues were used as spacer. Alternatively, two arginine residues were coupled to this epsilon amino group in the case where two arginine residues were used as spacer. Alternatively, 6-aminohexanoic acid was coupled to this epsilon amino group. The subsequent coupling of the lipid moiety, such as, for example, Pam$_3$Cys, Pam$_2$Cys, Ste$_2$Cys, Oct$_2$Cys, or Lau$_2$Cys was described above.

All resin-bound peptide constructs were cleaved from the solid phase support with reagent B (88% TFA, 5% phenol, 2% TIPS, 5% water) for 2 hr, and purified by reversed phase chromatography as described by Zeng et al., Vaccine 18, 1031 (2000).

Analytical reversed phase high pressure liquid chromatography (RP-HPLC) was carried out using a Vydac C4 column (4.6×250 mm) installed in a Waters HPLC system and developed at a flow rate of 1 ml/min using 0.1% TFA in H$_2$O and 0.1% TFA in CH$_3$CN as the limit solvent. All products presented as a single major peak on analytical RP-HPLC and had the expected mass when analysed by MALDI-TOF mass spectrometry on a Bruker BIFLEX instrument equipped with delayed ion extraction. The final quantitation of the immunogens was done by measuring the absorption at 280 nm exploiting the presence of a tryptophan and a tyrosine residue in the peptide constructs (molar extinction coefficient of 6.6× 10$^3$).

To investigate the effect of serine by incorporating two residues between the peptide and lipid moieties of the Pam$_3$Cys-containing peptides and Pam$_2$Cys-containing peptides, two serine residues were added sequentially to the peptide prior to covalent attachment of the lipid moiety (the structures of which are shown in FIG. 1). Summaries of their characteristics, carried out by analytical RP-HPLC and mass spectrometry, are presented in Tables 1 and 2.

Immunization Protocols

Groups of five female BALB/c mice, 6 to 8 weeks old, were inoculated at day 0 and again on day 28. Alternatively, female outbred Quackenbush mice, 4-6 weeks old, were immunized intranasally and provided with boosts as per the primary immunization at 21-day intervals. For subcutaneous (s.c.) inoculations (100 µl volume per dose), lipopeptide constructs were prepared in saline and non-lipidated peptides formulated as an emulsion in an equal volume of complete Freund's adjuvant (CFA) for the primary injection or incomplete Freund's adjuvant for the secondary inoculation. For intranasal (i.n.) inoculations, 50 µl of peptide in saline were applied to the nares of mice anaesthetized with penthrane for inhalation. Sera were prepared from blood taken at 4 weeks after the primary inoculation and two weeks after the secondary inoculation, or alternatively, from tail bleeds seven days following the final immunization.

Enzyme-Linked Immunosorbent Assays (ELISA)

ELISA assays were carried out on serum samples as described essentially by Ghosh et al., Int Immun. 11, 1103, (1999), using the immunizing antigen (e.g., LHRH, J14 or pentagastrin) as the coating antigen. The titres of antibody were expressed as the reciprocal of the highest dilution of serum to achieve an OD of 0.2, which represents approximately 5 times the background binding in the absence of antibody. The isotype of antibodies specific for LHRH or J14 was determined using rabbit antisera directed against mouse IgM, IgG1, IgG2a, IgG2b, IgG3 or IgA (ICN Pharmaceuticals Inc., Costa Mesa, Calif.) as previously described by Ghosh et al., Int Immun. 11, 1103, (1999).

Fertility Studies

After being inoculated with peptide immunogen and following exposure to male mice, female mice were tested for their ability to drop litters. A group of female mice immunized with saline in CFA was used as a control. A male mouse was introduced into a cage in which two or three female mice were kept and male mice rotated between each cage to expose each group of female mice to every male. Males and females were kept together for a total of 3 weeks at the end of which time the males were removed and the females kept under observation.

TABLE 1

HPLC elution and mass characteristics of peptide vaccines based upon influenza virus hemagglutinin T-helper epitope (SEQ ID NO: 1) and LHRH B-cell epitope (SEQ ID NO: 2).

| [1]Peptide construct | [1]Retention time (min) | Expected mass (Da) | [2]Experimentally determined mass (Da) |
|---|---|---|---|
| [Th]-[B] | 26.3 | 2957.1 | 2957.3 |
| [Th]-Lys-[B] | 26.0 | 3085.5 | 3084.7 |
| Pam$_3$Cys-Ser-Ser-[Th]-[B] | 51.5 | 4022.4 | 4020.8 |
| Pam$_2$Cys-Ser-Ser-[Th]-[B] | 41.8 | 3785.1 | 3785.5 |
| Pam$_2$Cys-[Th]-[B] | 40.7 | 3609.3 | 3605.7 |
| [Th]-Lys(Pam$_3$Cys)-[B] | 50.4 | 3977.4 | 3969.5 |

TABLE 1-continued

HPLC elution and mass characteristics of peptide vaccines based upon influenza virus hemagglutinin T-helper epitope (SEQ ID NO: 1) and LHRH B-cell epitope (SEQ ID NO: 2).

| [1]Peptide construct | [1]Retention time (min) | Expected mass (Da) | [2]Experimentally determined mass (Da) |
|---|---|---|---|
| [Th]-Lys(Pam$_2$Cys)-[B] | 40.7 | 3739.5 | 3739.6 |
| [Th]-Lys(Pam$_2$Cys-Ser-Ser-)-[B] | 40.3 | 3913.5 | 3912.1 |

[1]Reversed phase chromatography was carried out on Vydac C4 column (4.6 × 250 mm) installed in a Waters HPLC system and developed at a flow rate of 1 ml/min using 0.1% TFA in H$_2$O and 0.1% TFA in CH$_3$CN as the limit solvent.
[2]Mass spectrometry was carried out using a Bruker Biflex MALDI-TOF instrument equipped with delayed ion extraction. Analysis was carried out in the linear mode.

TABLE 2

HPLC elution and mass characteristics of peptide vaccines based upon CDV-F P25 T-helper epitope (SEQ ID NO: 24) and pentagastrin B-cell epitope (SEQ ID NO: 102).

| [1]Peptide construct | [1]Retention time (min) | Expected mass (Da) | [2]Experimentally determined mass (Da) |
|---|---|---|---|
| [Th]-Lys-[B] | 31.4 | 2621.5 | 2620.7 |
| Pam$_2$Cys-Ser-Ser-[Th]-[B] | 54.9 | 3449.7 | 3450.3 |
| [Th]-Lys(Pam$_2$Cys-Ser-Ser-)-[B] | 53.9 | 3505.7 | 3506.7 |

[1]Reversed phase chromatography was carried out on Vydac C4 column (4.6 × 300 mm) installed in a Waters HPLC system and developed at a flow rate of 1 ml/min using 0.1% TFA in H$_2$O and 0.1% TFA in CH$_3$CN as the limit solvent.
[2]Mass spectrometry was carried out using an Agilent 110 LC/MSD ion trap mass spectrometer.

Dendritic Cell Culture

Dendritic cells (DC) were cultured in medium based on complete IDDM. This consisted of Iscove's Modified Dulbecco's Medium (IMDM) containing 25 mM HEPES and without alpha-thioglycerol or L-glutamine (JRH Bioscience, Lenexa, USA), supplemented with 10% (v/v) heat inactivated (56° C., 30 min) foetal calf serum (CSL Ltd., Parkville, Victoria, Australia), gentamicin (24 µg/mL), glutamine (2 mM), sodium pyruvate (2 mM), penicillin (100 IU/mL), streptomycin (180 µg/mL) and 2-mercaptoethanol (0.1 mM). For DC generation complete IMDM was further supplemented with 30% supernatant from cultured NIH/3T3 cells and 5% GM-CSF in the form of a supernatant from Ag8653 cells transfected with the GM-CSF gene (DC medium).

The culture method for immature dendritic cells was adapted from Winzler et al., J. Exp Med. 185, 317 (1997). Spleen cells from a BALB/c mouse were seeded at 1.5×10$^6$ cells per 55 mm dish (Techno-Plas, S.A., Australia) in 3 ml DC medium and incubated at 37° C. with 5% CO$_2$. All the equipment used for culturing was pyrogen free. The medium was changed every 4 days and all cells returned to the dish. On day 12, both suspended and weakly adherent cells were collected by forcefully pipetting and then aspirating the medium. The procedure was repeated with 2 ml of PBS. The remaining strongly adherent cells were discarded. The collected cells were pelleted by centrifugation and reseeded into a new dish. Cells were subsequently maintained on a 4 day alternating cycle of media change and passage. After 1 month of continuous culturing, the floating and semi-adherent cells took on the appearance and staining characteristics of immature DC and are referred to as D1 cells. Under these passage conditions the majority of cultured D1 cells maintain an immature phenotype characterized by an intermediate expression level of cell surface MHC class II molecules.

Flow Cytometric Analysis of D1 Cells

D1 cells (1×10$^5$ cells per sample) were seeded in a new Petri dish with 1 mL of DC media and incubated with 0.0045 nmole of lipopeptide, dissolved in complete IMDM medium. Lipopolysaccharide purified from E. coli serotype O111:B4 (Difco, Detroit, Mich., USA, a kind gift from Dr. E. Margot Anders, Department of Microbiology and Immunology, University of Melbourne) was used at 5 µg/mL as a positive control for DC maturation. After overnight incubation, the cells were harvested and washed once with PBS with 1% FCS. To prevent non-specific binding to FCγRII/III, the cells were pre-incubated with 20 µL of normal mouse serum for 5 mins at room temperature. The cells were then exposed to FITC-conjugated monoclonal antibody 14-4-4S (IgG$_{2a}$, anti-I-E$^{k,d}$; Ozato et al., J. Immunol., 124, 533, 1980) for 30 min on ice. Monoclonal antibody 36/1 (Brown et al., Arch Virol 114, 1 1990), which is specific for the hemagglutinin of influenza virus, was used as an isotype control. All antibodies were used at 2.5 µg/mL. The samples were washed once with PBS containing 1% FCS and fixed with PBS containing 4% paraformaldehyde on ice for 15 minutes. Flow cytometry analysis was performed using a FACSort (Becton Dickinson, San Jose, USA) and the data were analysed using FlowJo software (Tree Star, Inc., San Carlos, Calif., USA).

EXAMPLE 2

Studies on Lipopeptides Comprising LHRH B Cell Epitopes

Solubility Properties of Lipopeptides Comprising LHRH

Visual inspection of the different lipopeptide preparations comprising LHRH showed that they differed markedly in their solubilities (FIG. 2). Enhanced solubility was most evident in those cases where lipid was attached between the two epitopes at the approximate centre of the molecule. The lipopeptides designated [Th]-Lys(Pam$_2$Cys)-[B] and [Th]-Lys(Pam$_3$Cys)-[B] were soluble in saline at concentrations of at least 8 mg/ml (no higher concentrations were examined), whereas constructs in which lipid was attached to the N-terminus of the sequence formed opalescent solutions at concentrations as low as 0.25 mg/ml.

Efforts to further enhance the solubility of peptides with N-terminally linked lipid by the incorporation of two hydrophilic serine residues between the lipid and peptide moieties (i.e. Pam$_2$Cys-Ser-Ser-[Th]-[B] and Pam$_3$Cys-Ser-Ser-[Th]-[B]), proved unsuccessful. In fact the lipopeptide Pam$_3$Cys-Ser-Ser-[Th]-[B] was so insoluble that it could not be purified by RP-HPLC under conditions used for the other lipopeptides. We considered that the insoluble nature of this construct would prevent it from being considered as a viable proposition for manufacture as a vaccine.

Immunogenicity of Lipopeptides Comprising LHRH B Cell Epitopes

The three lipopeptides designated Pam$_2$Cys-Ser-Ser-[Th]-[B], [Th]-Lys(Pam$_2$Cys)-[B] and [Th]-Lys(Pam$_3$Cys)-[B], when administered s.c. in saline induced high levels of anti-LHRH antibody. In fact, antibody titres induced after two doses of these lipopeptides were similar to those obtained with [Th]-[B] or [Th]-Lys-[B] when administered in CFA (FIG. 3). The titres of anti-LHRH antibodies in sera of mice that had received Pam$_3$Cys-Ser-Ser-[Th]-[B] or Pam$_2$Cys-[Th]-[B] were slightly lower. The two soluble lipopeptides [Th]-Lys(Pam$_2$Cys)-[B], [Th]-Lys(Pam$_3$Cys)-[B] induced Antibody levels were followed up to 7 months after the second dose of peptide vaccine. The titres of anti-LHRH antibody present in lipopeptide-primed mice and in mice primed with non lipidated peptide administered in CFA decrease between 4 and 20 fold during a 26 week period. Three months following the secondary inoculation a fertility study carried out on all mice yielded similar results to the 2 week post-immunization trial. Mice that had received the soluble lipopeptides, [Th]-Lys(Pam$_2$Cys)-[B] or [Th]-Lys(Pam$_3$Cys)-[B], in saline or the non-lipidated [Th]-[B] and [Th]-Lys-[B] in CFA were still infertile.

TABLE 3

Anti-LHRH antibody titres and incidence of pregnancy following inoculation with peptide constructs

| [1]Inoculum | [2]Mean anti-LHRH titres (log$_{10}$) weeks following second dose | | | | | Incidence of pregnancy | |
|---|---|---|---|---|---|---|---|
| | 2 weeks | 7 weeks | 10 weeks | 20 weeks | 28 weeks | 2 weeks after 2$^{nd}$ Dose | 13 weeks after 2$^{nd}$ Dose |
| Pam$_2$Cys-[Th]-[B] | 4.24 ± 0.60 | 3.38 ± 0.18 | 3.34 ± 0.97 | 3.18 ± 0.63 | 3.16 ± 0.53 | 2/5 | 3/5 |
| Pam$_3$Cys-Ser-Ser-[Th]-[B] | 3.36 ± 0.23 | 3.12 ± 0.16 | 3.04 ± 0.24 | 2.78 ± 0.19 | 2.75 ± 0.23 | 2/5 | 0/5 |
| Pam$_2$Cys-Ser-Ser-[Th]-[B] | 4.78 ± 0.18 | 3.96 ± 0.10 | 3.80 ± 0.16 | 3.52 ± 0.25 | 3.48 ± 0.25 | 1/5 | 2/5 |
| [Th]-Lys(Pam$_3$Cys)-[B] | 4.48 ± 0.62 | 4.18 ± 0.43 | 4.06 ± 0.38 | 3.86 ± 0.54 | 3.75 ± 0.48 | 0/5 | 0/5 |
| [Th]-Lys(Pam$_2$Cys)-[B] | 4.68 ± 0.40 | 3.96 ± 0.34 | 3.94 ± 0.38 | 3.78 ± 0.21 | 3.70 ± 0.29 | 0/5 | 0/5 |
| [Th]-[B] | 4.92 ± 0.32 | 4.32 ± 0.32 | 4.28 ± 0.32 | 4.06 ± 0.36 | 3.98 ± 0.35 | 0/5 | 0/5 |
| [Th]-Lys-[B] | 4.70 ± 0.18 | 4.36 ± 0.15 | 4.24 ± 0.16 | 4.12 ± 0.20 | 3.82 ± 0.08 | 0/5 | 0/5 |
| [Th]-[B] + Pam$_3$Cys-Ser-Lys$_4$ (1:5 admixture) | <2 | ND | ND | ND | ND | 5/5 | ND |
| Saline | <2 | ND | ND | ND | ND | 5/5 | 3/5 |

[1][Th]-[B], [Th]-Lys-[B] and saline were each administered in CFA, all other peptide constructs were administered in saline. The dose of each was 20 nmoles administered subcutaneously.
[2]Titres represent the geometric means of groups of five female BALB/c mice.

10 to 100-fold higher levels of anti-LHRH antibody following the primary inoculation than did the other less soluble lipopeptide constructs. Two groups of five mice receiving [Th]-[B] admixed with Pam$_3$Cys-Ser-(Lys)$_4$ in the ratio 1:1 or 1:5 did not elicit significant levels of anti-LHRH antibody, a finding that contrasts with other results reported using Pam$_3$Cys-Ser-(Lys)$_4$ as an adjuvant (Jung, G., and W. G. Bessler. (1995) In: "*Immunological recognition of peptides in medicine and biology*", N. D. Zegers, W. J. A. Boersma, and E. Claassen, eds. CRC Press, Boca, N.Y., London, Tokyo, p. 159).

The results of the fertility study carried out two weeks after the second inoculation with the various lipopeptides are shown in Table 3.

None of the mice that received either of the two soluble lipopeptide constructs, [Th]-Lys(Pam$_2$Cys)-[B] or [Th]-Lys(Pam$_3$Cys)-[B], administered in saline or the two non-lipidated constructs [Th]-[B] or [Th]-Lys-[B] administered in CFA, became pregnant. One mouse from the group that received Pam$_2$Cys-Ser-Ser-[Th]-[B], and two animals from the groups that received Pam$_3$Cys-Ser-Ser-[Th]-[B] or Pam$_2$Cys-[Th]-[B] dropped litters. All members of control groups of mice that received saline in CFA or the peptide [Th]-[B] co-admixed with Pam$_3$Cys-S-(Lys)$_4$ dropped litters.

Pam$_2$Cys is a More Potent Adjuvant than Pam$_3$Cys

The results presented in FIG. 3 and Table 2 indicate that the two branched lipopeptides [Th]-Lys(Pam$_2$Cys)-[B] and [Th]-Lys(Pam$_3$Cys)-[B] were not only more soluble but also elicited higher antibody titres, particularly in the primary antibody response, than did the immunogens Pam$_2$Cys-[Th]-[B], Pam$_2$Cys-Ser-Ser-[Th]-[B] and Pam$_3$Cys-Ser-Ser-[Th]-[B].

To examine this further, we investigated the effect of decreasing the dose on the immunogenicity of [Th]-Lys(Pam$_2$Cys)-[B] and [Th]-Lys(Pam$_3$Cys)-[B]. At doses of 10 nmole and 1 nmole, [Th]-Lys(Pam$_2$Cys)-[B] induced higher antibody titres than did [Th]-Lys(Pam$_3$Cys)-[B] (Table 4). A more striking difference was observed in the mating trial; 1 of 5 and 0 of 5 mice receiving 10 and 1 nmole [Th]-Lys(Pam$_2$Cys)-[B], respectively, dropped litters whereas 3 of 5 and 5 of 5 mice receiving [Th]-Lys(Pam3Cys)-[B] at these doses dropped litters (Table 4). These results indicate that Pam$_2$Cys-containing peptides are better immunogens than Pam$_3$Cys-containing peptides.

The effect of including two additional serine residues into the Pam$_2$Cys-containing immunogens had little or no effect on the fertility status of animals although there was an improvement in the antibody titres that were generated following the second dose (Table 4).

TABLE 4

Anti-LHRH antibody titres and fertility status of mice inoculated with different doses of peptide vaccines.

| [1]Inoculum | Mean anti-LHRH antibody titre ($\log_{10}$) 2 weeks following second dose | [2]Pregnancy status (No. of animals per group that dropped litters) |
|---|---|---|
| [Th]-Lys(Pam3Cys)-[B] 10 nmole | 3.76 ± 0.36 | 3/5 |
| [Th]-Lys(Pam3Cys)-[B] 1 nmole | 3.22 ± 0.51 | 5/5 |
| [Th]-Lys(Pam$_2$Cys)-[B] 10 nmole | 4.22 ± 0.33 | 1/5 |
| [Th]-Lys(Pam$_2$Cys)-[B] 1 nmole | 3.61 ± 1.18 | 0/5 |
| [Th]-Lys(Pam$_2$Cys-Ser-Ser)-[B] 10 nmole | 4.64 ± 0.23 | 0/5 |
| [Th]-Lys(Pam$_2$Cys-Ser-Ser)-[B] 1 nmole | 3.92 ± 0.65 | 1/5 |
| [Th]-[B] in CFA 10 nmole | 4.72 ± 0.21 | 1/5 |
| [Th]-[B] in CFA 1 nmole | 3.56 ± 0.22 | 3/5 |
| Saline in CFA | <2 | 5/5 |

[1]Lipopeptides were administered in saline and the non-lipidated peptide [Th]-[B] and saline controls were inoculated in CFA for the primary inoculation and incomplete Freunds adjuvant for the secondary inoculation. All vaccines were administered by the subcutaneous route.
[2]Fertility experiments were initiated two weeks after the second dose of vaccine.

Systemic Antibody Responses Following Intranasal (i.n.) Immunization

We inoculated [Th]-Lys(Pam$_2$Cys-Ser-Ser)-[B] and Pam$_2$Cys-Ser-Ser-[Th]-[B] in saline by the intranasal route. The same vaccines were also inoculated by the subcutaneous route and the systemic anti-LHRH antibody responses were measured. The solution used for inoculation of [Th]-Lys(Pam$_2$Cys-Ser-Ser)-[B] was clear and the one for Pam$_2$Cys-Ser-Ser-[Th]-[B] was opalescent indicating solubility differences between the two preparations.

Following two intranasal inoculations, each of the vaccines induced similar titres of serum anti-LHRH antibodies which were slightly lower than those induced following subcutaneous inoculation (Table 5). The more soluble [Th]-Lys(Pam$_2$Cys-Ser-Ser)-[B] induced significantly higher levels of anti-LHRH antibody 4 weeks after a single dose than did the less soluble Pam$_2$Cys-Ser-Ser-[Th]-[B] ($p=0.00007$); in fact this was similar to the result obtained following subcutaneous inoculation. The fertility trial showed that two intranasal inoculations of [Th]-Lys(Pam$_2$Cys-Ser-Ser)-[B] prevented all mice from becoming pregnant in contrast to those animals receiving Pam$_2$Cys-Ser-Ser-[Th]-[B] intranasally in which 3 of 5 mice became pregnant.

A comparison of the longevity of the responses induced by the two constructs when administered by the two different routes is also shown in Table 5. Twenty six weeks following the second dose of vaccine the levels of antibody in all mice had dropped below those observed 2 weeks after receiving the second dose. The decrease in anti-LHRH antibody in the group that received [Th]-Lys(Pam$_2$Cys-Ser-Ser)-[B] subcutaneously, however, was much less apparent again indicating the superiority of a configuration in this context wherein Pam$_2$Cys-Ser-Ser is attached at the approximate centre of the molecule.

TABLE 5

Anti-LHRH antibody titres and fertility status of mice inoculated intranasally or subcutaneously with various peptide and lipopeptide constructs

| | Geometric mean anti-LHRH antibody titres ($\log_{10}$) | | | | [2]Pregnancy |
|---|---|---|---|---|---|
| [1]Inoculum | 4 weeks after $1^{st}$ Dose | 2 weeks after $2^{nd}$ Dose | 10 weeks after $2^{nd}$ Dose | 26 weeks after $2^{nd}$ Dose | No. animals per group that dropped litters |
| Pam$_2$Cys-Ser-Ser-[Th]-[B] (subcutaneous) | 2.40 ± 0.5 | 4.60 ± 0.35 | 3.80 ± 0.40 | 3.30 ± 0.39 | 0/5 |
| Pam$_2$Cys-Ser-Ser-[Th]-[B] (intranasal) | 1.88 ± 0.42 | 4.28 ± 0.75 | 3.18 ± 0.45 | 2.90 ± 0.23 | 3/5 |
| [Th]-Lys(Pam$_2$Cys-Ser-Ser)-[B] (subcutaneous) | 3.46 ± 0.35 | 4.62 ± 0.35 | 4.18 ± 0.32 | 4.02 ± 0.44 | 0/5 |
| [Th]-Lys(Pam$_2$Cys-Ser-Ser)-[B] (intranasal) | 3.52 ± 0.25 | 4.22 ± 0.19 | 3.46 ± 0.35 | 3.02 ± 0.18 | 0/5 |
| [Th]-[B] in CFA (subcutaneous) | 4.12 ± 0.41 | 4.70 ± 0.36 | 3.88 ± 0.30 | 3.62 ± 0.37 | 0/5 |
| Saline in CFA (subcutaneous) | 1.0 | ND | ND | ND | 5/5 |

[1]Lipopeptide vaccines were inoculated in saline, and non-lipidated [Th]-[B] and saline controls were inoculated in CFA for the primary inoculation and incomplete Freunds adjuvant for the secondary inoculation.
[2]Fertility experiments were initiated two weeks after the second dose of vaccine.

We also determined the titres of individual antibody isotypes that were directed towards LHRH and obtained from animals following two subcutaneous or intranasal doses of the soluble lipopeptide [Th]-Lys(Pam$_2$Cys-Ser-Ser)-[B] (FIG. 4). Intranasal inoculation appeared to induce higher levels of IgG3, IgG2b and possibly IgM than did subcutaneous inoculation even though the amount of total Ig induced by intranasal inoculation was less.

Exposure of DC to Peptides and Lipopeptides Induce Different Levels of Cell Surface MHC Class II Molecules The priming of naïve CD4+ T cells in secondary lymphoid organs by dendritic cells is preceded by maturation of DC upon exposure to antigen. This maturation is characterised by up-regulation of MHC products and co-stimulatory molecules on the DC surface. We therefore determined whether the various peptides and lipopeptides could differentially activate dendritic cells in an attempt to explain the different immunogenic properties of these vaccine candidates.

The results of experiments in which a line of immature DC, D1 cells, were exposed to peptides, stained for surface expression of MHC class II molecules then analysed by flow cytometry, demonstrated that [Th]-Lys(Pam$_2$Cys-Ser-Ser)-[B] was the most effective and Pam$_2$Cys-[Th]-[B] was the least effective in causing maturation of DC (FIG. 5). The ability of [Th]-Lys(Pam$_2$Cys-Ser-Ser)-[B] to up-regulate class II expression approached that of bacterial lipopolysaccharide (LPS) and Pam$_2$Cys-Ser-Ser[Th]-[B] and [Th]-Lys (Pam$_2$Cys)-[B] displayed intermediate levels of activation. The non-lipidated peptide was unable to induce maturation of D1 cells greater than the 26% which occurs spontaneously in culture. The ability of the lipopeptides to induce the maturation of D1 cells was concentration-dependent (data not shown). The relative abilities of these lipopeptides to induce maturation of D1 cells directly reflected their ability to induce antibody, providing a possible mechanism for differences in immunogenicity.

Antibody Responses to the C-Terminal Pentapeptide of LHRH

As shown in FIG. 6, approximately equivalent antibody responses are elicited by lipidated [Th]-Lys(Pam$_2$Cys)-[B] in which [Th] consists of CD4+ T cell epitope from the light chain of influenza hemagglutinin (SEQ ID NO: 1) and [B] is LHRH 1-10 (SEQ ID NO: 2) or LHRH 6-10 (i.e., the last C-terminal 5 residues of LHRH; SEQ ID NO: 4), with or without a serine spacer (Ser-Ser) positioned between the lipid and peptide moieties. These data support the proposition that the usefulness of the lipopeptides is not limited to any specific amino acid sequence being used as the immunizing antigen.

Lipids Other than Pam$_2$Cys are Useful in the Lipopeptide Constructs

Groups of BALB/c mice (6-8 weeks old) were inoculated subcutaneously with 20 nmoles of the peptide immunogens shown in FIG. 7, comprising the lipid moieties Pam$_2$Cys; Ste$_2$Cys; Lau$_2$Cys; or Oct$_2$Cys conjugated to the amino acid sequence set forth in SEQ ID NO: 9 (i.e. a peptide comprising the CDV-F T-helper epitope of SEQ ID NO: 24 conjugated to LHRH 2-10 as set forth in SEQ ID NO: 3, with an internal lysine residue positioned between these epitopes), for both primary and secondary vaccinations. Peptide structures are shown in FIG. 7. All lipopeptides were administered in saline. The non lipidated peptides was administered in CFA as a control. Sera were obtained from blood taken at 4 weeks following the primary vaccination and 2 weeks following the secondary vaccination.

Data shown in FIG. 8 indicate that strong primary and secondary antibody responses can be obtained when the Pam$_2$Cys moiety is substituted for another lipid moiety in the lipopeptide constructs.

Different Spacers can be Used to Separate Lipid from Peptide in the Lipopeptides Groups of BALB/c mice (6-8 weeks old) were inoculated subcutaneously with 20 nmoles of the peptide immunogens shown in FIG. 7, comprising the lipid moiety Pam$_2$Cys conjugated to the amino acid sequence set forth in SEQ ID NO: 9 and separated therefrom using a spacer consisting of a serine homodimer, arginine homodimer or 6-aminohexanoic acid. Peptide structures are shown in FIG. 7. All lipopeptides were administered in saline. The non lipidated peptides was administered in CFA as a control. Sera were obtained from blood taken at 4 weeks following the primary vaccination and 2 weeks following the secondary vaccination.

Data shown in FIG. 9 indicate that strong primary and secondary antibody responses can be obtained when the Pam$_2$Cys moiety is separated from the peptide moiety in the lipopeptide constructs using a variety of different spacers.

The Lipid Moiety can be Attached to an Internal Lysine Residue within the T-Helper Epitope To determine the stringency of a requirement for positioning of the internal lysine residue to which the lipid moiety is attached, we also studied the immunogenicity of a lipopeptide construct wherein the lipid was attached to an internal lysine residue within the T-helper epitope. Groups of BALB/c mice (o weeks and 4 weeks old) were inoculated subcutaneously with 20 nmoles of the peptide immunogens comprising the lipid moiety Pam$_2$Cys conjugated to the amino acid sequence set forth in SEQ ID NO: 9 between the T-helper epitope and B-cell epitope, or alternatively, conjugated to the amino acid sequence set forth in SEQ ID NO: 103 at position Lys-14 within the T-helper epitope. Peptide structures are shown in FIGS. 7 and 10. All lipopeptides were administered in saline. The non lipidated peptide was administered in CFA as a control. Sera were obtained from blood taken at 4 weeks following the primary vaccination and 2 weeks following the secondary vaccination.

Data shown in FIG. 11 indicate that strong antibody responses are obtainable using lipopeptides wherein the lipid moiety is attached to either position, suggesting that strict placement of the internal lysine and, as a consequence, the lipid moiety, is not essential to immunogenicity.

Discussion

In this study we describe the assembly of a variety of lipopeptide immunogens composed of a CD4+ T cell epitope, the self peptide LHRH which includes one or more B cell epitopes and Pam$_3$Cys or Pam$_2$Cys.

Without placing any strict requirement on the need for approximate central positioning of the lipid, we found that the solubility of the resulting vaccine was greatly improved by placing lipids in the approximate centre of the peptide immunogen between the T cell epitope and LHRH instead of at the more usual position at the N-terminus. A clear solution in saline at the concentration required for inoculation could easily be obtained with these branched structures. In contrast, the immunogens in which the lipid was coupled at the N-terminus were less soluble, giving a cloudy or opalescent solution in saline. Investigation of the antibody responses and subsequent fertility trials indicated that the water-soluble lipopeptides induced higher antibody titres 4 weeks after the primary inoculation and were also more efficient in preventing pregnancy than were the less soluble lipopeptides where lipid was attached to the N-terminus. A water-soluble self-adjuvanting vaccine has clear advantages over partially soluble or insoluble material allowing for simplification of the manufacturing process and also more accurate metering of dose.

Investigations into the stringency of a requirement for positioning the lipid moiety indicated that some flexibility is possible, since antibody responses were also observed in immunized animals when the lipid was positioned within the T-helper epitope, rather than between the T-helper epitope and the B-cell epitope.

Investigations into the effects of varying the lipopeptide dose indicated that $Pam_2Cys$-containing lipopeptides are better immunogens than are $Pam_3Cys$-containing peptides. However, other lipidopeptides were also useful in generating strong antibody responses, such as, for example, Step $2Cys$-containing lipopeptides, $Lau_2Cys$-containing lipopeptides, and $Oct_2Cys$-containing lipopeptides.

We found in the present study that insertion of two serine residues or two arginine residues between the lipid moiety and the peptide sequence increased the potency of the resulting $Pam_2Cys$-containing immunogens. When lipid is attached to the N-terminus, the two serine residues could either be acting as an inert spacer between the lipid and the peptide sequence or as an extension of the T helper cell epitope and perhaps modulating immunological activity. In those cases where lipid is coupled to the epsilon-amino group of a lysine residue at the centre of the molecule, the two serine residues or two arginine residues are acting as a spacer, because the inert spacer, 6-aminohexanoic acid achieved similar results.

We also found that the immunogenicity of lipopeptide constructs was not dependent upon the specific amino acid sequence of the T-helper epitope or the B-cell epitope used, indicating general utility of the approach taken to producing a wide range of lipopeptides against different antigenic B-cell epitopes and in a number of different animal hosts.

It is understood that macrophages are stimulated by microbial products which bind to cell surface receptors; the signal resulting from this binding event is transmitted via Toll-like receptors and results in the production of pro-inflammatory cytokines and chemokines. These receptors are also present in populations of DC, and, when engaged, transmit signals for cellular maturation and migration as well as for the production of molecules required for efficient antigen presentation.

The various synthetic lipopeptide vaccines used in this study were found to induce the up-regulation of class II MHC molecules, a marker used to assess DC maturation, on the surface of immature DC. In contrast, the non-lipidated peptide construct was unable to cause maturation of DC indicating that the lipid moiety is responsible for the effect. The hierarchy of lipopeptide-induced maturation of DC reflects the hierarchy of immunogenicity exhibited by the peptide constructs implies that the ability of the vaccine to interact with and induce maturation of DC leads to a better immune response, possibly by increasing the efficiency of $CD4^+$ T cell priming by DC that have been signalled to mature and migrate to the draining lymph node.

The lipopeptides can trigger an immune response in the absence of additional adjuvant and can therefore be delivered by non-parenteral routes. We therefore investigated the antibody response following intranasal inoculation of $Pam_2Cys$-containing peptides. The results obtained here showed that intranasal inoculation of [Th]-Lys($Pam_2Cys$-Ser-Ser)-[B] or $Pam_2Cys$-Ser-Ser-[Th]-[B] induced lower titres of systemic anti-LHRH antibody than those induced by inoculation by the subcutaneous route and also that the isotype profiles of immunoglobulins were different. Intranasal inoculation of the soluble lipopeptide [Th]-Lys($Pam_2Cys$-Ser-Ser)-[B] induced higher levels of IgG2b and IgG3, but lower levels of IgG1 and IgG2a compared to subcutaneous immunization. This may indicate that the two routes of immunization result in the induction of somewhat different subsets of T cells providing help for antibody production which may, in part, be due to the different populations of DCs encountered at different sites. It may also reflect a preference that dendritic cells have for molecules with unusual geometries.

Intranasal inoculation of the water-soluble peptide construct [Th]-Lys($Pam_2Cys$-Ser-Ser)-[B] induced significantly higher anti-LHRH antibody titres 4 weeks after the first dose of vaccine than did insoluble $Pam_2Cys$-Ser-Ser-[Th]-[B]. Fertility trials carried out with these mice demonstrated that only intranasal inoculation with [Th]-Lys($Pam_2Cys$-Ser-Ser)-[B] was able to totally prevent reproduction. Although similar antibody titres were apparent in both groups of mice following the second dose of antigen, high titres of antibody were only elicited during the primary response to [Th]-Lys($Pam_2Cys$-Ser-Ser)-[B]. It is therefore possible that for an immunocontraceptive vaccine to be effective, the time for which high titres of antibody are present is an important determinant of efficacy.

Taken together, the measurements of antibody titres and the results of the fertility trials demonstrate that placement of $Pam_2Cys$ between the B cell epitope and the T helper epitope, at the approximate centre of a totally synthetic peptide vaccine increases the solubility and also the immunogenicity of the vaccine. This improved immunogenicity is further improved by the introduction of two serine residues between the lipid and the peptide sequence of these branched peptide vaccines. The finding that incorporation of lipid, self-adjuvanting moieties into different positions of peptide-based vaccines profoundly alters physical, immunogenic and biological properties provides another strategy for successful vaccine design.

EXAMPLE 3

Studies on Lipopeptides Comprising a B Cell Epitope from the M Protein of Group A *streptococcus*

The Effect of Multiple Lipids

To test whether or not immunogenicity of the lipopeptides was dependent upon the number of lipids conjugated to the peptides, and to demonstrate that effective lipopeptides could be formulated against different antigenic B-cell epitope-containing peptides, we produced lipopeptides comprising a peptide moiety that comprises the CDV-F P25 T-helper epitope and a Group A *Streptococcus* B cell epitope J14 (i.e. the peptide moiety has the amino acid sequence of SEQ ID NO: 105), and one or two lipid moieties. The lipoamino acid moiety $Pam_2Cys$-Ser-Ser was added to an internal lysine positioned between the T-helper epitope and the B-cell epitope and, in one construct, an additional lipoamino acid moiety $Pam_2Cys$-Ser-Ser was also added to an N-terminal lysine in the T-helper epitope.

Female outbred Quackenbush mice 4-6 weeks old (15/group) were inoculated intranasally with 60 μg of peptide-based vaccine in a total volume of 30 μl PBS. Mice received three doses of vaccine at 21-day intervals. Fecal IgA was determined 6 days following the last dose of antigen. Seven days following the final dose mice were bled from the tail vein and J14-specific serum IgG was determined. Indirect bacteriocidal assays were also performed to determine the ability of sera from immunized mice to opsonise or "kill" the M1 GAS strain in vitro. Eight days following the final dose saliva was collected from individual mice and the average J14-specific salivary IgA antibody titres were determined by standard ELISA. Two weeks after the last dose of antigen, mice were challenged intranasally with M1 GAS strain and survival determined at various time points afterwards.

Data in FIG. 12 indicate that significant (P<0.05) serum IgG titres were elicited using either lipopeptide compared to non-lipidated peptides or PBS, indicating that the lipopeptide constructs are not dependent upon the selection of T-helper or B-cell epitope, and that lipopeptides comprising single or multiple lipid moieties can be used to elicit high serum IgG levels following intranasal immunization.

Data presented in FIG. 13 also indicate that sera collected from mice immunized with J14-containing lipopeptides having one or two lipid moieties were also capable of significant (P<0.05) killing of GAS compared to sera collected from animals immunized with control non-lipidated peptides or PBS.

Data presented in FIG. 14 indicate that mice inoculated J14-containing lipopeptides having one or two lipid moieties had significantly (P<0.05) higher saliva IgA titres than the control groups that were immunized control non-lipidated peptides or PBS. However, the monolipidated peptide was far superior than the bi-lipidated peptide in inducing saliva IgA levels by intranasal administration.

Interestingly, only mice inoculated with mono-lipidated J14-containing peptide, wherein the lipid moiety was positioned between the T-helper epitope and the B-cell epitope (i.e., [Th]-Lys(Pam$_2$Cys-Ser-Ser)-[J14]) had significant (P<0.05) fecal IgA titres at 6 days following final immunization, compared to PBS or non-lipidated peptide (FIG. 15). This may be a consequence of timing, since fecal IgA was determined before saliva IgA or serum IgG levels were determined. Alternatively, it may be a consequence of the intranasal administration route. Other explanations cannot be excluded at present.

As shown in FIG. 16, mice inoculated with mono-lipidated J14-containing peptide, wherein the lipid moiety was positioned between the T-helper epitope and the B-cell epitope (i.e., [Th]-Lys(Pam$_2$Cys-Ser-Ser)-[J14]) also demonstrated the best survival following intranasal challenge with GAS, compared to the bi-lipidated peptide or non-lipidated peptide. However, some protective immunity was conferred by both the bi-lipidated peptide and non-lipidated peptide compared to the J14 peptide alone or PBS.

In summary, the data presented in Examples 2 and 3 indicate that the lipopeptide formulations of the present invention are broadly applicable to inducing strong antibody responses in animals, particularly murine models, with a variety of T-helper epitopes and B-cell epitopes. Additionally, the lipopeptide formulations are particularly suited to intranasal administration, since strong IgG and IgA responses are obtained by this route. However, our data indicate that, at least for J14 immunogens, mono-lipidated peptides may serve as better mucosal adjuvants than lipopeptides comprising multiple lipid moieties.

EXAMPLE 4

Studies on Lipopeptides Comprising a B Cell Epitope from Gastrin

The immunogenicity of lipopeptide immunogens based on gastrin was determined. Female BALB/c mice were inoculated subcutaneously in the base of the tail with 20 nmoles of peptide or lipopeptide immunogens. All lipopeptides were administered in PBS and the non-lipidated peptides were administered in CFA. Saline emulsified with CFA was used as a negative control. The peptides used were Gastrin-17 (sequence EGPWLEEEEEAYGWMDF; SEQ ID NO: 113); [P25]-Lys-[PentaGastrin] (SEQ ID NO: 110) in which PentaGastrin is the C-terminal sequence GWMDF of gastrin-17 (i.e., SEQ ID NO: 102); and [P25]-Lys(Pam$_2$Cys-Ser-Ser)-[PentaGastrin]. 4 weeks after immunisation sera was obtained from the animals and at the same time they received a second similar dose of antigen. Mice were bled a second time a further 2 week after the second dose of antigen and antibodies capable of reacting with the peptide gastrin-17 sequence determined in ELISA.

As shown in FIG. 17, mice inoculated with Gastrin-17 in CFA contained levels of anti-Gastrin-17 antibodies equivalent to the negative control of Saline in CFA. While immunisation with the non-lipidated peptide [P25]-Lys-[PentaGastrin] elicited very low levels of anti-Gastrin-17 antibodies, mice challenged with the lipopeptide [P25]-Lys(Pam$_2$Cys-Ser-Ser)-[PentaGastrin] demonstrated high antibody titres similar to that elicited after immunisation with the peptide in CFA. These data again illustrate that the lipopeptide formulations of the present invention are broadly applicable to inducing strong antibody responses in animals, with a variety of T-helper epitopes and B-cell epitopes.

We claim:

1. A method of producing a lipopeptide comprising:
   (i) producing a polypeptide comprising an amino acid sequence that comprises:
      (a) an amino acid sequence of a T helper cell (Th) epitope and an amino acid sequence of a B cell epitope, wherein said amino acid sequences are different; and
      (b) one or more internal lysine residues positioned between the T helper cell epitope and the B cell epitope; and
   (ii) covalently attaching a lipid moiety directly or indirectly to an epsilon-amino group of said one or more internal lysine residues so as to produce a lipopeptide having the lipid moiety attached to the epsilon amino group of said one or more internal lysine residues.

2. The method of claim 1 wherein the polypeptide is synthesized by a chemical synthesis means.

3. The method of claim 1 further comprising producing the lipid moiety.

4. The method of claim 3 comprising synthesizing the lipid moiety as a lipoamino acid.

5. The method according to claim 4 further comprising adding a spacer to an amino acid moiety of the lipoamino acid.

6. The method according to claim 5 wherein the lipid comprises an arginine homodimer or a serine homodimer or a 6-aminohexanoic acid.

7. The method of claim 5 comprising adding the spacer to the lipoamino acid via a terminal carboxy group in a process that comprises performing a condensation, addition, substitution, or oxidation reaction.

8. The method of claim 5 wherein the spacer comprises a terminal protected amino acid residue to facilitate conjugation of the lipoamino acid to the polypeptide.

9. The method of claim 8 comprising de-protecting the terminal protected amino acid of the spacer and conjugating the lipoamino acid to the polypeptide.

10. The method of claim 4 comprising adding a spacer to a non-modified epsilon amino group of the polypeptide in a process comprising performing a nucleophilic substitution reaction.

11. The method of claim 10 wherein the polypeptide has an amino acid sequence comprising a single internal lysine or lysine analog residue and a blocked N-terminus.

12. The method according to claim 10 or 11 wherein the lipid comprises an arginine homodimer or serine homodimer or 6-aminohexanoic acid.

13. The method of claim 1 wherein said lipopeptide has the general Formula (VI):

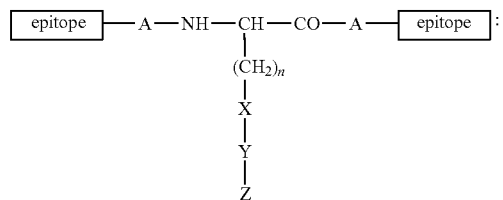

Formula (VI)

wherein:

epitope is said T-helper epitope or said B-cell epitope;

A is either present or absent and consists of an amino acid spacer of about 1 to about 6 amino acids in length;

n is 4;

X is NH;

Y is either present of absent and consists of a spacer of about 1 to about 6 amino acids in length, wherein said spacer comprises arginine, serine or 6-aminohexanoic acid; and Z is a lipoamino acid moiety selected from the group consisting of $Pam_2Cys$, $Pam_3Cys$, $Ste_2Cys$, $Lau_2Cys$, and $Oct_2Cys$.

* * * * *

UNITED STATES PATENT AND TRADEMARK OFFICE
CERTIFICATE OF CORRECTION

PATENT NO.         : 8,367,067 B2                                    Page 1 of 1
APPLICATION NO.    : 12/488485
DATED              : February 5, 2013
INVENTOR(S)        : Jackson et al.

It is certified that error appears in the above-identified patent and that said Letters Patent is hereby corrected as shown below:

In the Claims

Claim 13, Column 105, line 27, after "1," separate "1 wherein".

Claim 13, Column 106, line 19, after "present," delete "of", insert --or--.

Signed and Sealed this
Twenty-sixth Day of November, 2013

Margaret A. Focarino
*Commissioner for Patents of the United States Patent and Trademark Office*

SEQUENCE LISTING

<160> NUMBER OF SEQ ID NOS: 115

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Gly Ala Leu Asn Asn Arg Phe Gln Ile Lys Gly Val Glu Leu Lys Ser
 1               5                  10                  15

<210> SEQ ID NO 2
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 2

Glu His Trp Ser Tyr Gly Leu Arg Pro Gly
 1               5                  10

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

His Trp Ser Tyr Gly Leu Arg Pro Gly
 1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Leu Arg Pro Gly
 1               5

<210> SEQ ID NO 5
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Ala Leu Asn Asn Arg Phe Gln Ile Lys Gly Val Glu Leu Lys Ser
 1               5                  10                  15

Glu His Trp Ser Tyr Gly Leu Arg Pro Gly
            20                  25

<210> SEQ ID NO 6
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Glu His Trp Ser Tyr Gly Leu Arg Pro Gly Gly Ala Leu Asn Asn Arg
 1               5                  10                  15

Phe Gln Ile Lys Gly Val Glu Leu Lys Ser
            20                  25

<210> SEQ ID NO 7
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 7

Gly Ala Leu Asn Asn Arg Phe Gln Ile Lys Gly Val Glu Leu Lys Ser
1               5                   10                  15

Lys Glu His Trp Ser Tyr Gly Leu Arg Pro Gly
            20                  25

<210> SEQ ID NO 8
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu His Trp Ser Tyr Gly Leu Arg Pro Gly Lys Gly Ala Leu Asn Asn
1               5                   10                  15

Arg Phe Gln Ile Lys Gly Val Glu Leu Lys Ser
            20                  25

<210> SEQ ID NO 9
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Leu Ile Pro Asn Ala Ser Leu Ile Glu Asn Cys Thr Lys Ala Glu
1               5                   10                  15

Leu Lys His Trp Ser Tyr Gly Leu Arg Pro Gly
            20                  25

<210> SEQ ID NO 10
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Glu Leu Gly Glu Tyr Glu Lys Leu Leu Asn Ser Val Leu Glu Pro
1               5                   10                  15

Ile Lys Glu His Trp Ser Tyr Gly Leu Arg Pro Gly
            20                  25

<210> SEQ ID NO 11
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Ala Ala Gln Ile Thr Ala Gly Ile Ala Leu His Gln Ser Asn Leu
1               5                   10                  15

Asn Lys Glu His Trp Ser Tyr Gly Leu Arg Pro Gly
            20                  25

<210> SEQ ID NO 12
<211> LENGTH: 28

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Pro Arg Tyr Ile Ala Thr Asn Gly Tyr Leu Ile Ser Asn Phe Asp Glu
 1               5                  10                  15

Ser Lys Glu His Trp Ser Tyr Gly Leu Arg Pro Gly
            20                  25

<210> SEQ ID NO 13
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Leu Ile Pro Asn Ala Ser Leu Ile Glu Asn Cys Thr Lys Ala Glu
 1               5                  10                  15

Leu Lys Gly Leu Arg Pro Gly
            20

<210> SEQ ID NO 14
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Glu Leu Gly Glu Tyr Glu Lys Leu Leu Asn Ser Val Leu Glu Pro
 1               5                  10                  15

Ile Lys Gly Leu Arg Pro Gly
            20

<210> SEQ ID NO 15
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Ala Ala Gln Ile Thr Ala Gly Ile Ala Leu His Gln Ser Asn Leu
 1               5                  10                  15

Asn Lys Gly Leu Arg Pro Gly
            20

<210> SEQ ID NO 16
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Arg Tyr Ile Ala Thr Asn Gly Tyr Leu Ile Ser Asn Phe Asp Glu
 1               5                  10                  15

Ser Lys Gly Leu Arg Pro Gly
```

-continued

```
<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Lys Lys Lys Lys
1               5

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Leu Asn Asn Arg Phe Gln Ile Lys Gly Val Glu Leu Lys Ser
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Ser Glu Ile Lys Gly Val Ile Val His Arg Leu Glu Gly Val
1               5                   10                  15

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Ala Ala Gln Ile Thr Ala Gly Ile Ala Leu His Gln Ser Asn Leu
1               5                   10                  15

Asn

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ile Gly Thr Asp Asn Val His Tyr Lys Ile Met Thr Arg Pro Ser His
1               5                   10                  15

Gln

<210> SEQ ID NO 22
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 22

Tyr Lys Ile Met Thr Arg Pro Ser His Gln Tyr Leu Val Ile Lys Leu
 1               5                  10                  15
Ile

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser His Gln Tyr Leu Val Ile Lys Leu Ile Pro Asn Ala Ser Leu Ile
 1               5                  10                  15
Glu

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Leu Ile Pro Asn Ala Ser Leu Ile Glu Asn Cys Thr Lys Ala Glu
 1               5                  10                  15
Leu

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu Ile Glu Asn Cys Thr Lys Ala Glu Leu Gly Glu Tyr Glu Lys Leu
 1               5                  10                  15
Leu

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Glu Leu Gly Glu Tyr Glu Lys Leu Leu Asn Ser Val Leu Glu Pro
 1               5                  10                  15
Ile

<210> SEQ ID NO 27
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 27

Lys Leu Leu Asn Ser Val Leu Glu Pro Ile Asn Gln Ala Leu Thr Leu
 1               5                  10                  15
Met

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Glu Pro Ile Asn Gln Ala Leu Thr Leu Met Thr Lys Asn Val Lys Pro
 1               5                  10                  15
Leu

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Leu Met Thr Lys Asn Val Lys Pro Leu Gln Ser Leu Gly Ser Gly
 1               5                  10                  15
Arg

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Lys Pro Leu Gln Ser Leu Gly Ser Gly Arg Arg Gln Arg Arg Phe Ala
 1               5                  10                  15
Gly

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Gly Arg Arg Gln Arg Arg Phe Ala Gly Val Val Leu Ala Gly Val
 1               5                  10                  15
Ala

<210> SEQ ID NO 32
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 32

Phe Ala Gly Val Val Leu Ala Gly Val Ala Leu Gly Val Ala Thr Ala
 1               5                  10                  15
Ala

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Val Ala Leu Gly Val Ala Thr Ala Ala Gln Ile Thr Ala Gly Ile
 1               5                  10                  15
Ala

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Ile Ala Leu His Gln Ser Asn Leu Asn Ala Gln Ala Ile Gln Ser
 1               5                  10                  15
Leu

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asn Leu Asn Ala Gln Ala Ile Gln Ser Leu Arg Thr Ser Leu Glu Gln
 1               5                  10                  15
Ser

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Ser Leu Arg Thr Ser Leu Glu Gln Ser Asn Lys Ala Ile Glu Glu
 1               5                  10                  15
Ile

<210> SEQ ID NO 37
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 37

Glu Gln Ser Asn Lys Ala Ile Glu Glu Ile Arg Glu Ala Thr Gln Glu
 1               5                  10                  15

Thr

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Ser Lys Thr Gln Thr His Thr Gln Gln Asp Arg Pro Pro Gln Pro
 1               5                  10                  15

Ser

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Pro Ser Thr Glu Leu Glu Glu Thr Arg Thr Ser Arg Ala Arg His
 1               5                  10                  15

Ser

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Arg His Ser Thr Thr Ser Ala Gln Arg Ser Thr His Tyr Asp Pro Arg
 1               5                  10                  15

Thr

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Pro Arg Thr Ser Asp Arg Pro Val Ser Tyr Thr Met Asn Arg Thr Arg
 1               5                  10                  15

Ser

<210> SEQ ID NO 42
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 42

Thr Arg Ser Arg Lys Gln Thr Ser His Arg Leu Lys Asn Ile Pro Val
 1               5                  10                  15

His

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Thr Glu Leu Leu Ser Ile Phe Gly Pro Ser Leu Arg Asp Pro Ile Ser
 1               5                  10                  15

Ala

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Pro Arg Tyr Ile Ala Thr Asn Gly Tyr Leu Ile Ser Asn Phe Asp Glu
 1               5                  10                  15

Ser

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Cys Ile Arg Gly Asp Thr Ser Ser Cys Ala Arg Thr Leu Val Ser Gly
 1               5                  10                  15

Thr

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Glu Ser Ser Cys Val Phe Val Ser Glu Ser Ala Ile Cys Ser Gln
 1               5                  10                  15

Asn

<210> SEQ ID NO 47
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 47

Thr Ser Thr Ile Ile Asn Gln Ser Pro Asp Lys Leu Leu Thr Phe Ile
  1               5                  10                  15

Ala

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Pro Asp Lys Leu Leu Thr Phe Ile Ala Ser Asp Thr Cys Pro Leu
  1               5                  10                  15

Val

<210> SEQ ID NO 49
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Thr Ala Pro Pro Ala His Gly Val Thr Ser Ala Pro Asp Thr Arg
  1               5                  10                  15

Ala Pro Gly Ser Thr Ala Pro Pro
              20

<210> SEQ ID NO 50
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Val Thr Ser Ala Pro Asp Thr Arg Pro Ala Pro Gly Ser Thr Ala
  1               5                  10                  15

Ser Ser Leu

<210> SEQ ID NO 51
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Val Thr Ser Ala Pro Asp Thr Arg Pro Ala Pro Gly Ser Thr Ala
  1               5                  10                  15

Ser Leu

<210> SEQ ID NO 52
<211> LENGTH: 27
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Thr Ala Pro Pro Ala His Gly Val Thr Ser Ala Pro Asp Thr Arg Pro
  1               5                  10                  15

Ala Pro Gly Ser Thr Ala Pro Pro Lys Lys Gly
             20                  25

<210> SEQ ID NO 53
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ser Thr Ala Pro Pro Ala His Gly Val Thr Ser Ala Pro Asp Thr Arg
  1               5                  10                  15

Pro Ala Pro Gly Ser Thr Ala Pro Pro Lys
             20                  25

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Val Ala Glu
  1

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Ala Ser Gly Val Ala Glu Thr Thr Asn
  1               5                  10

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Thr Ala Lys Ser Lys Lys Phe Pro Ser Tyr Thr Ala Thr Tyr Gln Phe
  1               5                  10                  15

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 57

Glu Ala Glu Glu Ala Ala Arg Leu Gln Ala
1               5                   10

<210> SEQ ID NO 58
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Phe Arg Glu Arg Thr Leu Thr Gly Gln Arg Ala Cys Asn Asp Val Asn
1               5                   10                  15

Ser Glu

<210> SEQ ID NO 59
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asn Pro Leu Glu Thr Ser Gly Ala Ser Thr Val Gly Phe Arg Glu Arg
1               5                   10                  15

Thr Leu

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ile Arg Glu Thr Arg Lys Arg Gln Lys Met Val Asp Asp Ala Val Asn
1               5                   10                  15

Glu Tyr

<210> SEQ ID NO 61
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Lys Ala Pro Val Val Lys Glu Gly Pro Tyr Glu Gly Pro Val Lys
1               5                   10                  15

Lys Pro Val

<210> SEQ ID NO 62
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 62

Ala Gly Pro Leu Glu Arg Gln Lys Pro Leu Lys Val Lys Ala Lys Ala
  1               5                  10                  15

Pro Val Val

<210> SEQ ID NO 63
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Lys Val Arg Ala Lys Leu Pro Gln Gln Glu Gly Pro Tyr Ala Gly Pro
  1               5                  10                  15

Leu Glu Arg

<210> SEQ ID NO 64
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Pro Tyr Thr Gly Pro Leu Glu Arg Gln Arg Pro Leu Lys Val Arg
  1               5                  10                  15

Ala Lys Leu

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Val Gly Arg Leu Ile Phe Ser Gly Glu Ala Leu Thr Tyr Lys Asp Ile
  1               5                  10                  15

Val Val

<210> SEQ ID NO 66
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Thr Lys His Phe Arg Asp Thr Ala Arg Met Lys Lys Gly Thr Pro Val
  1               5                  10                  15

Val Gly Val

<210> SEQ ID NO 67
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 67

Ser Gly Ala Pro Pro Thr Asp Leu Gln Lys Met Val Met Gly Asn Thr
1               5                   10                  15

Lys Pro Val

<210> SEQ ID NO 68
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asn Lys Tyr Ser Ala Ser Gly Ser Gly Val Arg Gly Asp Phe Gly Ser
1               5                   10                  15

Leu Ala Pro Arg Val Ala Arg Gln Leu Pro Ala Ser Phe Asn Tyr Gly
            20                  25                  30

Ala Ile Lys
        35

<210> SEQ ID NO 69
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Leu Tyr Thr Lys Val Val His Tyr Arg Lys Trp Ile Lys Asp Thr Ile
1               5                   10                  15

Val Ala Asn Pro
            20

<210> SEQ ID NO 70
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ala Val Lys Val Met Asp Leu Pro Gln Glu Pro Ala Leu Gly Thr Thr
1               5                   10                  15

Cys Tyr Ala

<210> SEQ ID NO 71
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ile Val Gly Gly Trp Glu Cys Glu Lys His Ser Gln Pro Trp Gln Val
1               5                   10                  15

Leu Val Ala Ser
            20

<210> SEQ ID NO 72
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Cys Ala Gln Val His Pro Gln Lys Val Thr Lys Phe Met Leu
 1               5                  10

<210> SEQ ID NO 73
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Tyr Leu Met Leu Leu Arg Leu Ser Glu Pro Ala Glu Leu Thr Asp Asp
 1               5                  10                  15

Ala Val Lys Val Met
            20

<210> SEQ ID NO 74
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Leu Leu Lys Asn Arg Phe Leu Arg Pro Gly Asp Asp Ser Ser His Asp
 1               5                  10                  15

Leu Met Leu Leu Tyr
            20

<210> SEQ ID NO 75
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ile Leu Leu Gly Arg His Ser Leu Phe His Pro Glu Asp Thr Gly Gln
 1               5                  10                  15

Val Phe Gln Val Tyr
            20

<210> SEQ ID NO 76
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Thr Cys Asp Asp Pro Arg Phe Gln Asp Ser Ser Ser Ser Lys Ala Pro
 1               5                  10                  15

Pro Pro Ser Leu Pro Ser Pro Ser Arg Leu Pro Gly Pro Ser Asp Thr
            20                  25                  30

Pro Ile Leu Pro Gln
```

<210> SEQ ID NO 77
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Cys Gln Asp Ser Lys Val Thr Glu Ile Pro Thr Leu Pro Arg Asn Ala
 1               5                  10                  15

Ile

<210> SEQ ID NO 78
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asn Lys Gly Asp Cys Gly Thr Pro Ser His Ser Arg Arg Gln Pro His
 1               5                  10                  15

Val Met Ser

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Trp Leu Cys Phe Pro Leu Cys Leu Ala Leu Pro
 1               5                  10

<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Leu Gly Gly Leu Tyr Cys Gly Pro Ser Ser Phe
 1               5                  10

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Ser Ile Thr Arg Asp Ser Ile Phe Arg Leu Arg
 1               5                  10

<210> SEQ ID NO 82
<211> LENGTH: 12
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 82

Ser Ala Leu Pro Val Asn Ile Gln Val Phe Thr Leu
 1               5                  10

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Glu Leu Gln Ile Ala Lys Asp Glu Arg Tyr Gly Ser
 1               5                  10

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Val Lys Leu Leu Arg Glu Pro Ile Tyr Val Glu Val
 1               5                  10

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Pro Pro Ala Gln Tyr Ser Trp Leu Ile Asp Gly Asn
 1               5                  10

<210> SEQ ID NO 86
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ala Asn Ala Ser Gln Thr Asp Asn Gly Val Asn Arg Ser Gly Ser Glu
 1               5                  10                  15

Asp Pro Thr Val
            20

<210> SEQ ID NO 87
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87
```

```
Pro Glu Thr Lys His Pro Lys Gly Val Glu Lys Tyr Gly Pro Glu
 1               5                  10                  15

Ala Ser Ala Phe
             20

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Leu Val Leu Leu Asp Tyr Gln Gly Met Leu Pro Val Cys Pro Leu
 1               5                  10                  15

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Thr Lys Pro Ser Asp Gly Asn Cys Thr Cys Ile Pro Ile Pro Ser
 1               5                  10                  15

<210> SEQ ID NO 90
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Met Gln Trp Asn Ser Thr Thr Phe His Gln Ala Leu Leu
 1               5                  10

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Ala Phe Glu Asp Leu Arg Val Ser Ser Phe Ile Arg Gly Thr
 1               5                  10                  15

<210> SEQ ID NO 92
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ser Asn Glu Asn Met Glu Thr Met Asp Ser Ser Thr Leu Glu
 1               5                  10

<210> SEQ ID NO 93
<211> LENGTH: 19
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 93

His Pro Leu Ile Leu Asp Thr Cys Thr Ile Glu Gly Leu Ile Tyr Gly
 1               5                  10                  15

Asn Pro Ser

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Tyr Gln Arg Ile Gln Ile Phe Pro Asp Thr
 1               5                  10

<210> SEQ ID NO 95
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ile Gln Ile Phe Pro Asp Thr Ile Trp Asn Val Ser Tyr Ser Gly Thr
 1               5                  10                  15

Ser Lys

<210> SEQ ID NO 96
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Cys Lys Tyr Ser Ala Ser Gly Ser Gly Val Arg Gly Asp Phe Gly Ser
 1               5                  10                  15

Leu Ala Pro Arg Val Ala Arg Cys Leu Pro Ala Ser Phe Asn Thr Gly
             20                  25                  30

Ala Ile Lys Asn Lys Tyr
             35

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Glu Gln Gln Trp Asn Phe Ala Gly Ile Glu Ala Ala Ala
 1               5                  10

<210> SEQ ID NO 98
<211> LENGTH: 23
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 98

Ala Ala Ala Trp Gly Gly Ser Gly Ser Glu Ala Tyr Gln Gly Val Gln
 1               5                  10                  15
Gln Lys Trp Asp Ala Thr Ala
             20

<210> SEQ ID NO 99
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Gly Pro Thr Arg Thr Ile Gly Gly Ser Gln Ala Gln Thr Ala Ser
 1               5                  10                  15
Gly Leu Val Ser Met Phe Ser Val Gly Pro Ser Gln Lys
             20                  25

<210> SEQ ID NO 100
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Lys Phe Gln Asp Ala Tyr Asn Ala Ala Gly Gly His
 1               5                  10

<210> SEQ ID NO 101
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Lys Gln Ala Glu Asp Lys Val Lys Ala Ser Arg Glu Ala Lys Lys Gln
 1               5                  10                  15
Val Glu Lys Ala Leu Glu Gln Leu Glu Asp Lys Val Lys
             20                  25

<210> SEQ ID NO 102
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Trp Met Asp Phe
 1               5

<210> SEQ ID NO 103
<211> LENGTH: 26
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 103

Lys Leu Ile Pro Asn Ala Ser Leu Ile Glu Asn Cys Thr Lys Ala Glu
 1               5                  10                  15

Leu His Trp Ser Tyr Gly Leu Arg Pro Gly
            20                  25

<210> SEQ ID NO 104
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Lys Leu Ile Pro Asn Ala Ser Leu Ile Glu Asn Cys Thr Lys Ala Glu
 1               5                  10                  15

Leu Gly Leu Arg Pro Gly
            20

<210> SEQ ID NO 105
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Lys Leu Ile Pro Asn Ala Ser Leu Ile Glu Asn Cys Thr Lys Ala Glu
 1               5                  10                  15

Leu Lys Gln Ala Glu Asp Lys Val Lys Ala Ser Arg Glu Ala Lys Lys
            20                  25                  30

Gln Val Glu Lys Ala Leu Glu Gln Leu Glu Asp Lys Val Lys
        35                  40                  45

<210> SEQ ID NO 106
<211> LENGTH: 47
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Lys Leu Ile Pro Asn Ala Ser Leu Ile Glu Asn Cys Thr Lys Ala Glu
 1               5                  10                  15

Leu Lys Lys Gln Ala Glu Asp Lys Val Lys Ala Ser Arg Glu Ala Lys
            20                  25                  30

Lys Gln Val Glu Lys Ala Leu Glu Gln Leu Glu Asp Lys Val Lys
        35                  40                  45

<210> SEQ ID NO 107
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107
```

Gly Ala Leu Asn Asn Arg Phe Gln Ile Lys Gly Val Glu Leu Lys Ser
1               5                   10                  15

Lys Gln Ala Glu Asp Lys Val Lys Ala Ser Arg Glu Ala Lys Lys Gln
            20                  25                  30

Val Glu Lys Ala Leu Glu Gln Leu Glu Asp Lys Val Lys
        35                  40                  45

<210> SEQ ID NO 108
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Ala Leu Asn Asn Arg Phe Gln Ile Lys Gly Val Glu Leu Lys Ser
1               5                   10                  15

Lys Lys Gln Ala Glu Asp Lys Val Lys Ala Ser Arg Glu Ala Lys Lys
            20                  25                  30

Gln Val Glu Lys Ala Leu Glu Gln Leu Glu Asp Lys Val Lys
        35                  40                  45

<210> SEQ ID NO 109
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Lys Leu Ile Pro Asn Ala Ser Leu Ile Glu Asn Cys Thr Lys Ala Glu
1               5                   10                  15

Leu Gly Trp Met Asp Phe
            20

<210> SEQ ID NO 110
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Lys Leu Ile Pro Asn Ala Ser Leu Ile Glu Asn Cys Thr Lys Ala Glu
1               5                   10                  15

Leu Lys Gly Trp Met Asp Phe
            20

<210> SEQ ID NO 111
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Ala Leu Asn Asn Arg Phe Gln Ile Lys Gly Val Glu Leu Lys Ser
1               5                   10                  15

Gly Trp Met Asp Phe
            20

```
<210> SEQ ID NO 112
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Ala Leu Asn Asn Arg Phe Gln Ile Lys Gly Val Glu Leu Lys Ser
 1               5                  10                  15

Lys Gly Trp Met Asp Phe
            20

<210> SEQ ID NO 113
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Glu Gly Pro Trp Leu Glu Glu Glu Glu Ala Tyr Gly Trp Met Asp
 1               5                  10                  15

Phe

<210> SEQ ID NO 114
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Pam3Cys

<400> SEQUENCE: 114

Cys Ser Lys Lys Lys Lys
 1               5

<210> SEQ ID NO 115
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Lys Gly Leu Arg Pro Gly
 1               5
```